(12) United States Patent
Follenzi et al.

(10) Patent No.: US 11,344,631 B2
(45) Date of Patent: May 31, 2022

(54) PROMOTER FOR CELL-SPECIFIC GENE EXPRESSION AND USES THEREOF

(71) Applicant: Universita' del Piemonte Orientale, Vercelli (IT)

(72) Inventors: Antonia Follenzi, Novara (IT); Diego Zanolini, Novara (IT); Rosella Fama', Vercelli (IT); Simone Merlin, Novara (IT)

(73) Assignee: Universita' del Piemonte Orientale, Vercelli (IT)

( * ) Notice: Subject to any disclaimer, the term of this patent is extended or adjusted under 35 U.S.C. 154(b) by 632 days.

(21) Appl. No.: 16/308,446

(22) PCT Filed: Jun. 12, 2017

(86) PCT No.: PCT/IB2017/053460
§ 371 (c)(1),
(2) Date: Dec. 7, 2018

(87) PCT Pub. No.: WO2017/212460
PCT Pub. Date: Dec. 14, 2017

(65) Prior Publication Data
US 2019/0269796 A1  Sep. 5, 2019

(30) Foreign Application Priority Data

Jun. 10, 2016 (IT) .......... 102016000059985

(51) Int. Cl.
| | |
|---|---|
| A61K 48/00 | (2006.01) |
| A61P 7/04 | (2006.01) |
| A61K 38/37 | (2006.01) |
| C07K 14/755 | (2006.01) |
| C12N 15/11 | (2006.01) |
| C12N 15/86 | (2006.01) |
| A61K 38/00 | (2006.01) |

(52) U.S. Cl.
CPC .......... *A61K 48/0058* (2013.01); *A61K 38/37* (2013.01); *A61P 7/04* (2018.01); *C07K 14/755* (2013.01); *C12N 15/111* (2013.01); *C12N 15/86* (2013.01); *A61K 38/00* (2013.01); *C12N 2740/16043* (2013.01); *C12N 2830/008* (2013.01); *C12N 2830/85* (2013.01)

(58) Field of Classification Search
CPC .. A61K 48/00; A61K 48/0066; C07K 14/755; C12N 15/90; C12N 15/111
USPC ..... 435/6.1, 91.1, 91.31, 455, 458; 536/23.1
See application file for complete search history.

(56) References Cited

U.S. PATENT DOCUMENTS

| | | | | |
|---|---|---|---|---|
| 2015/0306250 A1* | 10/2015 | Laterza | .............. | A61K 48/0066 424/278.1 |
| 2016/0045575 A1* | 2/2016 | Howard | ................ | C12N 15/111 514/44 R |
| 2019/0351073 A1* | 11/2019 | Laterza | .............. | A61K 48/0066 |

OTHER PUBLICATIONS

Pan J., et al., "Patterns of expression of factor VIII and von Willebrand factor by endothelial cell subsets in vivo", May 12, 2016, retrieved by the Internet http://www.bloodjournal.org/content/bl/codjournal/128/1/104.full.pdf.
(Continued)

*Primary Examiner* — Jane J Zara
(74) *Attorney, Agent, or Firm* — Silvia Salvadori, P.C.; Silvia Salvadori

(57) ABSTRACT

The present invention refers to nucleotide sequences used for driving the expression of a therapeutic gene, preferably FVIII and/or its variants specifically in endothelial cells and/or hematopoietic, preferably myeloid cells. The sequences are useful for gene and/or cell therapy, preferably for treating hemophilia, more preferably type A hemophilia.

Figure 1:
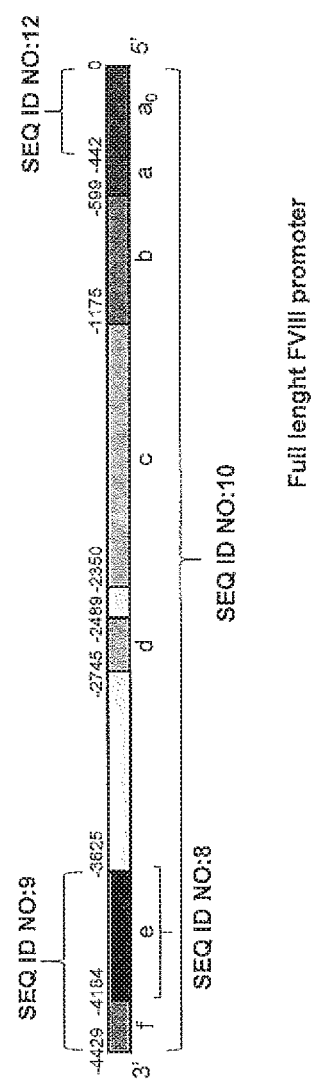

5 Claims, 7 Drawing Sheets
Specification includes a Sequence Listing.

(56) References Cited

OTHER PUBLICATIONS

McGlynn L. K., et al., "Role of the liver-enriched transcription factor hepatocyte nuclear factor 1 in transcriptional regulation of the factor VIII gene", Molecular and Cellular Biology, vol. 16, No. 5, May 1, 2016 pp. 1936-1945.

Merlin S., et al., "A novel platform for immune tolerance induction in hemophilia A mice," Molecular Therapy, vol. 25, No. 8, Aug. 2, 2017, pp. 1815-1830.

Search Report and Written Opinion of PCT/IB2017/053460 dated Sep. 19, 2017.

Zanolini D., et al., "Targeted FVIII expression under the control of its native promoter for hemophilia A gene and cell therapy," Human Gene Therapy, vo. 27, No. 11, Nov. 2016, p. A147.

Zanolini D., et al., "Targeting transgene expression under the controlof FVIII promoter: determining the identity of FVIII producing cells for gene therapy of Hemophilia A", Human Gene Therapy, vol. 25, No. 11, Nov. 2014, pp. A70.

Cannizzo E.S., et al., "Transcriptional and post-transcriptional targeting of FVIII expression to overcome immunological responses to gene therapyfor Hemophilia A", Human Gene Therapy, vol. 24, No. 12, Dec. 2013, p. A50.

Figueiredo M., et al., "Human factor VIII gene, promoter region—HSU24224" Jul. 14, 1995.

Merlin S., et al., "Targeting FVIII expression to myeloid cells to overcome immunological responses to gene therapy for hemophilia A", Molecular Therapy vol. 22, suppl. 1, May 2014, p. S305.

Merlin S., et al., "Targeting FVIII expression to specific cell-types to overcome immunological responses for Hemophilia A gene therapy," Human Gene Therapy, vol. 25, No. 11, Nov. 2014, pp. A38-A39.

Merlin S., et al., "Transcriptional and post-transcriptional targeting of FVIII expression to overcome immunological responses to gene therapy to hemophilia A", Journal of Hepatology, vol. 60, No. 1., suppl. S, Apr. 2014, pp. S119-S120.

Shovlin C. et al, "Endothelial cell processing and alternatively spliced transcripts of factor VIII: potential implications for coagulation cascades and pulmonary hypertension", PLOS ONE Public Library of Science, US, vol. 5, No. 2, Feb. 11, 2010, pp. e9154-1.

\* cited by examiner

Fig.6
A
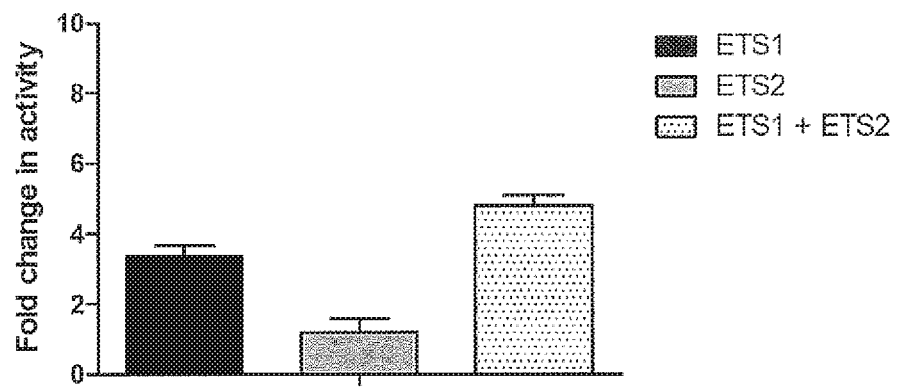
B
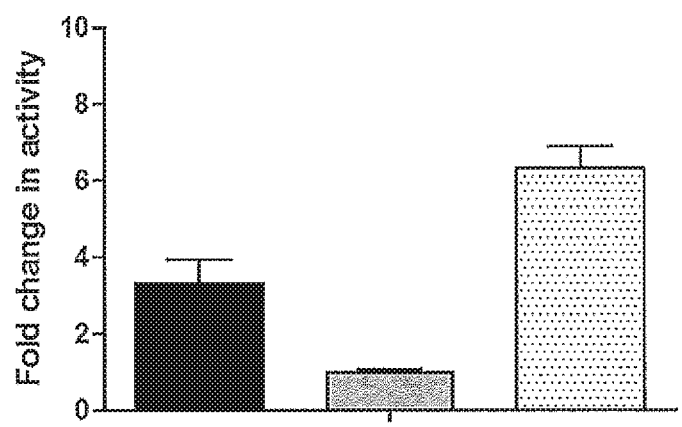
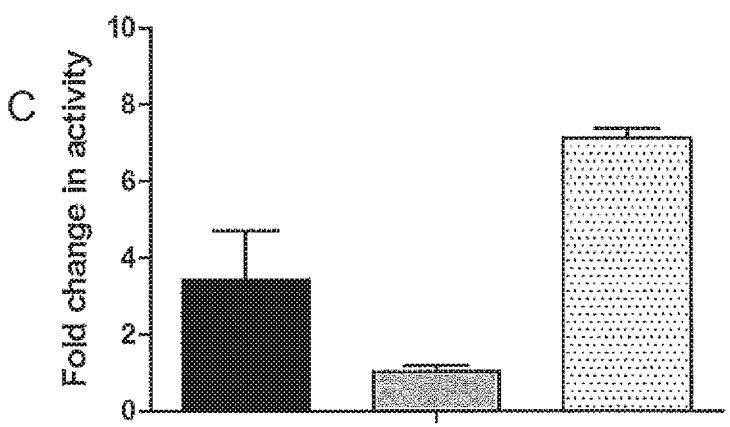

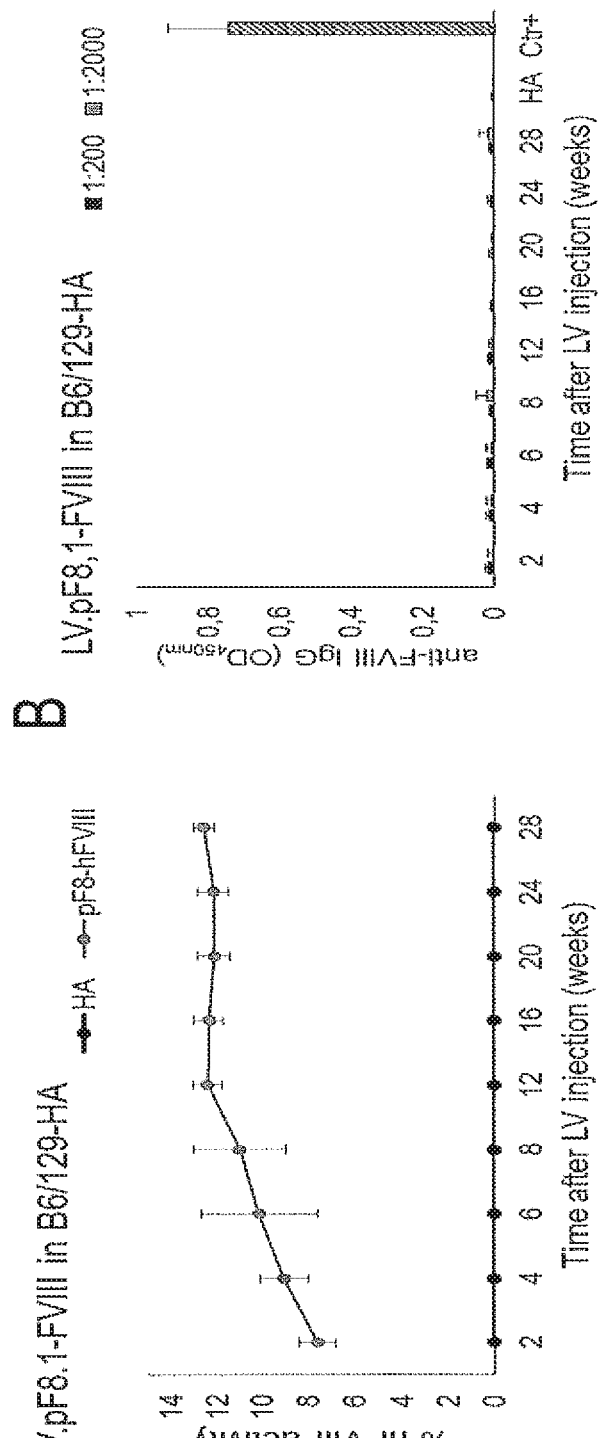

SEQUENCE LISTING

```
<160> NUMBER OF SEQ ID NOS: 30

<210> SEQ ID NO 1
<211> LENGTH: 1175
<212> TYPE: DNA
<213> ORGANISM: Artificial Sequence
<220> FEATURE:
<223> OTHER INFORMATION: LV.pF8.1

<400> SEQUENCE: 1
gagctcacca tggctacatt ctgatgtaaa gagatatatc ctatacctgg gccaaatgta      60
aacagcctgg aaaagtgtta ggttaaaaac aaaacaaaat aaataaatga ataaatgcca     120
ggtggttatg agtgctattg agaaaaatga agccaagagg gatatcagtg atgcaggtgg     180
gggtaaagag cttacaacat aaatgtggtg ttccatattt aaacctcatt caacagggaa     240
gattggagct gaaatgtgaa ggagttgtgg gagtggaact acgtggaaat ctggggggaaa    300
```

| | |
|---|---|
| ggtgttttgg gtaaaagaaa tagcaagtgt tgaggtccag gggcatgagt gtgcttgata | 360 |
| ttttagggaa gagtaaggag accagtataa ccagagtgag atgagactac agaggtcagg | 420 |
| agaaagggca tgcagaccat gtgggatgct ctaggaccta ggccatggta agatgtagg | 480 |
| gttttacccct gatggaggtc agaagccatt ggaggattct gagaagagga gtgacaggac | 540 |
| tcgctttata gttttaaatt ataactataa attatagttt ttaaaacaat agttgcctaa | 600 |
| cctcatgtta tatgtaaaac tacagttta aaaactataa attcctcata ctggcagcag | 660 |
| tgtgaggggc aagggcaaaa gcagagagac taacaggttg ctggttactc ttgctagtgc | 720 |
| aagtgaattc tagaatcttc gacaacatcc agaacttctc ttgctgctgc cactcaggaa | 780 |
| gagggttgga gtaggctagg aataggagca caaattaaag ctcctgttca ctttgacttc | 840 |
| tccatccctc tcctcctttc cttaaaggtt ctgattaaag cagacttatg ccccctactgc | 900 |
| tctcagaagt gaatgggtta agtttagcag cctccctttt gctacttcag ttcttcctgt | 960 |
| ggctgcttcc cactgataaa aaggaagcaa tcctatcggt tactgcttag tgctgagcac | 1020 |
| atccagtggg taaagttcct taaaatgctc tgcaaagaaa ttgggacttt tcattaaatc | 1080 |
| agaaatttta cttttttccc ctcctgggag ctaaagatat tttagagaag aattaacctt | 1140 |
| ttgcttctcc agttgaacat ttgtagcaat aagtc | 1175 |

<210> SEQ ID NO 2
<211> LENGTH: 599
<212> TYPE: DNA
<213> ORGANISM: Artificial Sequence
<220> FEATURE:
<223> OTHER INFORMATION: LV.pF8.2

<400> SEQUENCE: 2

| | |
|---|---|
| gttttttaaaa caatagttgc ctaacctcat gttatatgta aaactacagt tttaaaaact | 60 |
| ataaattcct catactggca gcagtgtgag gggcaagggc aaaagcagag agactaacag | 120 |
| gttgctggtt actcttgcta gtgcaagtga attctagaat cttcgacaac atccagaact | 180 |
| tctcttgctg ctgccactca ggaagagggt tggagtaggc taggaatagg agcacaaatt | 240 |
| aaagctcctg ttcactttga cttctccatc cctctcctcc tttccttaaa ggttctgatt | 300 |
| aaagcagact tatgcccccta ctgctctcag aagtgaatgg gttaagttta gcagcctccc | 360 |
| ttttgctact tcagttcttc ctgtggctgc ttcccactga taaaaaggaa gcaatcctat | 420 |
| cggttactgc ttagtgctga gcacatccag tgggtaaagt tccttaaaat gctctgcaaa | 480 |
| gaaattggga cttttcatta aatcagaaat tttactttt tcccctcctg ggagctaaag | 540 |
| atattttaga gaagaattaa ccttttgctt ctccagttga catttgtag caataagtc | 599 |

<210> SEQ ID NO 3
<211> LENGTH: 1698
<212> TYPE: DNA
<213> ORGANISM: Artificial Sequence
<220> FEATURE:
<223> OTHER INFORMATION: LV.pF8.3

<400> SEQUENCE: 3

| | |
|---|---|
| ggggctcgct cgctcagtac ctggaggcga gttcctgacg cgactgcgac tcaatcctcg | 60 |
| cctggtgaag aatattttac ctatgactca ctgaaaataa agacggctga gtgaccgtgt | 120 |
| ttgttcatgt aaacattgaa caaatattta tcggcttctg cgatgtgtcc tactctttta | 180 |
| gtggaggaag acacatttta tttatgtatt taatttttct tttgaatttt acatgcgagt | 240 |
| tatacttaat aaaactcact tcaaaatata ccttcaacag aaaatccagc aacagtttct | 300 |

```
attatgttag ttaaaacagc cagtcttttc ctttactttt aaaaattatt cataaatgta      360
attagtgaat gataataaac attgacatct gatccactgc tttaggagtg acacaaatga      420
agttaactca ggctattttc tttataatca ttgtgctatt gttttctttt tcttttcaat      480
tatactgctt aatataggat tttgtggcac cataggagtt gaggagctca ccatggctac      540
attctgatgt aaagagatat atcctatacc tgggccaaat gtaaacagcc tggaaaagtg      600
ttaggttaaa acaaaacaa aataaataaa tgaataaatg ccaggtggtt atgagtgcta      660
ttgagaaaaa tgaagccaag agggatatca gtgatgcagg tgggggtaaa gagcttacaa      720
cataaatgtg gtgttccata tttaaacctc attcaacagg gaagattgga gctgaaatgt      780
gaaggagttg tgggagtgga actacgtgga aatctggggg aaaggtgttt tgggtaaaag      840
aaatagcaag tgttgaggtc caggggcatg agtgtgcttg atattttagg gaagagtaag      900
gagaccagta taaccagagt gagatgagac tacagaggtc aggagaaagg gcatgcagac      960
catgtgggat gctctaggac ctaggccatg gtaaagatgt agggttttac cctgatggag     1020
gtcagaagcc attggaggat tctgagaaga ggagtgacag gactcgcttt atagttttaa     1080
attataacta taaattatag ttttaaaac aatagttgcc taacctcatg ttatatgtaa     1140
aactacagtt ttaaaaacta taaattcctc atactggcag cagtgtgagg ggcaagggca     1200
aaagcagaga gactaacagg ttgctggtta ctcttgctag tgcaagtgaa ttctagaatc     1260
ttcgacaaca tccagaactt ctcttgctgc tgccactcag gaagagggtt ggagtaggct     1320
aggaatagga gcacaaatta aagctcctgt tcactttgac ttctccatcc ctctcctcct     1380
ttccttaaag gttctgatta aagcagactt atgcccctac tgctctcaga agtgaatggg     1440
ttaagtttag cagcctccct tttgctactt cagttcttcc tgtggctgct tcccactgat     1500
aaaaaggaag caatcctatc ggttactgct tagtgctgag cacatccagt gggtaaagtt     1560
ccttaaaatg ctctgcaaag aaattgggac ttttcattaa atcagaaatt ttactttttt     1620
cccctcctgg gagctaaaga tattttagag aagaattaac cttttgcttc tccagttgaa     1680
catttgtagc aataagtc                                                  1698
```

<210> SEQ ID NO 4
<211> LENGTH: 1122
<212> TYPE: DNA
<213> ORGANISM: Artificial Sequence
<220> FEATURE:
<223> OTHER INFORMATION: LV.pF8.4

<400> SEQUENCE: 4

```
ggggctcgct cgctcagtac ctggaggcga gttcctgacg cgactgcgac tcaatcctcg       60
cctggtgaag aatattttac ctatgactca ctgaaaataa agacggctga gtgaccgtgt      120
ttgttcatgt aaacattgaa caaatattta tcggcttctg cgatgtgtcc tactctttta      180
gtggaggaag acacatttta tttatgtatt taattttttct tttgaatttt acatgcgagt      240
tatacttaat aaaactcact tcaaaatata ccttcaacag aaaatccagc aacagtttct      300
attatgttag ttaaaacagc cagtcttttc ctttactttt aaaaattatt cataaatgta      360
attagtgaat gataataaac attgacatct gatccactgc tttaggagtg acacaaatga      420
agttaactca ggctattttc tttataatca ttgtgctatt gttttctttt tcttttcaat      480
tatactgctt aatataggat tttgtggcac cataggagtt gaggttttta aaacaatagt      540
tgcctaacct catgttatat gtaaaactac agttttaaaa actataaatt cctcatactg      600
```

```
gcagcagtgt gaggggcaag ggcaaaagca gagagactaa caggttgctg gttactcttg      660
ctagtgcaag tgaattctag aatcttcgac aacatccaga acttctcttg ctgctgccac      720
tcaggaagag ggttggagta ggctaggaat aggagcacaa attaaagctc ctgttcactt      780
tgacttctcc atccctctcc tcctttcctt aaaggttctg attaaagcag acttatgccc      840
ctactgctct cagaagtgaa tgggttaagt ttagcagcct cccttttgct acttcagttc      900
ttcctgtggc tgcttccac tgataaaaag gaagcaatcc tatcggttac tgcttagtgc      960
tgagcacatc cagtgggtaa agttccttaa aatgctctgc aaagaaattg gacttttca     1020 ttaaatcaga aatttactt ttttcccctc ctgggagcta agatatttt agagaagaat     1080 taaccttttg cttctccagt tgaacatttg tagcaataag tc                       1122
```

<210> SEQ ID NO 5
<211> LENGTH: 1979
<212> TYPE: DNA
<213> ORGANISM: Artificial Sequence
<220> FEATURE:
<223> OTHER INFORMATION: LV.pF8.5

<400> SEQUENCE: 5

```
tcgccaccac ttggcttccg gcacgtgggg cagatgtttc cattcccacg gcggcagcgg       60
aagagggagg gccgggcgcg ccgcggctgc ttgcagtctc cgcaagcggc tacatcacag      120
agctcagcgt gcggtgtcac aggccccgcg gtcccgccca acagatgcac cgagatgcgc      180
gtgcgcagaa agcgtcccgg gggtgaggct ccctccctcg ctctccctct actcccgccc      240
cactctcccc cactttcccc cctccaccca ccgcggccgt cggggctcgc tcgctcagta      300
cctggaggcg agttcctgac gcgactgcga ctcaatcctc gcctggtgaa gaatattta      360 cctatgactc actgaaaata aagacggctg agtgaccgtg tttgttcatg taaacattga      420
acaaatattt atcggcttct gcgatgtgtc ctactctttt agtggaggaa gacacatttt      480
atttatgtat ttaattttc ttttgaattt tacatgcgag ttatacttaa taaaactcac      540
ttcaaaatat accttcaaca gaaaatccag caacagtttc tattatgtta gttaaaacag      600
ccagtctttt cctttacttt taaaaattat tcataaatgt aattagtgaa tgataataaa      660
cattgacatc tgatccactg ctttaggagt gacacaaatg aagttaactc aggctatttt      720
ctttataatc attgtgctat tgttttcttt ttcttttcaa ttatactgct taatatagga      780
ttttgtggca ccataggagt tgaggagctc accatggcta cattctgatg taaagagata      840
tatcctatac ctgggccaaa tgtaaacagc ctggaaaagt gttaggttaa aaacaaaaca      900
aaataaataa atgaataaat gccaggtggt tatgagtgct attgagaaaa atgaagccaa      960
gagggatatc agtgatgcag gtgggggtaa agagcttaca acataaatgt ggtgttccat     1020
atttaaacct cattcaacag ggaagattgg agctgaaatg tgaaggagtt gtgggagtgg     1080
aactacgtgg aaatctgggg gaaaggtgtt ttgggtaaaa gaaatagcaa gtgttgaggt     1140
ccaggggcat gagtgtgctt gatattttag ggaagagtaa ggagaccagt ataaccagag     1200
tgagatgaga ctacagaggt caggagaaag ggcatgcaga ccatgtggga tgctctagga     1260
cctaggccat ggtaaagatg tagggtttta ccctgatgga ggtcagaagc cattggagga     1320
ttctgagaag aggagtgaca ggactcgctt tatagtttta aattataact ataaattata     1380 gttttttaaaa caatagttgc ctaacctcat gttatatgta aaactacagt tttaaaaact     1440
ataaattcct catactggca gcagtgtgag gggcaaggc aaaagcagag agactaacag     1500
gttgctggtt actcttgcta gtgcaagtga attctagaat cttcgacaac atccagaact     1560
```

```
tctcttgctg ctgccactca ggaagagggt tggagtaggc taggaatagg agcacaaatt    1620
aaagctcctg ttcactttga cttctccatc cctctcctcc tttccttaaa ggttctgatt    1680
aaagcagact tatgcccta ctgctctcag aagtgaatgg gttaagttta gcagcctccc    1740
ttttgctact tcagttcttc ctgtggctgc ttcccactga taaaaaggaa gcaatcctat    1800
cggttactgc ttagtgctga gcacatccag tgggtaaagt tccttaaaat gctctgcaaa    1860
gaaattggga cttttcatta aatcagaaat tttactttt tccctcctg ggagctaaag    1920 atattttaga gaagaattaa cctttgctt ctccagttga acatttgtag caataagtc     1979
```

<210> SEQ ID NO 6
<211> LENGTH: 1403
<212> TYPE: DNA
<213> ORGANISM: Artificial Sequence
<220> FEATURE:
<223> OTHER INFORMATION: LV.pF8.6

<400> SEQUENCE: 6

```
tcgccaccac ttggcttccg gcacgtgggg cagatgtttc cattcccacg gcggcagcgg      60
aagagggagg gccgggcgcg ccgcggctgc ttgcagtctc cgcaagcggc tacatcacag     120
agctcagcgt gcggtgtcac aggccccgcg gtcccgccca acagatgcac cgagatgcgc     180
gtgcgcagaa agcgtccgg gggtgaggct ccctccctcg ctctccctct actcccgccc      240
cactctcccc cactttcccc cctccaccca ccgcggccgt cggggctcgc tcgctcagta     300
cctggaggcg agttcctgac gcgactgcga ctcaatcctc gcctggtgaa gaatatttta    360
cctatgactc actgaaaata aagacggctg agtgaccgtg tttgttcatg taaacattga     420
acaaatattt atcggcttct gcgatgtgtc ctactctttt agtggaggaa gacacatttt     480
atttatgtat ttaattttc ttttgaattt tacatgcgag ttatacttaa taaaactcac     540
ttcaaaatat accttcaaca gaaaatccag caacagtttc tattatgtta gttaaaacag     600
ccagtctttt cctttacttt taaaaattat tcataaatgt aattagtgaa tgataataaa     660
cattgacatc tgatccactg ctttaggagt gacacaaatg aagttaactc aggctatttt     720
ctttataatc attgtgctat tgttttcttt ttcttttcaa ttatactgct taatatagga     780
ttttgtggca ccataggagt tgaggttttt aaaacaatag ttgcctaacc tcatgttata    840
tgtaaaacta cagtttttaaa aactataaat tcctcatact ggcagcagtg tgagggcaa    900 gggcaaaagc agagagacta acaggttgct ggttactctt gctagtgcaa gtgaattcta    960
gaatcttcga caacatccag aacttctctt gctgctgcca ctcaggaaga gggttggagt   1020
aggctaggaa taggagcaca aattaaagct cctgttcact ttgacttctc catccctctc   1080
ctcctttcct taaggttct gattaaagca gacttatgcc cctactgctc tcagaagtga   1140
atgggttaag tttagcagcc tccttttgc tacttcagtt cttcctgtgg ctgcttccca    1200
ctgataaaaa ggaagcaatc ctatcggtta ctgcttagtg ctgagcacat ccagtgggta   1260
aagttcctta aaatgctctg caaagaaatt gggactttc attaaatcag aatttttact   1320
tttttcccct cctgggagct aaagatattt tagagaagaa ttaacctttt gcttctccag   1380
ttgaacattt gtagcaataa gtc                                           1403
```

<210> SEQ ID NO 7
<211> LENGTH: 2350
<212> TYPE: DNA
<213> ORGANISM: Artificial Sequence
<220> FEATURE:

<223> OTHER INFORMATION: 0 to 2350 5' FVIII promoter sequence

<400> SEQUENCE: 7

```
cagcagttcc cacaaacgtt accctcacaa tgaatccagc cattttttcac cctctccagt      60
ggtaccatca tagcccaagc cgccaccatt tctcaccccc ggttaacagg ccaccctcct     120
tctacccttta tcctgctaga gtttgtttta tctacagtga tcagaaagat cagcctaaaa    180
gataattctg atcaccaccc tcctctactc acaacccggc cgtgtctccc cattgccctc    240
agtgtagaag tcaatgtccc tttgctgaaa tgcaaccttta gtgaaacttt ccatgactaa    300
cctcctttaa aattgcaacc tggtccaccc ttactccccc ttaccccact tctcttttt    360
gcacagcact tattttacct tctaacatac tgtataatgt actcatgtat tgtaattatt    420
gcttatcatc cctctttcag ttgcttatat ttttcatcaa tgtgtaccca gtgcctagga    480
caatatctgt ctaggacaaa tgggtagtta tgtggctgta ggcaagccat ttaacctctc    540
tgtacctcag ttactttatc tgtatccact ttgcggtgtt gtcatgagga ttaaatcaga    600
tagcctatgt gtagcacctg gcagtgaatt tatcaccctg tactgtaact gtctactttt    660
ctgtctcctc cattggactg tcattcccag ggggttggga actgggatttt cttcatttct    720
gaggcataga agtatagcat agtggttagg agcatgactt ctggagccag agtacatggg    780
tttgaatgct accactcaca agctgtgtgg ccatggagaa gttgcctaac ctctccgtgc    840
ttcagtttca tcacccataa aatgaaggta agaatagtac ctgtatttaa aagcacctag    900
aacagttcct ggcatatagt gtcagctgtc atctctgcat ccttgtacct gtcagagagg    960
agtgtttatc aaagggggctt cttgctgcct gtttccaaac cagtcgacaa tataccaatt   1020
gctccctaac acattcttgt ttgtgcagaa ctgagctcaa tgataacatt tttatagcaa   1080
ccctgatcaa gtttcttctc ataatctctt acactttgag gccctgcag gggccctcac    1140
tctccctaat aaacattaac ctgagtaggg tgtttgagct caccatggct acattctgat   1200
gtaaagagat atatcctata cctgggccaa atgtaaacag cctggaaaag tgttaggtta   1260
aaaacaaaac aaaataaata atgaataaa tgccaggtgg ttatgagtgc tattgagaaa   1320
aatgaagcca agagggatat cagtgatgca ggtgggggta aagagcttac aacataaatg   1380
tggtgttcca tatttaaacc tcattcaaca gggaagattg gagctgaaat gtgaaggagt   1440
tgtgggagtg gaactacgtg gaaatctggg ggaaaggtgt tttgggtaaa agaaatagca   1500
agtgttgagg tccagggggca tgagtgtgct tgatatttta gggaagagta aggagaccag   1560
tataaccaga gtgagatgag actacagagg tcaggagaaa gggcatgcag accatgtggg   1620
atgctctagg acctaggcca tggtaaagat gtagggtttt accctgatgg aggtcagaag   1680
ccattggagg attctgagaa gaggagtgac aggactcgct ttatagtttt aaattataac   1740
tataaattat agttttttaaa acaatagttg cctaacctca tgttatatgt aaaactacag   1800
ttttaaaaac tataaattcc tcatactggc agcagtgtga ggggcaaggg caaaagcaga   1860
gagactaaca ggttgctggt tactcttgct agtgcaagtg aattctagaa tcttcgacaa   1920
catccagaac ttctcttgct gctgccactc aggaagaggg ttggagtagg ctaggaatag   1980
gagcacaaat taaagctcct gttcactttg acttctccat ccctctcctc ctttccttaa   2040
aggttctgat taaagcagac ttatgcccct actgctctca gaagtgaatg ggttaagttt   2100
agcagcctcc cttttgctac ttcagttctt cctgtggctg cttcccactg ataaaaagga   2160
agcaatccta tcggttactg cttagtgctg agcacatcca gtgggtaaag ttccttaaaa   2220
tgctctgcaa agaaattggg acttttcatt aaatcagaaa ttttactttt ttcccctcct   2280
```

```
gggagctaaa gatattttag agaagaatta accttttgct tctccagttg aacatttgta   2340
gcaataagtc                                                            2350

<210> SEQ ID NO 8
<211> LENGTH: 523
<212> TYPE: DNA
<213> ORGANISM: Artificial Sequence
<220> FEATURE:
<223> OTHER INFORMATION: Enhancer Short

<400> SEQUENCE: 8
ggggctcgct cgctcagtac ctggaggcga gttcctgacg cgactgcgac tcaatcctcg     60
cctggtgaag aatattttac ctatgactca ctgaaaataa agacggctga gtgaccgtgt    120
ttgttcatgt aaacattgaa caaatattta tcggcttctg cgatgtgtcc tactctttta    180
gtggaggaag acacatttta tttatgtatt taattttttct tttgaatttt acatgcgagt   240
tatacttaat aaaactcact tcaaaatata ccttcaacag aaaatccagc aacagtttct    300
attatgttag ttaaaacagc cagtcttttc ctttactttt aaaaattatt cataaatgta    360
attagtgaat gataataaac attgacatct gatccactgc tttaggagtg acacaaatga    420
agttaactca ggctattttc tttataatca ttgtgctatt gttttctttt tcttttcaat    480
tatactgctt aatataggat tttgtggcac cataggagtt gag                      523

<210> SEQ ID NO 9
<211> LENGTH: 804
<212> TYPE: DNA
<213> ORGANISM: Artificial Sequence
<220> FEATURE:
<223> OTHER INFORMATION: Enhancer Long

<400> SEQUENCE: 9
tcgccaccac ttggcttccg gcacgtgggg cagatgtttc cattcccacg gcggcagcgg     60
aagagggagg gccgggcgcg ccgcggctgc ttgcagtctc cgcaagcggc tacatcacag    120
agctcagcgt gcggtgtcac aggccccgcg gtcccgccca acagatgcac cgagatgcgc    180
gtgcgcagaa agcgtcccgg gggtgaggct ccctccctcg ctctccctct actcccgccc    240
cactctcccc cactttcccc cctccaccca ccgcggccgt cggggctcgc tcgctcagta    300
cctggaggcg agttcctgac gcgactgcga ctcaatcctc gcctggtgaa gaatattta    360 cctatgactc actgaaaata aagacggctg agtgaccgtg tttgttcatg taaacattga    420
acaaatattt atcggcttct gcgatgtgtc ctactctttt agtggaggaa gacacatttt    480
atttatgtat ttaattttttc ttttgaattt tacatgcgag ttatacttaa taaaactcac    540
ttcaaaatat accttcaaca gaaaatccag caacagtttc tattatgtta gttaaaacag    600
ccagtctttt cctttacttt taaaaattat tcataaatgt aattagtgaa tgataataaa    660
cattgacatc tgatccactg ctttaggagt gacacaaatg aagttaactc aggctatttt    720
ctttataatc attgtgctat tgttttcttt tcttttcaa ttatactgct taatatagga    780
ttttgtggca ccataggagt tgag                                            804

<210> SEQ ID NO 10
<211> LENGTH: 4429
<212> TYPE: DNA
<213> ORGANISM: Artificial Sequence
<220> FEATURE:
<223> OTHER INFORMATION: Full 5' FVIII promoter sequence
```

<400> SEQUENCE: 10

```
tcgccaccac ttggcttccg gcacgtgggg cagatgtttc cattcccacg gcggcagcgg      60
aagagggagg gccgggcgcg ccgcggctgc ttgcagtctc cgcaagcggc tacatcacag     120
agctcagcgt gcggtgtcac aggccccgcg gtcccgccca acagatgcac cgagatgcgc     180
gtgcgcagaa agcgtcccgg gggtgaggct ccctccctcg ctctccctct actcccgccc     240
cactctcccc cactttcccc cctccaccca ccgcggccgt cggggctcgc tcgctcagta     300
cctggaggcg agttcctgac gcgactgcga ctcaatcctc gcctggtgaa gaatatttta     360
cctatgactc actgaaaata aagacggctg agtgaccgtg tttgttcatg taaacattga     420
acaaatattt atcggcttct gcgatgtgtc ctactctttt agtggaggaa gacacatttt     480
atttatgtat ttaattttc ttttgaattt tacatgcgag ttatacttaa taaaactcac     540
ttcaaaatat accttcaaca gaaaatccag caacagtttc tattatgtta gttaaaacag     600
ccagtctttt cctttacttt taaaaattat tcataaatgt aattagtgaa tgataataaa     660
cattgacatc tgatccactg ctttaggagt gacacaaatg aagttaactc aggctatttt     720
ctttataatc attgtgctat tgttttcttt ttcttttcaa ttatactgct taatataagga     780
ttttgtggca ccataggagt tgagtaaaaa taaaaggaat aaaaatatac cttatctggc     840
cgggcgcggt ggctcacgcc tgtaatttca gcagtttcgg aggccgaggc gggcggatca     900
cgcggtcagg agatcgaggc catcctggct aacatggtga aaccccgtct ctactaaaaa     960
tacaaaaaat tagccgggca tggtggcggc cgcctgtagt cccagctact cgggaggctg    1020
aggcaggaga atggcgtgaa cccgggaggc ggagcttgca gtgagccgag atcgcgacac    1080
tgcactccag cctgggcgac agagtgagac tgcgtctcca aaaaaaaag aaaaaatacg    1140
ttatctatga agatttccaa tttgatttct atttatcaca aatggccaca gtactccttt    1200
gtactttacc acataccata ttgtattcag taattatttg tgaatatgta attgataata    1260
ttgtaggttt tagagaatcc ttgaaaacat gaaaatttgg taatggggtc tattttgatt    1320
atttatttat ttatttattt atttttatt tgagacagag tctcgctctt gttgcccagg    1380
ctggagtgca gtggcgcgat ctcggctcac tgcaagctcc acctcccggg ttcaagcgat    1440
tctcctgcct cagcctccca gtagctggg actacaggca cgtgccacca tgcccggcta    1500
attttttgta ttttttagtag aggaggagtt tcatcttgtt agctaggatg gtctagatct    1560
cctgacctcg tgatctgccc gcctcagcct cccaaagtgc tgggattaca ggtgtgagcc    1620
accgtgcccg gccatatttt gatttaaaat ttagcaataa tagataaaat tttcaatcaa    1680
ctaagccctt gggccaggga atgctattcc ttaaaaagtg cttctatcaa tatagcctct    1740
gactcattac tttgttaatt tttaaattgt atttcattcc tgattaacat tcccacccag    1800
attattaatt atacaatctg ttaactgtag aacctcaaac atgttggatt gtactgtatt    1860
tgtctggaag acacattttt aaaacattgt aatcgctata agagaagcac tgggaaagaa    1920
aggagcttct atgcctgcag tgcctgagga gcccttttaac agtgtgcccc gcccctaagc    1980
tactcatgca gtcatcccca tcccagttag tcaactttat tccaaaaaac ttggtgttcc    2040
aaatttttcc ttctcaaagc ccacagatcc aaaattcatc agcagttccc acaaacgtta    2100
ccctcacaat gaatccagcc attttttcacc ctctccagtg gtaccatcat agcccaagcc    2160
gccaccattt ctcaccccg gttaacaggc caccctcctt ctacccttat cctgctagag    2220
tttgttttat ctacagtgat cagaaagatc agcctaaaag ataattctga tcaccaccct    2280
cctctactca caacccggcc gtgtctcccc attgccctca gtgtagaagt caatgtccct    2340
```

```
ttgctgaaat gcaaccttag tgaaactttc catgactaac ctcctttaaa attgcaacct   2400
ggtccaccct tactccccct taccccactt ctcttttttg cacagcactt attttacctt   2460
ctaacatact gtataatgta ctcatgtatt gtaattattg cttatcatcc ctctttcagt   2520
tgcttatatt tttcatcaat gtgtacccag tgcctaggac aatatctgtc taggacaaat   2580
gggtagttat gtggctgtag gcaagccatt taacctctct gtacctcagt tactttatct   2640
gtatccactt tgcggtgttg tcatgaggat taaatcagat agcctatgtg tagcacctgg   2700
cagtgaattt atcaccctgt actgtaactg tctacttttc tgtctcctcc attggactgt   2760
cattcccagg gggttgggaa ctgggatttc ttcatttctg aggcatagaa gtatagcata   2820
gtggttagga gcatgacttc tggagccaga gtacatgggt ttgaatgcta ccactcacaa   2880
gctgtgtggc catggagaag ttgcctaacc tctccgtgct tcagtttcat cacccataaa   2940
atgaaggtaa gaatagtacc tgtatttaaa agcacctaga acagttcctg gcatatagtg   3000
tcagctgtca tctctgcatc cttgtacctg tcagagagga gtgtttatca aaggggcttc   3060
ttgctgcctg tttccaaacc agtcgacaat ataccaattg ctccctaaca cattcttgtt   3120
tgtgcagaac tgagctcaat gataacattt ttatagcaac cctgatcaag tttcttctca   3180
taatctctta cactttgagg cccctgcagg ggccctcact ctccctaata aacattaacc   3240
tgagtagggt gtttgagctc accatggcta cattctgatg taaagagata tatcctatac   3300
ctgggccaaa tgtaaacagc ctggaaaagt gttaggttaa aaacaaaaca aataaataa   3360
atgaataaat gccaggtggt tatgagtgct attgagaaaa atgaagccaa gagggatatc   3420
agtgatgcag gtgggggtaa agagcttaca acataaatgt ggtgttccat atttaaacct   3480
cattcaacag ggaagattgg agctgaaatg tgaaggagtt gtgggagtgg aactacgtgg   3540
aaatctgggg gaaaggtgtt ttgggtaaaa gaaatagcaa gtgttgaggt ccaggggcat   3600
gagtgtgctt gatattttag ggaagagtaa ggagaccagt ataaccagag tgagatgaga   3660
ctacagaggt caggagaaag ggcatgcaga ccatgtggga tgctctagga cctaggccat   3720
ggtaaagatg tagggtttta ccctgatgga ggtcagaagc cattggagga ttctgagaag   3780
aggagtgaca ggactcgctt tatagtttta aattataact ataaattata gttttaaaa   3840
caatagttgc ctaacctcat gttatatgta aaactacagt tttaaaaact ataaattcct   3900
catactggca gcagtgtgag gggcaagggc aaaagcagag agactaacag gttgctggtt   3960
actcttgcta gtgcaagtga attctagaat cttcgacaac atccagaact tctcttgctg   4020
ctgccactca ggaagagggt tggagtaggc taggaatagg agcacaaatt aaagctcctg   4080
ttcactttga cttctccatc cctctcctcc tttccttaaa ggttctgatt aaagcagact   4140
tatgccccta ctgctctcag aagtgaatgg gttaagttta gcagcctccc ttttgctact   4200
tcagttcttc ctgtggctgc ttcccactga taaaaggaa gcaatcctat cggttactgc   4260
ttagtgctga gcacatccag tgggtaaagt tccttaaaat gctctgcaaa gaaattggga   4320
cttttcatta aatcagaaat tttacttttt tcccctcctg ggagctaaag atattttaga   4380
gaagaattaa ccttttgctt ctccagttga acatttgtag caataagtc                4429

<210> SEQ ID NO 11
<211> LENGTH: 4374
<212> TYPE: DNA
<213> ORGANISM: Artificial Sequence
<220> FEATURE:
<223> OTHER INFORMATION: BDD FVIII
```

<400> SEQUENCE: 11

| | | | | | |
|---|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaaagactt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggataggggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agtttctact | gttttgtcat | atctcttccc | accaacatga | tggcatggaa | 1020 |
| gcttatgtca | agtagacag | ctgtccagag | gaacccccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctcccctt | agtcctcgcc | 1260 |
| cccgatgaca | gaagttataa | aagtcaatat | ttgaacaatg | gccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | ttactttatg | gggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaaacattt | gaaggatttt | 1560 |
| ccaattctgc | caggagaaat | attcaaatat | aaatggacag | tgactgtaga | gatgggccca | 1620 |
| actaaatcag | atcctcggtg | cctgacccgc | tattactcta | gtttcgttaa | tatggagaga | 1680 |
| gatctagctt | caggactcat | tggcccctctc | ctcatctgct | acaaagaatc | tgtagatcaa | 1740 |
| agaggaaacc | agataatgtc | agacaagagg | aatgtcatcc | tgtttttctgt | atttgatgag | 1800 |
| aaccgaagct | ggtacctcac | agagaatata | caacgctttc | tccccaatcc | agctggagtg | 1860 |
| cagcttgagg | atccagagtt | ccaagcctcc | aacatcatgc | acagcatcaa | tggctatgtt | 1920 |
| tttgatagtt | tgcagttgtc | agtttgtttg | catgaggtgg | catactggta | cattctaagc | 1980 |
| attggagcac | agactgactt | cctttctgtc | ttcttctctg | gatataccctt | caaacacaaa | 2040 |
| atggtctatg | aagacacact | caccctattc | ccattctcag | agaaactgt | cttcatgtcg | 2100 |
| atggaaaacc | caggtctatg | gattctgggg | tgccacaact | cagactttcg | gaacagaggc | 2160 |
| atgaccgcct | tactgaaggt | ttctagttgt | gacaagaaca | ctggtgatta | ttacgaggac | 2220 |
| agttatgaag | atatttcagc | atacttgctg | agtaaaaaca | atgccattga | accaagaagc | 2280 |
| ttctcccaaa | acccaccagt | cttgaaacgc | catcaacggg | aaataactcg | tactactctt | 2340 |

```
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagcaga agttgaag ataatatcat ggtaactttc     2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt ttttcaccat cttttgatgag accaaaagct ggtacttcac tgaaaatatg   3060
gaaagaaact gcagggctcc ctgcaatatc cagatggaag atcccacttt taagagaat    3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcaccgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac acttttctg    3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagcccttt cttggatcaa ggtggatctg    3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc ctccaattatt gctcgataca tccgtttgca cccaactcat   3840
tatagcattc gcagcactct tcgcatggga ttgatgggct gtgatttaaa tagttgcagc   3900
atgccattgg gaatggagag taagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga agtcacagg agtaactact cagggagtaa atctctgct taccagcatg    4140
tatgtgaagg agttcctcat ctccagcagt caagatggcc atcagtggac tctctttttt   4200
cagaatggca agtaaaggt ttttcaggga atcaagact ccttcacacc tgtggtgaac    4260
tctctagacc caccgttact gactcgctac cttcgaattc accccagag ttgggtgcac   4320
cagattgccc tgaggatgga ggttctgggc tgcgaggcac aggacctcta ctga         4374
```

<210> SEQ ID NO 12
<211> LENGTH: 442
<212> TYPE: DNA
<213> ORGANISM: Artificial Sequence
<220> FEATURE:
<223> OTHER INFORMATION: LV.pF8.8

<400> SEQUENCE: 12

```
aatcttcgac aacatccaga acttctcttg ctgctgccac tcaggaagag ggttggagta    60
ggctaggaat aggagcacaa attaaagctc ctgttcactt tgacttctcc atccctctcc   120
tcctttcctt aaaggttctg attaaagcag acttatgccc ctactgctct cagaagtgaa   180
tgggttaagt ttagcagcct cccttttgct acttcagttc ttcctgtggc tgcttcccac   240
tgataaaaag gaagcaatcc tatcggttac tgcttagtgc tgagcacatc cagtgggtaa   300
agttccttaa aatgctctgc aaagaaattg gacttttca ttaaatcaga aattttactt   360
ttttcccctc ctgggagcta agatatttt agagaagaat taaccttttg cttctccagt   420
tgaacatttg tagcaataag tc                                            442
```

<210> SEQ ID NO 13
<211> LENGTH: 4785
<212> TYPE: DNA
<213> ORGANISM: Artificial Sequence
<220> FEATURE:
<223> OTHER INFORMATION: FVIII-N6

<400> SEQUENCE: 13

```
atgcaaagtg atctcggtga gctgcctgtg gacgcaagat tcctcctag agtgccaaaa     60 tcttttccat caacacctc agtcgtgtac aaaaagactc tgtttgtaga attcacggat    120 cacctttca acatcgctaa gccaaggcca ccctggatgg gtctgctagg tcctaccatc    180
caggctgagg tttatgatac agtggtcatt acacttaaga acatggcttc ccatcctgtc    240
agtcttcatg ctgttggtgt atcctactgg aaagcttctg agggagctga atatgatgat    300
cagaccagtc aaagggagaa agaagatgat aaagtcttcc ctggtggaag ccatacatat    360
gtctggcagg tcctgaaaga gaatggtcca atggcctctg acccactgtg ccttacctac    420
tcatatcttt ctcatgtgga cctggtaaaa gacttgaatt caggcctcat tggagcccta    480
ctagtatgta gagaagggag tctggccaag gaaaagacac agaccttgca caatttata    540 ctacttttg ctgtatttga tgaagggaaa agttggcact cagaaacaaa gaactccttg    600
atgcaggata gggatgctgc atctgctcgg gcctggccta aaatgcacac agtcaatggt    660
tatgtaaaca ggtctctgcc aggtctgatt ggatgccaca ggaaatcagt ctattggcat    720
gtgattggaa tgggcaccac tcctgaagtg cactcaatat tcctcgaagg tcacacattt    780
cttgtgagga accatcgcca ggcgtccttg gaaatctcgc aataactttt ccttactgct    840
caaacactct tgatggacct ggacagtttt ctactgtctt gtcatatctc ttcccaccaa    900
catgatggca tggaagctta tgtcaaagta cacagctgtc cagaggaacc ccaactacga    960
atgaaaaata tgaagaagc ggaagactat gatgatgatc ttactgattc tgaaatggat   1020
gtggtcaggt tgatgatga caactctcct tcctttatcc aaattcgctc agttgccaag   1080
aagcatccta aaacttgggt acattacatt gctgctgaag gaggactgg gactatgct   1140 cccttagtcc tcgccccga tgacagaagt tataaaagtc aatatttgaa caatggccct   1200
cagcggattg gtaggaagta caaaaagtc cgatttatgg catacacaga tgaaaccttt   1260
aagactcgtg aagctattca gcatgaatca ggaatcttgg gacctttact ttatggggaa   1320
gttggagaca cactgttgat tatatttaag aatcaagcaa gcagaccata taacatctac   1380
cctcacggaa tcactgatgt ccgtcctttg tattcaagga gattaccaaa aggtgtaaaa   1440
catttgaagg attttccaat tctgccagga gaaatattca aatataaatg gacagtgact   1500
gtagaagatg ggccaactaa atcagatcct cggtgcctga cccgctatta ctctagtttc   1560
gttaatatgg agagagatct agcttcagga ctcattggcc ctctcctcat ctgctacaaa   1620
```

```
gaatctgtag atcaaagagg aaaccagata atgtcagaca agaggaatgt catcctgttt    1680
tctgtatttg atgagaaccg aagctggtac ctcacagaga atatacaacg ctttctcccc    1740
aatccagctg gagtgcagct tgaggatcca gagttccaag cctccaacat catgcacagc    1800
atcaatggct atgttttga tagtttgcag ttgtcagttt gtttgcatga ggtggcatac    1860
tggtacattc taagcattgg agcacagact gacttccttt ctgtcttctt ctctggatat    1920
accttcaaac acaaaatggt ctatgaagac acactcaccc tattcccatt ctcaggagaa    1980
actgtcttca tgtcgatgga aaacccaggt ctatggattc tggggtgcca caactcagac    2040
tttcggaaca gaggcatgac cgccttactg aaggtttcta gttgtgacaa gaacactggt    2100
gattattacg aggacagtta tgaagatatt tcagcatact tgctgagtaa aaacaatgcc    2160
attgaaccaa gaagcttctc ccagaattca agacaccta gcactaggca aaagcaattt    2220
aatgccacca caattccaga aaatgacata gagaagactg acccttggtt tgcacacaga    2280
acacctatgc ctaaaataca aaatgtctcc tctagtgatt tgttgatgct cttgcgacag    2340
agtcctactc cacatgggct atccttatct gatctccaag aagccaaata tgagactttt    2400
tctgatgatc catcacctgg agcaatagac agtaataaca gcctgtctga atgacacac    2460 ttcaggccac agctccatca cagtggggac atggtattta cccctgagtc aggcctccaa    2520
ttaagattaa atgagaaact ggggacaact gcagcaacag agttgaagaa acttgatttc    2580
aaagtttcta gtacatcaaa taatctgatt tcaacaattc catcagacaa tttggcagca    2640
ggtactgata atacaagttc cttaggaccc ccaagtatgc cagttcatta tgatagtcaa    2700
ttagatacca ctctatttgg caaaaagtca tctccccta ctgagtctgg tggacctctg    2760
agcttgagtg aagaaaataa tgattcaaag ttgttagaat caggtttaat gaatagccaa    2820
gaaagttcat ggggaaaaaa tgtatcgacg cgtagctttc aaaagaaaac acgacactat    2880
tttattgctg cagtggagag gctctgggat tatgggatga gtagctcccc acatgttcta    2940
agaaacaggg ctcagagtgg cagtgtccct cagttcaaga agttgttttt ccaggaattt    3000
actgatggct cctttactca gcccttatac cgtggagaac taaatgaaca tttgggactc    3060
ctggggccat atataagagc agaagttgaa gataatatca tggtaacttt cagaaatcag    3120
gcctctcgtc cctattcctt ctattctagc cttatttctt atgaggaaga tcagaggcaa    3180
ggagcagaac ctagaaaaaa cttgtcaag cctaatgaaa ccaaaactta cttttggaaa    3240
gtgcaacatc atatggcacc cactaaagat gagtttgact gcaaagcctg gcttatttc    3300 tctgatgttg acctggaaaa agatgtgcac tcaggcctga ttggacccct tctggtctgc    3360
cacactaaca cactgaaccc tgctcatggg agacaagtga cagtacagga atttgctctg    3420
tttttcacca tctttgatga gaccaaaagc tggtacttca ctgaaaatat ggaaagaaac    3480
tgcagggctc cctgcaatat ccagatggaa gatcccactt ttaaagagaa ttatcgcttc    3540
catgcaatca atggctacat aatggataca ctacctggct tagtaatggc tcaggatcaa    3600
aggattcgat ggtatctgct cagcatgggc agcaatgaaa acatccattc tattcatttc    3660
agtggacatg tgttcactgt acgaaaaaaa gaggagtata aaatggcact gtacaatctc    3720
tatccaggtg ttttttgagac agtggaaatg ttaccatcca agctggaat ttggcgggtg    3780 gaatgcctta ttggcgagca tctacatgct gggatgagca cactttttct ggtgtacagc    3840
aataagtgtc agactcccct gggaatggct tctggacaca ttagagattt tcagattaca    3900
gcttcaggac aatatggaca gtgggcccca aagctggcca gacttcatta ttccggatca    3960
```

| | |
|---|---|
| atcaatgcct ggagcaccaa ggagcccttt tcttggatca aggtggatct gttggcacca | 4020 |
| atgattattc acggcatcaa gacccagggt gcccgtcaga agttctccag cctctacatc | 4080 |
| tctcagttta tcatcatgta tagtcttgat gggaagaagt ggcagactta tcgaggaaat | 4140 |
| tccactggaa ccttaatggt cttctttggc aatgtggatt catctgggat aaaacacaat | 4200 |
| attttaacc ctccaattat tgctcgatac atccgtttgc acccaactca ttatagcatt | 4260 |
| cgcagcactc ttcgcatgga gttgatgggc tgtgatttaa atagttgcag catgccattg | 4320 |
| ggaatggaga gtaaagcaat atcagatgca cagattactg cttcatccta ctttaccaat | 4380 |
| atgtttgcca cctggtctcc ttcaaaagct cgacttcacc tccaagggag gagtaatgcc | 4440 |
| tggagacctc aggtgaataa tccaaaagag tggctgcaag tggacttcca gagacaatg | 4500 |
| aaagtcacag gagtaactac tcagggagta aatctctgc ttaccagcat gtatgtgaag | 4560 |
| gagttcctca tctccagcag tcaagatggc catcagtgga ctctcttttt tcagaatggc | 4620 |
| aaagtaaagg ttttcaggg aaatcaagac tccttcacac ctgtggtgaa ctctctagac | 4680 |
| ccaccgttac tgactcgcta ccttcgaatt cacccccaga gttgggtgca ccagattgcc | 4740 |
| ctgaggatgg aggttctggg ctgcgaggca caggacctct actga | 4785 |

<210> SEQ ID NO 14
<211> LENGTH: 4374
<212> TYPE: DNA
<213> ORGANISM: Artificial Sequence
<220> FEATURE:
<223> OTHER INFORMATION: FVIII-RH

<400> SEQUENCE: 14

| | |
|---|---|
| atgcaaatag agctctccac ctgcttcttt ctgtgccttt tgcgattctg ctttagtgcc | 60 |
| accagaagat actacctggg tgcagtggaa ctgtcatggg actatatgca agtgatctc | 120 |
| ggtgagctgc ctgtggacgc aagatttcct cctagagtgc caaaatcttt tccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tcttctcat | 540 |
| gtggacctgg taaagacttt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggataggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt ccttggaaat ctcgccaata actttcctta ctgctcaaac actcttgatg | 960 |
| gacccttgga cagtttctact gttttgtcat atctcttccc accaacatga tggcatggaa | 1020 |
| gcttatgtca agtagacag ctgtccagag gaaccccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |
| tgggtacatt acattgctgc tgaagaggag gactgggact atgctccctt agtcctcgcc | 1260 |

```
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaaa acccaccagt cttgaaacac catcaacggg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tgaccccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcaccgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg gatgagcac acttttctg    3420 gtgtacagca ataagtgtca gactcccctg gaatggcttc tggacacat tagagatttt    3480 cagattacag cttcaggaca atatggacag tgggccccaa agctggccag acttcattat    3540 tccgatcaa tcaatgcctg gagcaccaag gagcccttt cttggatcaa ggtggatctg    3600
```

```
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa atctctgct taccagcatg     4140 tatgtgaagg agttcctcat ctccagcagt caagatggcc atcagtggac tctcttttt    4200 cagaatggca agtaaaggt ttttcaggga aatcaagact ccttcacacc tgtggtgaac     4260
tctctagacc caccgttact gactcgctac cttcgaattc accccagag ttgggtgcac     4320 cagattgccc tgaggatgga ggttctgggc tgcgaggcac aggacctcta ctga          4374
```

<210> SEQ ID NO 15
<211> LENGTH: 4377
<212> TYPE: DNA
<213> ORGANISM: Artificial Sequence
<220> FEATURE:
<223> OTHER INFORMATION: CodonOptimized (CO) FVIII

<400> SEQUENCE: 15

```
atgcagatcg agctgtccac ctgctttttt ctgtgcctgc tgcggttctg cttcagcgcc      60
acccggcggt actacctggg cgccgtggag ctgtcctggg actacatgca gagcgacctg     120
ggcgagctgc ccgtggacgc ccggttcccc ccagagtgc caagagctt ccccttcaac       180 accagcgtgg tgtacaagaa aaccctgttc gtggagttca ccgaccacct gttcaatatc    240
gccaagccca ggccccctg atgggcctg ctgggcccca ccatccaggc cgaggtgtac       300
gacaccgtgg tgatcaccct gaagaacatg gccagccacc ccgtgagcct gcacgccgtg    360
ggcgtgagct actggaaggc cagcgagggc gccgagtacg acgaccagac cagccagcgg    420
gagaaagaag atgacaaggt gttccctggc ggcagccaca cctacgtgtg gcaggtgctg    480
aaagaaaacg gccccatggc ctccgacccc tgtgcctga cctacagcta cctgagccac     540
gtggacctgg tgaaggacct gaacagcggc ctgatcggcg ctctgctcgt ctgccgggag    600
ggcagcctgg ccaaagagaa acccagacc ctgcacaagt tcatcctgct gttcgccgtg     660
ttcgacgagg gcaagagctg gcacagcgag acaaagaaca gcctgatgca ggaccgggac    720
gccgcctctg ccagagcctg gcccaagatg cacaccgtga acggctacgt gaacagaagc    780
ctgcccggcc tgattggctg ccaccggaag agcgtgtact ggcacgtgat cggcatgggc    840
accacacccg aggtgcacag catctttctg gaagggcaca cctttctggt ccggaaccac    900
cggcaggcca gctggaaat cagccctatc accttcctga cgcccagac actgctgatg    960 gacctgggcc agttcctgct gttttgccac atcagctctc accagcacga cggcatggaa    1020
gcctacgtga aggtggactc ttgccccgag gaaccccagc tgcggatgaa gaacaacgag    1080
gaagccgagg actacgacga cgacctgacc gacagcgaga tggacgtggt gcggttcgac    1140
gacgacaaca gccccagctt catccagatc agaagcgtgg ccaagaagca ccccaagacc    1200
tgggtgcact atatcgccgc cgaggaagag gactgggact acgcccccct ggtgctggcc    1260
cccgacgaca gaagctacaa gagccagtac ctgaacaatg gccccagcg gatcggccgg    1320
```

```
aagtacaaga aagtgcggtt catggcctac accgacgaga cattcaagac ccggcaggcc   1380
atccagcacg agagcggcat cctgggcccc ctgctgtacg gcgaagtggg cgacacactg   1440
ctgatcatct tcaagaacca ggctagccgg ccctacaaca tctaccccca cggcatcacc   1500
gacgtgcggc ccctgtacag caggcggctg cccaagggcg tgaagcacct gaaggacttc   1560
cccatcctgc ccggcgagat cttcaagtac aagtggaccg tgaccgtgga ggacggcccc   1620
accaagagcg accccagatg cctgacccgg tactacagca gcttcgtgaa catggaacgg   1680
gacctggcct ccgggctgat cggacctctg ctgatctgct acaaagaaag cgtggaccag   1740
cggggcaacc agatcatgag cgacaagcgg aacgtgatcc tgttcagcgt gttcgatgag   1800
aaccggtcct ggtatctgac cgagaacatc cagcggtttc tgcccaaccc tgccggcgtg   1860
cagctggaag atcccgagtt ccaggccagc aacatcatgc actccatcaa tggctacgtg   1920
ttcgactctc tgcagctctc cgtgtgtctg cacgaggtgg cctactggta catcctgagc   1980
atcggcgccc agaccgactt cctgagcgtg ttcttcagcg gctacacctt caagcacaag   2040
atggtgtacg aggacaccct gaccctgttc cctttcagcg gcgagacagt gttcatgagc   2100
atggaaaacc ccggcctgtg gattctgggc tgccacaaca gcgacttccg gaaccggggc   2160
atgaccgccc tgctgaaggt gtccagctgc gacaagaaca ccggcgacta ctacgaggac   2220
agctacgagg atatcagcgc ctacctgctg tccaagaaca cgccatcga accccggagc   2280
ttcagccaga accccccgt gctgacgcgt caccagcggg agatcacccg gacaaccctg   2340
cagtccgacc aggaagagat cgattacgac gacaccatca gcgtggagat gaagaaagag   2400
gatttcgata tctacgacga ggacgagaac cagagcccca agcttcca gaagaaaacc   2460
cggcactact tcattgccgc cgtggagagg ctgtgggact acggcatgag ttctagcccc   2520
cacgtgctgc ggaaccgggc ccagagcggc agcgtgcccc agttcaagaa agtggtgttc   2580
caggaattca cagacggcag cttcacccag cctctgtata gaggcgagct gaacgagcac   2640
ctggggctgc tggggcccta catcagggcc gaagtggagg acaacatcat ggtgaccttc   2700
cggaatcagg ccagcagacc ctactccttc tacagcagcc tgatcagcta cgaagaggac   2760
cagcggcagg gcgccgaacc ccggaagaac ttcgtgaagc ccaacgaaac caagacctac   2820
ttctggaaag tgcagcacca catggccccc accaaggacg agttcgactg caaggcctgg   2880
gcctacttca gcgacgtgga tctggaaaag gacgtgcact ctggactgat tggcccactc   2940
ctggtctgcc acactaacac cctcaacccc gcccacggcc gccaggtgac cgtgcaggaa   3000
ttcgccctgt tcttcaccat cttcgacgag acaaagtcct ggtacttcac cgagaatatg   3060
gaacggaact gcagagcccc ctgcaacatc cagatggaag atcctacctt caaagagaac   3120
taccggttcc acgccatcaa cggctacatc atggacaccc tgcctggcct ggtgatggcc   3180
caggaccaga gaatccggtg gtatctgctg tccatgggca gcaacgagaa tatccacagc   3240
atccacttca gcggccacgt gttcaccgtg cggaagaaag agtacaa gatggccctg   3300
tacaacctgt accccggcgt gttcgagaca gtggagatgc tgcccagcaa ggccggcatc   3360
tggcgggtgg agtgtctgat cggcgagcac ctgcacgctg gcatgagcac cctgtttctg   3420
gtgtacagca acaagtgcca gaccccactg ggcatggcct ctggccacat ccgggacttc   3480
cagatcaccg cctccggcca gtacggccag tgggccccca gctggccag actgcactac   3540
agcggcagca tcaacgcctg gtccaccaaa gagcccttca gctggatcaa ggtggacctg   3600
ctggccccta tgatcatcca cggcattaag acccaggcg ccaggcagaa gttcagcagc   3660
```

| | |
|---|---|
| ctgtacatca gccagttcat catcatgtac agcctggacg gcaagaagtg gcagacctac | 3720 |
| cggggcaaca gcaccggcac cctgatggtg ttcttcggca atgtggacag cagcggcatc | 3780 |
| aagcacaaca tcttcaaccc ccccatcatt gcccggtaca tccggctgca ccccacccac | 3840 |
| tacagcatta gatccacact gagaatggaa ctgatgggct cgacctgaa ctcctgcagc | 3900 |
| atgcctctgg gcatggaaag caaggccatc agcgacgccc agatcacagc cagcagctac | 3960 |
| ttcaccaaca tgttcgccac ctggtccccc tccaaggcca ggctgcacct gcagggccgg | 4020 |
| tccaacgcct ggcggcctca ggtcaacaac cccaaagaat ggctgcaggt ggactttcag | 4080 |
| aaaaccatga aggtgaccgg cgtgaccacc cagggcgtga aaagcctgct gaccagcatg | 4140 |
| tacgtgaaag agtttctgat cagcagctct caggatggcc accagtggac cctgttcttt | 4200 |
| cagaacggca aggtgaaagt gttccagggc aaccaggact ccttcacccc cgtggtgaac | 4260 |
| tccctggacc ccccctgct gacccgctac ctgagaatcc accccagtc ttgggtgcac | 4320 |
| cagatcgccc tcaggatgga agtcctggga tgtgaggccc aggatctgta ctgatga | 4377 |

<210> SEQ ID NO 16
<211> LENGTH: 4377
<212> TYPE: DNA
<213> ORGANISM: Artificial Sequence
<220> FEATURE:
<223> OTHER INFORMATION: CO FVIII-RH

<400> SEQUENCE: 16

| | |
|---|---|
| atgcagatcg agctgtccac ctgcttttt ctgtgcctgc tgcggttctg cttcagcgcc | 60 |
| acccggcggt actacctggg cgccgtggag ctgtcctggg actacatgca gagcgacctg | 120 |
| ggcgagctgc ccgtggacgc ccggttcccc ccagagtgc caagagctt cccttcaac | 180 |
| accagcgtgg tgtacaagaa aaccctgttc gtggagttca ccgaccacct gttcaatatc | 240 |
| gccaagccca ggccccctg gatgggcctg ctgggcccca ccatccaggc cgaggtgtac | 300 |
| gacaccgtgg tgatcaccct gaagaacatg gccagccacc ccgtgagcct gcacgccgtg | 360 |
| ggcgtgagct actggaaggc cagcgagggc gccgagtacg acgaccagac cagccagcgg | 420 |
| gagaaagaag atgacaaggt gttccctggc ggcagccaca cctacgtgtg gcaggtgctg | 480 |
| aaagaaaacg gccccatggc ctccgacccc ctgtgcctga cctacagcta cctgagccac | 540 |
| gtggacctgg tgaaggacct gaacagcggc ctgatcggcg ctctgctcgt ctgccgggag | 600 |
| ggcagcctgg ccaaagagaa aacccagacc ctgcacaagt tcatcctgct gttcgccgtg | 660 |
| ttcgacgagg gcaagagctg gcacagcgag acaaagaaca gcctgatgca ggaccgggac | 720 |
| gccgcctctg ccagagcctg gcccaagatg cacaccgtga acggctacgt gaacagaagc | 780 |
| ctgcccggcc tgattggctg ccaccggaag agcgtgtact ggcacgtgat cggcatgggc | 840 |
| accacacccg aggtgcacag catctttctg gaagggcaca cctttctggt ccggaaccac | 900 |
| cggcaggcca gctggaaat cagccctatc accttcctga ccgcccagac actgctgatg | 960 |
| gacctgggcc agttcctgct gttttgccac atcagctctc accagcacga cggcatggaa | 1020 |
| gcctacgtga aggtggactc ttgccccgag gaaccccagc tgcggatgaa gaacaacgag | 1080 |
| gaagccgagg actacgacga cgacctgacc gacagcgaga tggacgtggt gcggttcgac | 1140 |
| gacgacaaca gcccagctt catccagatc agaagcgtgg ccaagaagca ccccaagacc | 1200 |
| tgggtgcact atatcgccgc cgaggaagag gactggact acgcccccct ggtgctggcc | 1260 |
| cccgacgaca gaagctacaa gagccagtac ctgaacaatg ccccagcg atcggccgg | 1320 |
| aagtacaaga agtgcggtt catggcctac accgacgaga cattcaagac ccgggaggcc | 1380 |

```
atccagcacg agagcggcat cctgggcccc ctgctgtacg gcgaagtggg cgacacactg    1440
ctgatcatct tcaagaacca ggctagccgg ccctacaaca tctaccccca cggcatcacc    1500
gacgtgcggc ccctgtacag caggcggctg cccaagggcg tgaagcacct gaaggacttc    1560
cccatcctgc ccggcgagat cttcaagtac aagtggaccg tgaccgtgga ggacggcccc    1620
accaagagcg accccagatg cctgacccgg tactacagca gcttcgtgaa catggaacgg    1680
gacctggcct ccgggctgat cggacctctg ctgatctgct acaaagaaag cgtggaccag    1740
cggggcaacc agatcatgag cgacaagcgg aacgtgatcc tgttcagcgt gttcgatgag    1800
aaccggtcct ggtatctgac cgagaacatc cagcggtttc tgcccaaccc tgccggcgtg    1860
cagctggaag atcccgagtt ccaggccagc aacatcatgc actccatcaa tggctacgtg    1920
ttcgactctc tgcagctctc cgtgtgtctg cacgaggtgg cctactggta catcctgagc    1980
atcggcgccc agaccgactt cctgagcgtg ttcttcagcg gctacacctt caagcacaag    2040
atggtgtacg aggacaccct gaccctgttc cctttcagcg gcgagacagt gttcatgagc    2100
atggaaaacc ccggcctgtg gattctgggc tgccacaaca gcgacttccg gaaccggggc    2160
atgaccgccc tgctgaaggt gtccagctgc gacaagaaca ccggcgacta ctacgaggac    2220
agctacgagg atatcagcgc ctacctgctg tccaagaaca cgccatcga accccggagc    2280 ttcagccaga ccccccccgt gctgacgcat caccagcggg agatcacccg gacaaccctg    2340
cagtccgacc aggaagagat cgattacgac gacaccatca gcgtggagat gaagaaagag    2400
gatttcgata tctacgacga ggacgagaac cagagcccca agcttcca aagaaaacc    2460 cggcactact tcattgccgc cgtggagagg ctgtgggact acggcatgag ttctagcccc    2520
cacgtgctgc ggaaccgggc ccagagcggc agcgtgcccc agttcaagaa agtggtgttc    2580
caggaattca cagacggcag cttcacccag cctctgtata gaggcgagct gaacgagcac    2640
ctggggctgc tggggcccta catcagggcc gaagtggagg acaacatcat ggtgaccttc    2700
cggaatcagg ccagcagacc ctactccttc tacagcagcc tgatcagcta cgaagaggac    2760
cagcggcagg cgccgaacc ccggaagaac ttcgtgaagc ccaacgaaac caagacctac    2820
ttctggaaag tgcagcacca catggccccc accaaggacg agttcgactg caaggcctgg    2880
gcctacttca gcgacgtgga tctgaaaaag gacgtgcact ctggactgat tgccccactc    2940
ctggtctgcc acactaacac cctcaacccc gcccacggcc gccaggtgac cgtgcaggaa    3000
ttcgccctgt tcttcaccat cttcgacgag acaaagtcct ggtacttcac cgagaatatg    3060
gaacggaact gcagagcccc ctgcaacatc cagatgaag atcctacctt caagagaac    3120 taccggttcc acgccatcaa cggctacatc atggacaccc tgcctggcct ggtgatggcc    3180
caggaccaga gaatccggtg gtatctgctg tccatgggca gcaacgagaa tatccacagc    3240
atccacttca gcggccacgt gttcaccgtg cggaagaaag aagagtacaa gatggcctg    3300 tacaacctgt accccggcgt gttcgagaca gtggagatgc tgcccagcaa ggccggcatc    3360
tggcgggtgg agtgtctgat cggcgagcac ctgcacgctg gcatgagcac cctgtttctg    3420
gtgtacagca caagtgcca gaccccactg ggcatggcct ctggccacat ccggacttc    3480 cagatcaccg cctccggcca gtacggccag tgggccccca gctggccag actgcactac    3540 agcggcagca tcaacgcctg gtccaccaaa gagcccttca gctggatcaa ggtggacctg    3600
ctggccccta tgatcatcca cggcattaag acccagggcg ccaggcagaa gttcagcagc    3660
ctgtacatca gccagttcat catcatgtac agcctggacg gcaagaagtg gcagacctac    3720
```

| | |
|---|---|
| cggggcaaca gcaccggcac cctgatggtg ttcttcggca atgtggacag cagcggcatc | 3780 |
| aagcacaaca tcttcaaccc ccccatcatt gcccggtaca tccggctgca ccccacccac | 3840 |
| tacagcatta gatccacact gagaatggaa ctgatgggct gcgacctgaa ctcctgcagc | 3900 |
| atgcctctgg gcatggaaag caaggccatc agcgacgccc agatcacagc cagcagctac | 3960 |
| ttcaccaaca tgttcgccac ctggtccccc tccaaggcca ggctgcacct gcagggccgg | 4020 |
| tccaacgcct ggcggcctca ggtcaacaac cccaaagaat ggctgcaggt ggactttcag | 4080 |
| aaaaccatga aggtgaccgg cgtgaccacc cagggcgtga aaagcctgct gaccagcatg | 4140 |
| tacgtgaaag agtttctgat cagcagctct caggatggcc accagtggac cctgttcttt | 4200 |
| cagaacggca aggtgaaagt gttccagggc aaccaggact ccttcacccc cgtggtgaac | 4260 |
| tccctggacc cccccctgct gacccgctac ctgagaatcc accccagtc ttgggtgcac | 4320 |
| cagatcgccc tcaggatgga agtcctggga tgtgaggccc aggatctgta ctgatga | 4377 |

<210> SEQ ID NO 17
<211> LENGTH: 1272
<212> TYPE: DNA
<213> ORGANISM: Artificial Sequence
<220> FEATURE:
<223> OTHER INFORMATION: FIX

<400> SEQUENCE: 17

| | |
|---|---|
| atgcagcgcg tgaacatgat catggcagaa tcaccaggcc tcatcaccat ctgcctttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt ttggaagcag tatgttgatg taacatgtaa cattaagaat | 300 |
| ggcagatgcg agcagttttg taaaaatagt gctgataaca aggtggtttg ctcctgtact | 360 |
| gagggatatc gacttgcaga aaaccagaag tcctgtgaac cagcagtgcc atttccatgt | 420 |
| ggaagagttt ctgtttcaca aacttctaag ctcacccgtg ctgagactgt ttttcctgat | 480 |
| gtggactatg taaattctac tgaagctgaa accatttggg ataacatcac tcaaagcacc | 540 |
| caatcattta tgacttcac tcgggttgtt ggtggagaag atgccaaacc aggtcaattc | 600 |
| ccttggcagg ttgttttgaa tggtaaagtt gatgcattct gtggaggctc tatcgttaat | 660 |
| gaaaaatgga ttgtaactgc tgcccactgt gttgaaactg gtgttaaaat tacagttgtc | 720 |
| gcaggtgaac ataatattga ggagacagaa catacagagc aaaagcgaaa tgtgattcga | 780 |
| attattcctc accacaacta caatgcagct attaataagt acaaccatga cattgccctt | 840 |
| ctggaactgg acgaaccctt agtgctaaac agctacgtta cacctatttg cattgctgac | 900 |
| aaggaataca cgaacatctt cctcaaattt ggatctggct atgtaagtgg ctggggaaga | 960 |
| gtcttccaca aagggagatc agctttagtt cttcagtacc ttagagttcc acttgttgac | 1020 |
| cgagccacat gtcttcgatc tacaaagttc accatctata caacatgtt ctgtgctggc | 1080 |
| ttccatgaag gaggtagaga ttcatgtcaa ggagatagtg ggggacccca tgttactgaa | 1140 |
| gtggaaggga ccagtttctt aactggaatt attagctggg gtgaagagtg tgcaatgaaa | 1200 |
| ggcaaatatg gaatatatac caaggtatcc cggtatgtca actggattaa ggaaaaaaca | 1260 |
| aagctcactt aa | 1272 |

<210> SEQ ID NO 18
<211> LENGTH: 1401

| | |
|---|---|
| <212> TYPE: DNA | |
| <213> ORGANISM: Artificial Sequence | |
| <220> FEATURE: | |
| <223> OTHER INFORMATION: FVII | |

<400> SEQUENCE: 18

| | |
|---|---|
| atggtctccc aggccctcag gctcctctgc cttctgcttg ggcttcaggg ctgcctggct | 60 |
| gcaggcgggg tcgctaaggc ctcaggagga gaaacacggg acatgccgtg aagccgggg | 120 |
| cctcacagag tcttcgtaac ccaggaggaa gcccacggcg tcctgcaccg cgccggcgc | 180 |
| gccaacgcgt tcctggagga gctgcggccg ggctccctgg agagggagtg caaggaggag | 240 |
| cagtgctcct tcgaggaggc ccgggagatc ttcaaggacg cggagaggac gaagctgttc | 300 |
| tggatttctt acagtgatgg ggaccagtgt gcctcaagtc catgccagaa tgggggctcc | 360 |
| tgcaaggacc agctccagtc ctatatctgc ttctgcctcc ctgccttcga gggccggaac | 420 |
| tgtgagacgc acaaggatga ccagctgatc tgtgtgaacg agaacggcgg ctgtgagcag | 480 |
| tactgcagtg accacacggg caccaagcgc tcctgtcggt gccacgaggg gtactctctg | 540 |
| ctggcagacg gggtgtcctg cacacccaca gttgaatatc catgtggaaa atacctatt | 600 |
| ctagaaaaaa gaaatgccag caaaccccaa ggccgaattg tgggggggcaa ggtgtgcccc | 660 |
| aaaggggagt gtccatggca ggtcctgttg ttggtgaatg gagctcagtt gtgtggggggg | 720 |
| accctgatca acaccatctg ggtggtctcc gcggcccact gtttcgacaa aatcaagaac | 780 |
| tggaggaacc tgatcgcggt gctgggcgag cacgacctca gcgagcacga cggggatgag | 840 |
| cagagccggc gggtggcgca ggtcatcatc cccagcacgt acgtcccggg caccaccaac | 900 |
| cacgacatcg cgctgctccg cctgcaccag cccgtggtcc tcactgacca tgtggtgccc | 960 |
| ctctgcctgc ccgaacggac gttctctgag aggacgctgg ccttcgtgcg cttctcattg | 1020 |
| gtcagcggct ggggccagct gctggaccgt ggcgccacgg ccctggagct catggtcctc | 1080 |
| aacgtgcccc ggctgatgac ccaggactgc ctgcagcagt cacggaaggt gggagactcc | 1140 |
| ccaaatatca cggagtacat gttctgtgcc ggctactcgg atggcagcaa ggactcctgc | 1200 |
| aaggggdaca gtggaggccc acatgccacc cactaccggg gcacgtggta cctgacgggc | 1260 |
| atcgtcagct ggggccaggg ctgcgcaacc gtgggccact tggggtgta caccagggtc | 1320 |
| tcccagtaca tcgagtggct gcaaaagctc atgcgctcag agccacgccc aggagtcctc | 1380 |
| ctgcgagccc catttcccta g | 1401 |

| | |
|---|---|
| <210> SEQ ID NO 19 | |
| <211> LENGTH: 6675 | |
| <212> TYPE: DNA | |
| <213> ORGANISM: Artificial Sequence | |
| <220> FEATURE: | |
| <223> OTHER INFORMATION: FV | |

<400> SEQUENCE: 19

| | |
|---|---|
| atgttcccag ctgcccacg cctctgggtc ctggtggtct tgggcaccag ctgggtaggc | 60 |
| tgggggagcc aagggacaga agcggcacag ctaaggcagt tctacgtggc tgctcagggc | 120 |
| atcagttgga gctaccgacc tgagcccaca aactcaagtt tgaatctttc tgtaacttcc | 180 |
| tttaagaaaa ttgtctacag agagtatgaa ccatatttta gaaagaaaaa accacaatct | 240 |
| accatttcag gacttcttgg gcctacttta tatgctgaag tcggagacat cataaaagtt | 300 |
| cactttaaaa ataaggcaga taagcccttg agcatccatc ctcaaggaat taggtacagt | 360 |
| aaattatcag aaggtgcttc ttaccttgac cacacattcc ctgcggagaa gatggacgac | 420 |

```
gctgtggctc caggccgaga atacacctat gaatggagta tcagtgagga cagtggaccc    480
acccatgatg accctccatg cctcacacac atctattact cccatgaaaa tctgatcgag    540
gatttcaact cggggctgat tgggcccctg cttatctgta aaaagggac cctaactgag    600 ggtgggacac agaagacgtt tgacaagcaa atcgtgctac tatttgctgt gtttgatgaa    660
agcaagagct ggagccagtc atcatcccta atgtacacag tcaatggata tgtgaatggg    720
acaatgccag atataacagt ttgtgcccat gaccacatca gctggcatct gctgggaatg    780
agctcggggc cagaattatt ctccattcat ttcaacggcc aggtcctgga gcagaaccat    840
cataaggtct cagccatcac ccttgtcagt gctacatcca ctaccgcaaa tatgactgtg    900
ggcccagagg gaaagtggat catatcttct ctcaccccaa acatttgca agctgggatg    960 caggcttaca ttgacattaa aaactgccca agaaaaccaa ggaatcttaa gaaaataact    1020
cgtgagcaga ggcggcacat gaagaggtgg gaatacttca ttgctgcaga ggaagtcatt    1080
tgggactatg cacctgtaat accagcgaat atggacaaaa aatacaggtc tcagcatttg    1140
gataatttct caaaccaaat tggaaaacat tataagaaag ttatgtacac acagtacgaa    1200
gatgagtcct tcaccaaaca tacagtgaat cccaatatga agaagatgg gattttgggt    1260 cctattatca gagcccaggt cagagacaca ctcaaaatcg tgttcaaaaa tatggccagc    1320 cgccctata gcatttaccc tcatggagtg accttctcgc cttatgaaga tgaagtcaac    1380
tcttctttca cctcaggcag gaacaacacc atgatcagag cagttcaacc aggggaaacc    1440
tatacttata agtggaacat cttagagttt gatgaaccca cagaaaatga tgcccagtgc    1500
ttaacaagac catactacag tgacgtggac atcatgagag acatcgcctc tgggctaata    1560
ggactacttc taatctgtaa gagcagatcc ctggacaggc gaggaataca gagggcagca    1620
gacatcgaac agcaggctgt gtttgctgtg tttgatgaga caaaagctg gtaccttgag    1680 gacaacatca acaagttttg tgaaaatcct gatgaggtga acgtgatga ccccaagttt    1740 tatgaatcaa acatcatgag cactatcaat ggctatgtgc ctgagagcat aactactctt    1800
ggattctgct ttgatgacac tgtccagtgg cacttctgta gtgtgggac ccagaatgaa    1860 attttgacca tccacttcac tgggcactca ttcatctatg aaagaggca tgaggacacc    1920 ttgaccctct tccccatgcg tggagaatct gtgacggtca caatggataa tgttggaact    1980
tggatgttaa cttccatgaa ttctagtcca agaagcaaaa agctgaggct gaaattcagg    2040
gatgttaaat gtatcccaga tgatgatgaa gactcatatg agattttttga acctccagaa    2100 tctacagtca tggctacacg gaaaatgcat gatcgtttag aacctgaaga tgaagagagt    2160
gatgctgact atgattacca gaacagactg gctgcagcat taggaatcag gtcattccga    2220
aactcatcat tgaatcagga agaagaagag ttcaatctta ctgccctagc tctggagaat    2280
ggcactgaat tcgtttcttc aaacacagat ataattgttg gttcaaatta ttcttcccca    2340
agtaatatta gtaagttcac tgtcaataac cttgcagaac ctcagaaagc cccttctcac    2400
caacaagcca ccacagctgg ttccccactg agacacctca ttggcaagaa ctcagttctc    2460
aattcttcca cagcagagca ttccagccca tattctgaag accctataga ggatcctcta    2520
cagccagatg tcagggggat acgtctactt cacttggtg ctggagaatt caaaagtcaa    2580
gaacatgcta agcataaggg acccaaggta gaaagagatc aagcagcaaa gcacaggttc    2640
tcctggatga aattactagc acataaagtt gggagacacc taagccaaga cactggttct    2700
ccttccggaa tgaggccctg ggaggacctt cctagccaag acactggttc tccttccaga    2760
atgaggccct ggaaggaccc tcctagtgat ctgttactct aaaaacaaag taactcatct    2820
```

```
aagattttgg ttgggagatg gcatttggct tctgagaaag gtagctatga aataatccaa    2880
gatactgatg aagacacagc tgttaacaat tggctgatca gccccagaa tgcctcacgt     2940 gcttggggag aaagcacccc tcttgccaac aagcctggaa agcagagtgg ccacccaaag    3000
tttcctagag ttagacataa atctctacaa gtaagacagg atggaggaaa gagtagactg    3060
aagaaaagcc agtttctcat taagacacga aaaagaaaa aagagaagca cacacaccat    3120
gctcctttat ctccgaggac cttcacccct taagaagtg aagcctacaa cacattttca    3180
gaaagaagac ttaagcattc gttggtgctt cataaatcca atgaaacatc tcttcccaca    3240
gacctcaatc agacattgcc ctctatggat tttggctgga tagcctcact tcctgaccat    3300
aatcagaatt cctcaaatga cactggtcag gcaagctgtc ctccaggtct ttatcagaca    3360
gtgcccccag aggaacacta tcaaacattc cccattcaag accctgatca aatgcactct    3420
acttcagacc ccagtcacag atcctcttct ccagagctca gtgaaatgct tgagtatgac    3480
cgaagtcaca agtccttccc cacagatata agtcaaatgt cccctcctc agaacatgaa    3540 gtctggcaga cagtcatctc tccagacctc agccaggtga ccctctctcc agaactcagc    3600
cagacaaacc tctctccaga cctcagccac acgactctct ctccagaact cattcagaga    3660
aacctttccc cagccctcgg tcagatgccc atttctccag acctcagcca tacaaccctt    3720
tctccagacc tcagccatac aaccctttct tagacctca gccagacaaa cctctctcca    3780
gaactcagtc agacaaacct ttctccagcc ctcggtcaga tgccccttc tccagacctc    3840 agccatacaa cccttctct agacttcagc cagacaaacc tctctccaga actcagccat    3900
atgactctct ctccagaact cagtcagaca aacctttccc cagccctcgg tcagatgccc    3960
atttctccag acctcagcca tacaacccct tctctagact tcagccagac aaacctctct    4020
ccagaactca gtcaaacaaa cctttcccca gccctcggtc agatgcccct ttctccagac    4080
cccagccata caacccttc tctagacctc agccagacaa acctctctcc agaactcagt    4140
cagacaaacc tttccccaga cctcagtgag atgcccctct ttgcagatct cagtcaaatt    4200 cccccttaccc cagacctcga ccagatgaca ctttctccag accttggtga gacagatctt    4260
tccccaaact ttggtcagat gtccctttcc ccagacctca gccaggtgac tctctctcca    4320
gacatcagtg acaccaccct tctcccggat ctcagccaga tatcacctcc tccagacctt    4380
gatcagatat tctaccctcc tgaatctagt cagtcattgc ttcttcaaga atttaatgag    4440 tctttcctt atccagacct tggtcagatg ccatctcctt catctcctac tctcaatgat    4500
acttttctat caaaggaatt taatccactg gttatagtgg gcctcagtaa agatggtaca    4560
gattacattg agatcattcc aaaggaagag gtccagagca gtgaagatga ctatgctgaa    4620
attgattatg tgccctatga tgaccctac aaaactgatg ttaggacaaa catcaactcc    4680
tccagagatc ctgacaacat tgcagcatgg tacctccgca gcaacaatgg aaacagaaga    4740
aattattaca ttgctgctga agaaatatcc tgggattatt cagaatttgt acaaagggaa    4800
acagatattg aagactctga tgatattcca gaagatacca catataagaa agtagttttt    4860
cgaaagtacc tcgacagcac ttttaccaaa cgtgatcctc gagggagta tgaagagcat    4920 ctcggaattc ttggtcctat tatcagagct gaagtggatt atgttatcca agttcgtttt    4980 aaaatttag catccagacc gtattctcta catgcccatg actttccta tgaaaaatca    5040 tcagagggaa agacttatga agatgactct cctgaatggt ttaaggaaga taatgctgtt    5100
cagccaaata gcagttatac ctacgtatgg catgccactg agcgatcagg gccagaaagt    5160
```

| | |
|---|---|
| cctggctctg cctgtcgggc ttgggcctac tactcagctg tgaacccaga aaagatatt | 5220 |
| cactcaggct tgataggtcc cctcctaatc tgccaaaaag gaatactaca taaggacagc | 5280 |
| aacatgccta tggacatgag agaatttgtc ttactattta tgacctttga tgaaaagaag | 5340 |
| agctggtact atgaaaagaa gtcccgaagt tcttggagac tcacatcctc agaaatgaaa | 5400 |
| aaatcccatg agtttcacgc cattaatggg atgatctaca gcttgctgg cctgaaaatg | 5460 |
| tatgagcaag agtgggtgag gttacacctg ctgaacatag gcggctccca agacattcac | 5520 |
| gtggttcact ttcacggcca gaccttgctg gaaaatggca ataaacagca ccagttaggg | 5580 |
| gtctggcccc ttctgcctgg ttcatttaaa actcttgaaa tgaaggcatc aaaacctggc | 5640 |
| tggtggctcc taaacacaga ggttggagaa accagagag cagggatgca aacgccattt | 5700 |
| cttatcatgg acagagactg taggatgcca atgggactaa gcactggtat catatctgat | 5760 |
| tcacagatca aggcttcaga gtttctgggt tactgggagc ccagattagc aagattaaac | 5820 |
| aatggtggat cttataatgc ttggagtgta gaaaaacttg cagcagaatt tgcctctaaa | 5880 |
| ccttggatcc aggtggacat gcaaaaggaa gtcataatca cagggatcca gacccaaggt | 5940 |
| gccaaacact acctgaagtc ctgctatacc acagagttct atgtagctta cagttccaac | 6000 |
| cagatcaact ggcagatctt caaagggaac agcacaagga atgtgatgta ttttaatggc | 6060 |
| aattcagatg cctctacaat aaaagagaat cagtttgacc cacctattgt ggctagatat | 6120 |
| attaggatct ctccaactcg agcctataac agacctaccc ttcgattgga actgcaaggt | 6180 |
| tgtgaggtaa atggatgttc cacacccctg ggtatggaaa atggaaagat agaaaacaag | 6240 |
| caaatcacag cttcttcgtt taagaaatct tggtggggag attactggga acccttccgt | 6300 |
| gcccgtctga atgcccaggg acgtgtgaat gcctggcaag ccaaggcaaa caacaataag | 6360 |
| cagtggctag aaattgatct actcaagatc aagaagataa cggcaattat aacacagggc | 6420 |
| tgcaagtctc tgtcctctga aatgtatgta aagagctata ccatccacta cagtgagcag | 6480 |
| ggagtggaat ggaaaccata caggctgaaa tcctccatgg tggacaagat ttttgaagga | 6540 |
| aatactaata ccaaaggaca tgtgaagaac ttttttcaacc ccccaatcat ttccaggttt | 6600 |
| atccgtgtca ttcctaaaac atggaatcaa agtattgcac ttcgcctgga actctttggc | 6660 |
| tgtgatattt actag | 6675 |

<210> SEQ ID NO 20
<211> LENGTH: 1272
<212> TYPE: DNA
<213> ORGANISM: Artificial Sequence
<220> FEATURE:
<223> OTHER INFORMATION: FIX-Padua

<400> SEQUENCE: 20

| | |
|---|---|
| atgcagcgcg tgaacatgat catggcagaa tcaccaggcc tcatcaccat ctgccttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca gggaaccctt | 180 |
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ggcagatgcg agcagttttg taaaaatagt gctgataaca aggtggtttg ctcctgtact | 360 |
| gagggatatc gacttgcaga aaaccagaag tcctgtgaac cagcagtgcc atttccatgt | 420 |
| ggaagagttt ctgtttcaca aacttctaag ctcacccgtg ctgagactgt tttcctgat | 480 |
| gtggactatg taaattctac tgaagctgaa accatttttgg ataacatcac tcaaagcacc | 540 |

```
caatcattta atgacttcac tcgggttgtt ggtggagaag atgccaaacc aggtcaattc    600
ccttggcagg ttgttttgaa tggtaaagtt gatgcattct gtggaggctc tatcgttaat    660
gaaaaatgga ttgtaactgc tgcccactgt gttgaaactg gtgttaaaat tacagttgtc    720
gcaggtgaac ataatattga ggagacagaa catacagagc aaaagcgaaa tgtgattcga    780
attattcctc accacaacta caatgcagct attaataagt acaaccatga cattgccctt    840
ctggaactgg acgaacccct tagtgctaaa cagctacgtta cacctatttg cattgctgac    900
aaggaataca cgaacatctt cctcaaattt ggatctggct atgtaagtgg ctggggaaga    960
gtcttccaca aagggagatc agctttagtt cttcagtacc ttagagttcc acgagttgac   1020
cgagccacat gtcttcgatc tacaaagttc accatctata acaacatgtt ctgtgctggc   1080
ttccatgaag gaggtagaga ttcatgtcaa ggagatagtg ggggacccca tgttactgaa   1140
gtggaaggga ccagtttctt aactggaatt attagctggg gtgaagagtg tgcaatgaaa   1200
ggcaaatatg gaatatatac caaggtatcc cggtatgtca actggattaa ggaaaaaaca   1260
aagctcactt aa                                                      1272
```

<210> SEQ ID NO 21
<211> LENGTH: 34
<212> TYPE: DNA
<213> ORGANISM: Artificial Sequence
<220> FEATURE:
<223> OTHER INFORMATION: pF8_short_XhoI_FOR

<400> SEQUENCE: 21
cagcctcgag gagctcacca tggctacatt ctga                              34

<210> SEQ ID NO 22
<211> LENGTH: 33
<212> TYPE: DNA
<213> ORGANISM: Artificial Sequence
<220> FEATURE:
<223> OTHER INFORMATION: pF8_AgeI_REV

<400> SEQUENCE: 22
cgaaccggtg acttattgct acaaatgttc aac                               33

<210> SEQ ID NO 23
<211> LENGTH: 36
<212> TYPE: DNA
<213> ORGANISM: Artificial Sequence
<220> FEATURE:
<223> OTHER INFORMATION: pF8_ECL_XhoI_FOR

<400> SEQUENCE: 23
cagcctcgag gtttttaaaa caatagttgc ctaacc                            36

<210> SEQ ID NO 24
<211> LENGTH: 33
<212> TYPE: DNA
<213> ORGANISM: Artificial Sequence
<220> FEATURE:
<223> OTHER INFORMATION: pF8_AgeI_REV

<400> SEQUENCE: 24
cgaaccggtg acttattgct acaaatgttc aac                               33

<210> SEQ ID NO 25
<211> LENGTH: 29
<212> TYPE: DNA

```
<213> ORGANISM: Artificial Sequence
<220> FEATURE:
<223> OTHER INFORMATION: pF8_enhancer_Short_MfeI_FOR

<400> SEQUENCE: 25
cttcaattgg gggctcgctc gctcagtac                                29

<210> SEQ ID NO 26
<211> LENGTH: 29
<212> TYPE: DNA
<213> ORGANISM: Artificial Sequence
<220> FEATURE:
<223> OTHER INFORMATION: pF8_enhancer_MfeI_REV

<400> SEQUENCE: 26
cttcaattgc tcaactccta tggtgccac                                29

<210> SEQ ID NO 27
<211> LENGTH: 29
<212> TYPE: DNA
<213> ORGANISM: Artificial Sequence
<220> FEATURE:
<223> OTHER INFORMATION: pF8_enhancer_Long_MfeI_FOR

<400> SEQUENCE: 27
cttcaattgt cgccaccact tggcttccg                                29

<210> SEQ ID NO 28
<211> LENGTH: 33
<212> TYPE: DNA
<213> ORGANISM: Artificial Sequence
<220> FEATURE:
<223> OTHER INFORMATION: pF8_Long_XhoI_FOR

<400> SEQUENCE: 28
cagcctcgac gacgagttcc cacaaacgtt acc                           33

<210> SEQ ID NO 29
<211> LENGTH: 19
<212> TYPE: DNA
<213> ORGANISM: Artificial Sequence
<220> FEATURE:
<223> OTHER INFORMATION: DENV RF2_FOR

<400> SEQUENCE: 29
gacccacctc ccaaccccg                                           19

<210> SEQ ID NO 30
<211> LENGTH: 22
<212> TYPE: DNA
<213> ORGANISM: Artificial Sequence
<220> FEATURE:
<223> OTHER INFORMATION: GFP_REV

<400> SEQUENCE: 30
cgtcgccgtc cagctcgacc ag                                       22
```

PROMOTER FOR CELL-SPECIFIC GENE EXPRESSION AND USES THEREOF

This application is a U.S. national stage of PCT/IB2017/053460 filed on 12 Jun. 2017 which claims priority to and the benefit of Italian Application No. 102016000059985 filed on 10 Jun. 2016, the content of which are incorporated herein by reference in their entireties.

The present invention refers to nucleotide sequences used for driving the expression of a therapeutic gene, preferably FVIII and/or its variants specifically in endothelial cells and/or hematopoietic, preferably myeloid cells.

The sequences are useful for gene and/or cell therapy, preferably for treating hemophilia, more preferably type A hemophilia.

BACKGROUND

Hemophilia A (HA) is a recessive X-linked bleeding disorder that occurs in 1:5000 male new births and is due to the lack or reduced activity of coagulation Factor VIII (FVIII).

Based on the residual FVIII activity, there are three forms of hemophilia A: 1) the severe form characterized by levels of FVIII below 1%; 2) the moderate form characterized by levels of FVIII between 1 and 5%; and 3) the mild form showing from 5 to 40% of FVIII activity.

The clinical manifestations of the disease range from spontaneous bleeding, with frequent haemarthroses in the most severe form, to secondary bleeding with rare haemarthroses in milder form.

Although the development of blood products and the availability of recombinant FVIII have drastically improved the patient's quality of life, the replacement therapy does not represent yet a definitive cure and several issues are still to be solved. Among these, there are the high costs, the frequent number of administrations due to the short FVIII half-life in the bloodstream, and the high probability to develop neutralizing antibodies.

Thus, further therapeutic approaches are still required.

Since orthotopic liver transplantation corrected hemophilia A, liver has been considered the primary site of FVIII production. However, the identity of liver cells expressing FVIII is controversial and therefore still a question to be definitively clarified.

Hemophilia A represent an ideal target for gene therapy since restoring FVIII levels higher than 1% is sufficient to ameliorate the bleeding phenotypes of patients with an overall increase of quality of life. Hemophilia B gene therapy has provided good results in clinical trials by using adeno associated-viral vector (AAV) to deliver FIX into the patients.

Despite the relevant results obtained for hemophilia B, gene therapy for hemophilia A has seen significantly less progress into the clinic due to several aspects that complicates FVIII compared to FIX expression.

FVIII is naturally 5-6 fold more immunogenic than FIX. Therefore, the transgene-mediated immune response represents the main big concern.

Restricting FVIII expression to specific cell type allows to overcome inhibitor's development.

Up to day, liver, and in particular, hepatocytes, are the preferred target for hemophilia A gene therapy. Indeed, they show a limited transgene mediated immune response.

Nevertheless, the anti-FVIII antibodies development is still a current drawback for the feasibility of hemophilia A gene therapy.

In view of these considerations, there is still a huge need to develop a new gene therapy strategy to cure hemophilia, preferably type A hemophilia. In particular, there is still a need to develop a system for targeting FVIII or its variants by gene therapy free of side effects, in particular free of the transgene immune response drawbacks and the related anti-FVIII antibodies generation.

At this regard, encouraging results in mice were obtained by restricting FVIII expression to platelets by using the megakaryocytic specific promoters.

The present invention refers to the use of nucleotide sequences for targeting (driving, inducing) the expression of a therapeutic gene, such as FVIII and/or its variants/fragments specifically in endothelial cells and/or hematopoietic, preferably myeloid cells.

The inventors found for the first time that the disclosed sequences can be used as promoter sequences for inducing the gene expression specifically in endothelial cells and/or in hematopoietic, preferably myeloid cells. In particular, it is possible to induce endothelial/hematopoietic-specific (restricted) expression of FVIII and/or its variants/fragments. The endothelial expression is specific of the liver, instead the hematopoietic, preferably myeloid expression, is specific of the spleen and bone marrow (BM). This expression is able to rescue a disease such as hemophilia, preferably hemophilia A. Therefore, these sequences are useful for treating hemophilia, preferably type A hemophilia, preferably by gene and/or cell therapy by introducing these sequences into an expression vector and/or into cells.

Advantageously, the inventors found that the endothelial/hematopoietic-specific expression of FVIII and/or its variants/fragments induced by these sequences does not cause anti-FVIII antibodies generation, meaning that there is no immune response against FVIII when it is expressed in these cells under the nucleotide sequences here disclosed. This is true also when the disclosed sequences are used as promoter sequences to induce the endothelial/hematopoietic specific expression of FVIII in subjects having systemic anti-FVIII antibodies (an immune response against FVIII). Indeed, in this condition the inventors have surprisingly found that 1) FVIII is expressed at therapeutic levels (more than 6%) for long time (more than 1 year) and, above all, 2) the already present immune response is repressed overtime, meaning that anti-FVIII antibodies titers decreased after the treatments.

DEFINITIONS

In the context of the present invention promoter means a DNA sequence adjacent and typically upstream (5') of the sense strand of the regulated gene, where transcription of a gene by RNA polymerase begins.

In the context of the present invention hemophilia A means a X-linked genetic disorder caused by missing or defective clotting FVIII. In this context the FVIII mRNA sequence corresponds to the sequence with the NCBI accession number NM_000132.3 while the corresponding Coding Sequence (CDS from now on) has NCBI accession number CCDS35457.1.

In the context of the present invention, further diseases or conditions associated with or related to FVIII gene misexpression mean disease such as hemophilia B, that is a X-linked genetic disorder caused by missing or defective clotting FIX.

In the context of the present invention gene therapy means a set of strategies that modify the expression of an individual's genes or that correct abnormal genes. Each strategy involves the administration of a specific DNA.

In the context of the present invention coagulation cascade means the sequence of biochemical reactions, involving clotting factors that stop bleeding by forming the fibrin clot.

In the context of the present invention, liver sinusoidal endothelial cells mean the cells that form a continuous lining of the liver sinusoids, separating parenchymal cells and fat-storing cells from sinusoidal blood.

In this context, enhancer means a short region of DNA that can increase transcription of genes and can be located upstream of a gene, within the coding region of the gene, downstream of a gene, or thousands of nucleotides away.

DRAWINGS

FIG. 1 shows a schematic representation of disclosed sequences along the full length (−4429) FVIII promoter, wherein $a_0$ region extends from 0 to −442 bp; a region extends from 0 to −599 bp; b region is from −599 to −1175; c region is from −1175 and −2350; d region is from −2489 and −2745; e region (short enhancer) is from −3625 and −4184; and f region (long enhancer) is from −3625 and −4429.

Figure 2:
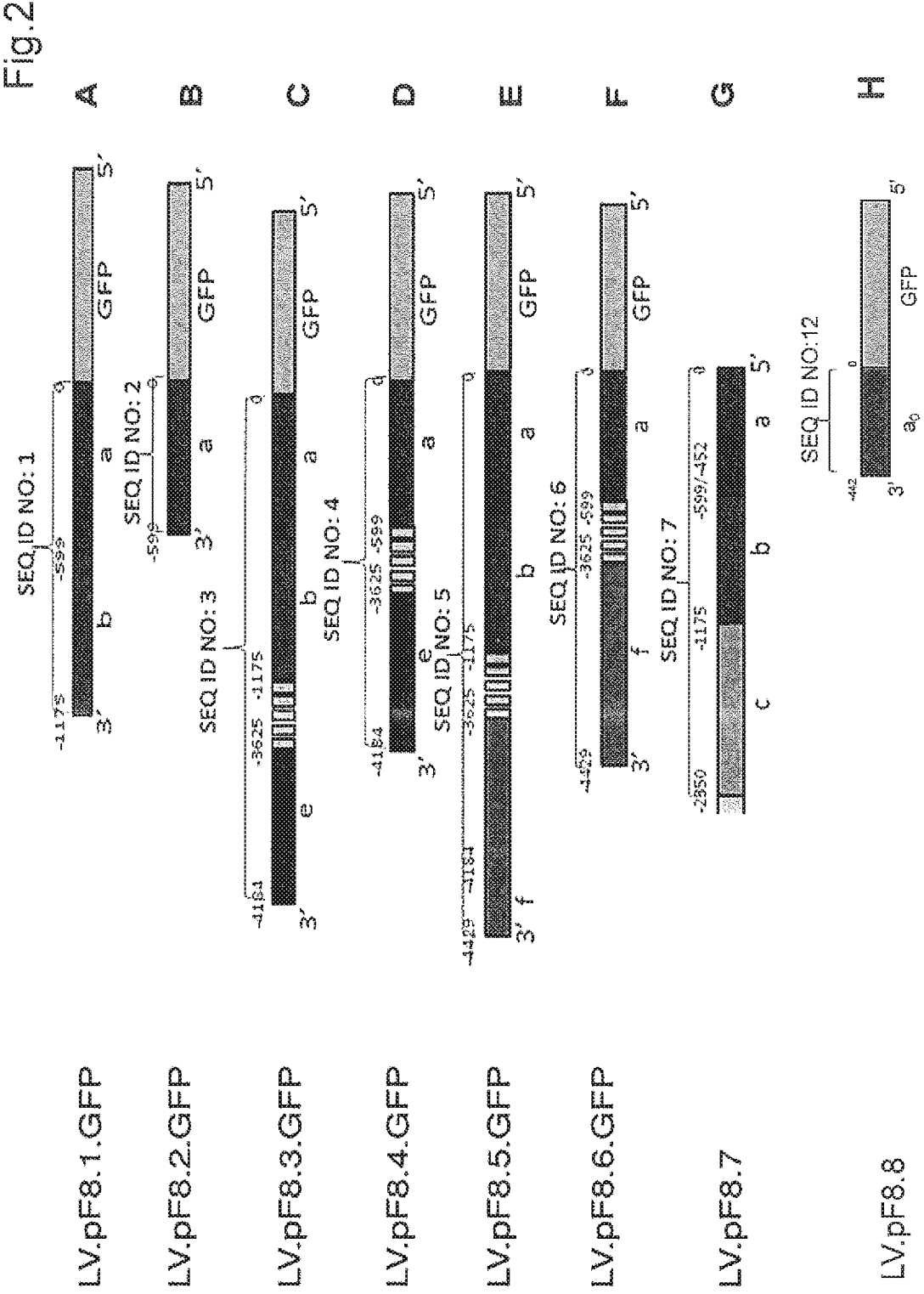

FIG. 2 shows a schematic representation of sequences of the FVIII promoter disclosed in the present invention. In particular, the FVIII promoter sequences of interest are at the head of GFP marker gene as an example. However, the authors have developed also constructs having luciferase as marker gene instead of GFP.

LV. pF8.1 comprises the regions a and b of FVIII promoter.

LV. pF8.2 comprises the region a of FVIII promoter.

LV. pF8.3 comprises the regions a, b and e of FVIII promoter.

LV. pF8.4 comprises the regions a and e of FVIII promoter.

LV. pF8.5 comprises the regions a, b and f of FVIII promoter.

LV. pF8.6 comprises the regions a and f of FVIII promoter.

LV. pF8.7 comprises the regions a, b and c of FVIII promoter.

LV. pF8.8 comprises the regions $a_0$ of FVIII promoter

Figure 3:
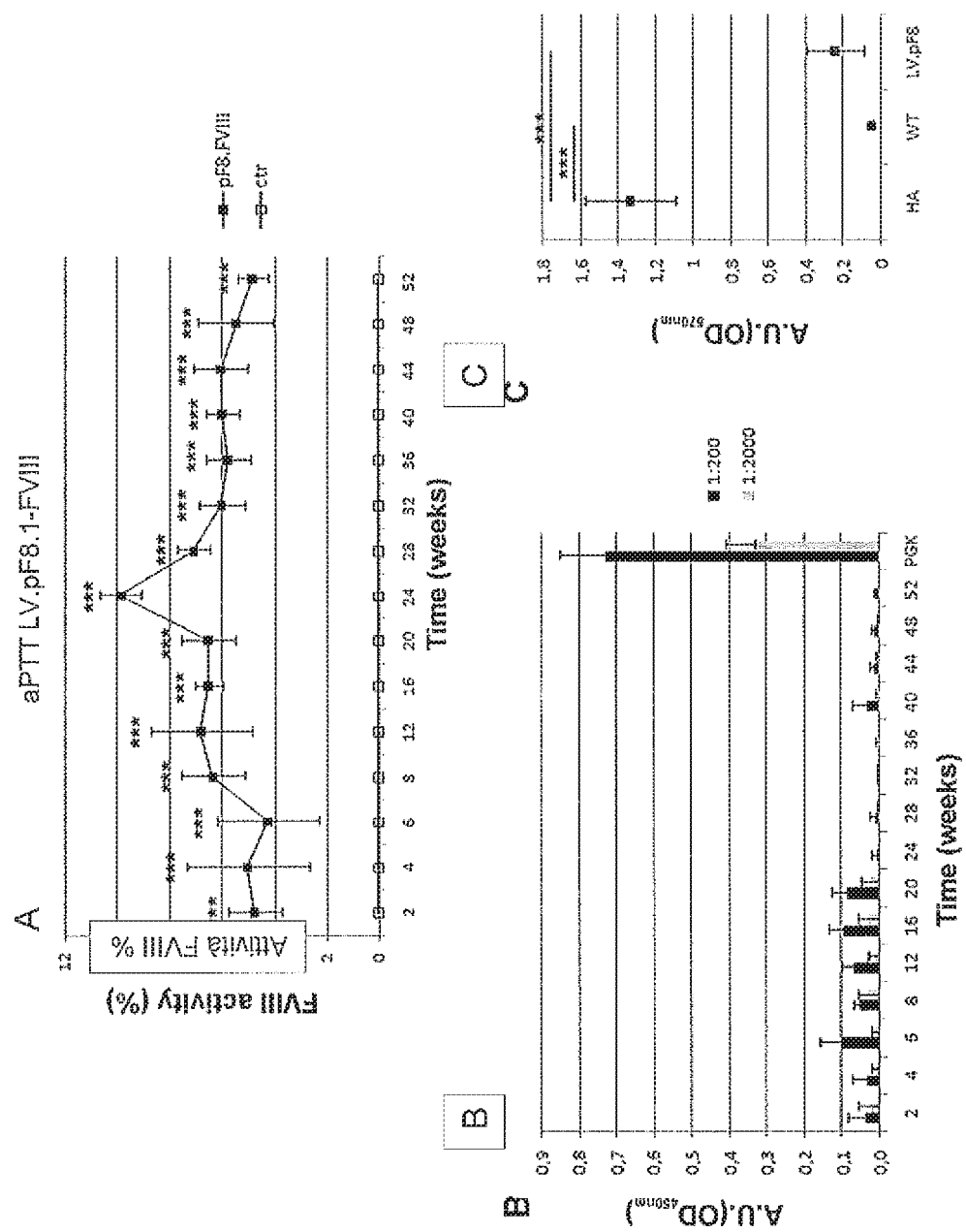

FIG. 3 shows a graphic representation of FVIII activity up to 1 year tested by aPTT assay in hemophilic mice injected with LV.pF8.1-BDD.FVIII (A); ELISA showing the absence of anti-FVIII antibodies formation (B) and a blood loss assay showing as mice undergoing gene therapy were phenotypically corrected and similar to healthy mice (C).

Figure 4:
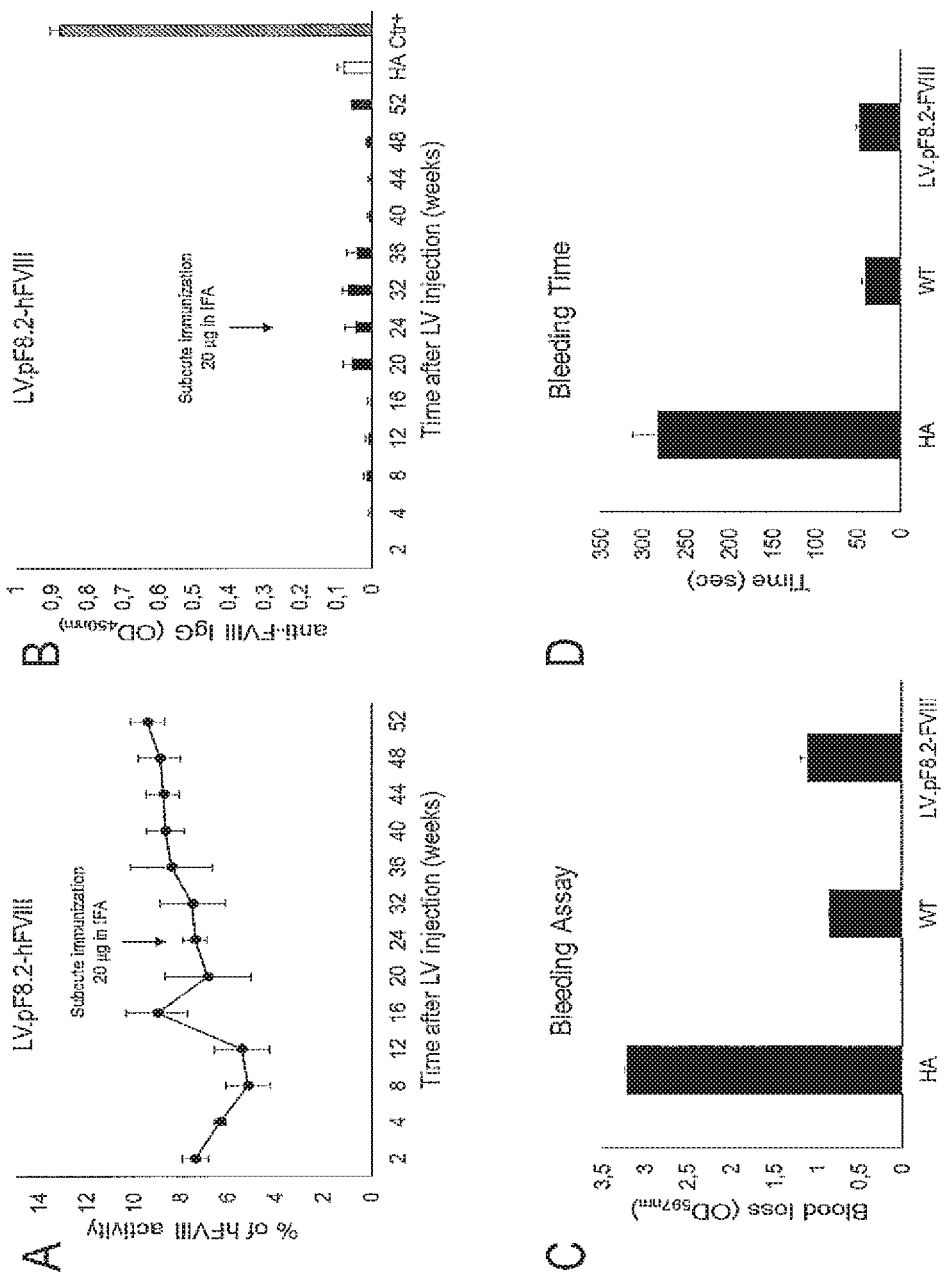

FIG. 4 shows FVIII activity up to 52 weeks in hemophilic mice injected with LV.pF8.2-BDD.FVIII and tested by aPTT assay (A) and ELISA shows the absence of anti-FVIII antibodies formation even after FVIII immunization in the presence of Incomplete Freund's Adjuvant (IFA) at 24 weeks after vector delivering (B). Blood loss (C) after tail clip challenge and tail-bleeding time (D) further confirm achievement of correction of the bleeding phenotype in injected mice.

Figure 5:
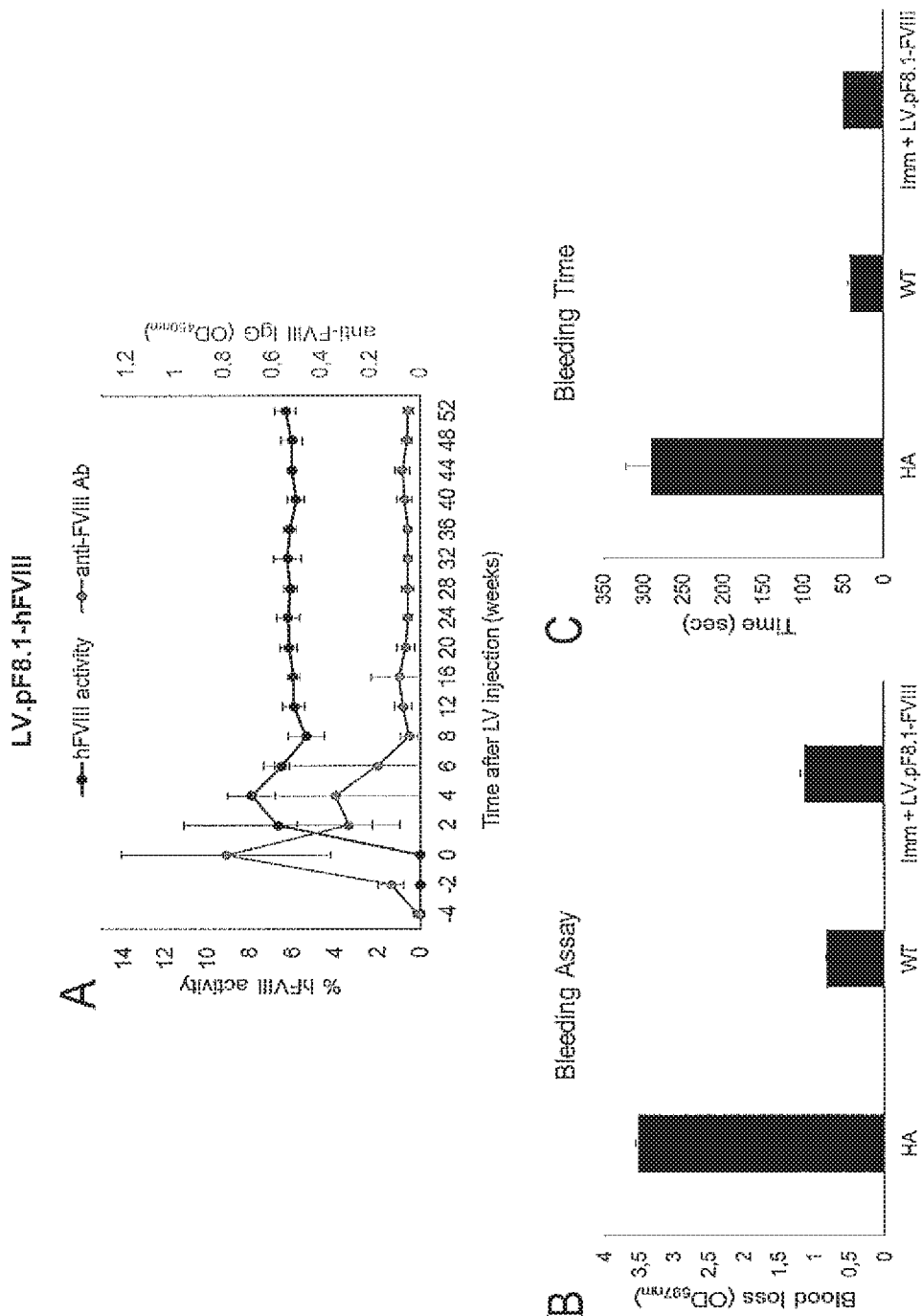

FIG. 5 shows graphic representation of FVIII activity (black line) up to 52 weeks tested by aPTT assay in hemophilic mice injected with LV.pF8.1-BDD.FVIII 4 weeks later FVIII immunization in the presence of IFA (A), and the decline of anti-FVIII antibodies (grey line) present at the moment of LV injection (A). Blood loss (B) after tail clip challenge and tail-bleeding time (C) confirm correction of the bleeding phenotype in injected mice.

FIG. 6 shows the in vitro analysis and validation of FVIII promoter activity. To evaluate pF8 activity in vitro, we transiently transfected HECV cell line with SEQ ID NO: 1 (A), SEQ ID NO: 2 (B) and SEQ ID NO: 12 driving the expression of the luciferase reporter gene in presence of two endothelial transcription factors (Ets1 and Ets2) demonstrating an up-regulation of pF8 in presence of both TFs with a synergistic effect, up to 7 folds increase using the SEQ ID NO: 12 as promoter. ETS1 was able to increase the pF8 activity but with a lower potency (less than 4 fold increase), instead Ets2 alone was unable to increase pF8 activation.

FIG. 7 shows FVIII expression in a different HA mouse strain. B6/129 HA mice (n=7) were injected with LV.pF8.1-hFVIII and hFVIII activity (A) and eventual presence of anti-FVIII antibodies (B) was evaluated starting from 2 weeks after injection. hFVIII activity in the plasma of LV-injected mice reached 12% up to 28 weeks after injection. 1:200 and 1:2000=plasma dilutions. Ctr+=Pooled plasma from hFVIII-injected mice that developed anti-FVIII antibodies.

DETAILED DESCRIPTION

A first aspect of the present invention refers to a new polynucleotide sequence to be used as promoter sequence for inducing/driving/targeting the expression of a therapeutic gene, preferably FVIII and/or its variants (or fragments) specifically in endothelial and/or hematopoietic cells. Therefore, the polynucleotide sequence of the present invention can be also defined as an endothelial and/or haematopoietic-specific transcriptional promoter sequence.

In this context the FVIII mRNA sequence corresponds to the sequence with the NCBI accession number NM_000132.3 while the corresponding Coding Sequence (CDS from now on) has NCBI accession number CCDS35457.1. FVIII is preferably the human B-Domain Deleted (BDD) FVIII, more preferably SEQ ID NO: 11 e/o 15.

The variants of FVIII are preferably molecules with an increased pro-coagulant activity. Preferably, these molecules are FVIII-RH and/or FVIII-N6 that are mutated forms of FVIII. In particular, FVIII-RH molecule is characterized by a substitution present in the canine form of FVIII that is more active of the human one. FVIII-N6 is characterized by a longer B domain included in comparison to the classical B domain deleted form used in gene therapy. Preferably, FVIII-RH is SEQ ID NO: 14 and 16 wherein SEQ ID NO: 16 is a codon-optimized sequence. FVIII-N6 is preferably SEQ ID NO: 14.

The polynucleotide sequence of the invention comprises at least one sequence selected from: SEQ ID NO: 1-10 and 12, preferably from SEQ ID NO: 1-7, 10 and 12. However, in the contest of the present invention any sequence having 80-95% of identity should be considered part of the disclosure.

According to a preferred embodiment, the polynucleotide sequence of the invention comprises:

SEQ ID NO: 1 alone or in combination with SEQ ID NO: 8 and/or 9; and/or

SEQ ID NO: 2 alone or in combination with SEQ ID NO: 8 and/or 9.

Preferably, SEQ ID NO: 8 and/or 9 is (are) positioned upstream and/or downstream and/or close or far from the SEQ ID NO: 1-2.

The sequences of the present invention are listed in Table I and showed in FIGS. 1 and 2.

TABLE I

| Sequence | SEQ ID | Name |
|---|---|---|
| gagctcaccatggctacattctgatgtaaagagatatatcctatacctgggccaaatgtaaacagcct<br>ggaaaagtgttaggttaaaaacaaaacaaaatgaatgccaggtggttatgagtgct<br>attgagaaaaatgaagccaagagggatatcagtgatgcaggtgggggtaaagagcttacaacatataat<br>gtggtgttccatatttaaacctcattcaacagggaagattggagctgaaatgtgaaggagttgtggga<br>gtggaactacgtggaaatctggggggaaaggtgttttgggtaaaagaaatagcaagtgttgaggtccag<br>gggcatgagtgtgcttgatattttagggaagagtaaggagaccagtataaccagagtgagatgagact<br>acagaggtcaggagaaagggcatgcagaccatgtgggatgctctaggacctaggccatggtaaagatg<br>tagggttttaccctgatggaggtcagaagccattggaggattctgagaagaggagtgacaggactcgc<br>tttatagttttaaattataactataaattatagttttaaaacaatagttgcctaacctcatgttata<br>tgtaaaactacagttttaaaaactataaattcctcatactggcagcagtgtgaggggcaagggcaaaa<br>gcagagagactaacaggttgctggttactcttgctagtgcaagtgaattctagaatcttcgacaacat<br>ccagaacttctcttgctgctgccactcaggaagagggttggagtaggctaggaataggagcacaaatt<br>aaagctcctgttcactttgacttctccatccctctcctcctttccttaaaggttctgattaaagcaga<br>cttatgcccctactgctctcagaagtgaatgggttaagtttagcagcctccctttgctacttcagtt<br>cttcctgtggctgcttcccactgataaaaaggaagcaatcctatcggttactgcttagtgctgagcac<br>atccagtgggtaaagttccttaaaatgctctgcaaagaaatttgggacttttcattaaatcagaaattt<br>tacttttttcccctcctgggagctaaagatattttagagaagaattaaccttttgcttctccagttga<br>acatttgtagcaataagtc | SEQ ID NO: 1 | LV.pF8.1 |
| gttttttaaaacaatagttgcctaacctcatgttatatgtaaaactacagttttaaaaactataaattc<br>ctcatactggcagcagtgtgaggggcaagggcaaaagcagagagactaacaggttgctggttactctt<br>gctagtgcaagtgaattctagaatcttcgacaacatccagaacttctcttgctgctgccactcaggaa<br>gagggttggagtaggctaggaataggagcacaaattaaagctcctgttcactttgacttctccatccc<br>tctcctcctttccttaaaggttctgattaaagcagacttatgcccctactgctctcagaagtgaatgg<br>gttaagtttagcagcctcccttttgctacttcagttcttcctgtggctgcttcccactgataaaaagg<br>aagcaatcctatcggttactgcttagtgctgagcacatccagtgggtaaagttccttaaaatgctctg<br>caaagaaatttgggacttttcattaaatcagaaattttacttttttcccctcctgggagctaaagatat<br>tttagagaagaattaaccttttgcttctccagttgaacatttgtagcaataagtc | SEQ ID NO: 2 | LV.pF8.2 |
| Ggggctcgctcgctcagtacctggaggcgagttcctgacgcgactgcgactcaatcctcgcctggtga<br>agaatattttacctatgactcactgaaaataaagacggctgagtgaccgtgtttgttcatgtaaacat<br>tgaacaaatatttatcggcttctgcgatgtgtcctactcttttagtggaggaagacacatttttattta<br>tgtatttaattttcttttgaattttacatgcgagttatacttaataaaactcacttcaaaatatacc<br>ttcaacagaaaatccagcaacagtttctattatgttagttaaaacagccagtcttttccttacttttt<br>aaaaattattcataaatgtaattagtgaatgataataaacattgacatctgatccactgctttaggag<br>tgacacaaatgaagttaactcaggctatttctttataatcattgtgctattgttttctttttcttttt<br>caattatactgcttaatataggattttgtggcaccataggagttgaGGagctcaccatggctacattc<br>tgatgtaaagagatatatcctatacctgggccaaatgtaaacagcctggaaaagtgttaggttaaaaa<br>caaaacaaaatcaaatgaataaatgccaggtggttatgagtgctattgagaaaaatgaagccaag<br>agggatatcagtgatgcaggtgggggtaaagagcttacaacatataatgtggtgttccatatttaaacc<br>tcattcaacagggaagattggagctgaaatgtgaaggagttgtgggagtggaactacgtggaaatctg<br>ggggaaaggtgttttgggtaaaagaaatagcaagtgttgaggtccaggggcatgagtgtgcttgatat<br>tttagggaagagtaaggagaccagtataaccagagtgagatgagactacagaggtcaggagaaagggc<br>atgcagaccatgtgggatgctctaggacctaggccatggtaaagatgtagggttttaccctgatggag<br>gtcagaagccattggaggattctgagaagaggagtgacaggactcgctttatagttttaaattataac<br>tataaattatagttttaaaacaatagttgcctaacctcatgttatatgtaaaactacagttttaaaa<br>actataaattcctcatactggcagcagtgtgaggggcaagggcaaaagcagagagactaacaggttgc<br>tggttactcttgctagtgcaagtgaattctagaatcttcgacaacatccagaacttctcttgctgctg<br>ccactcaggaagagggttggagtaggctaggaataggagcacaaattaaagctcctgttcactttgac<br>ttctccatccctctcctcctttccttaaaggttctgattaaagcagacttatgcccctactgctctca<br>gaagtgaatgggttaagtttagcagcctcccttttgctacttcagttcttcctgtggctgcttcccac<br>tgataaaaaggaagcaatcctatcggttactgcttagtgctgagcacatccagtgggtaaagttcctt<br>aaaatgctctgcaaagaaatttgggacttttcattaaatcagaaattttacttttttcccctcctggga<br>gctaaagatattttagagaagaattaaccttttgcttctccagttgaacatttgtagcaataagtc | SEQ ID NO: 3 | LV.pF8.3 |
| Ggggctcgctcgctcagtacctggaggcgagttcctgacgcgactgcgactcaatcctcgcctggtga<br>agaatattttacctatgactcactgaaaataaagacggctgagtgaccgtgtttgttcatgtaaacat<br>tgaacaaatatttatcggcttctgcgatgtgtcctactcttttagtggaggaagacacatttttattta<br>tgtatttaattttcttttgaattttacatgcgagttatacttaataaaactcacttcaaaatatacc<br>ttcaacagaaaatccagcaacagtttctattatgttagttaaaacagccagtcttttccttacttttt<br>aaaaattattcataaatgtaattagtgaatgataataaacattgacatctgatccactgctttaggag<br>tgacacaaatgaagttaactcaggctatttctttataatcattgtgctattgttttctttttcttttt<br>caattatactgcttaatataggattttgtggcaccataggagttgaGGttttaaaacaatagttgcc<br>taacctcatgttatatgtaaaactacagttttaaaaactataaattcctcatactggcagcagtgtga<br>ggggcaagggcaaaagcagagagactaacaggttgctggttactcttgctagtgcaagtgaattctag<br>aatcttcgacaacatccagaacttctcttgctgctgccactcaggaagagggttggagtaggctagga<br>ataggagcacaaattaaagctcctgttcactttgacttctccatccctctcctcdttccttaaaggtt<br>ctgattaaagcagacttatgcccctactgctctcagaagtgaatgggttaagtttagcagcctccctt<br>ttgctacttcagttcttcctgtggctgcttcccactgataaaaaggaagcaatcctatcggttactgc<br>ttagtgctgagcacatccagtgggtaaagttccttaaaatgctctgcaaagaaatttgggacttttcat<br>taaatcagaaattttacttttttcccctcctgggagctaaagatattttagagaagaattaacctttt<br>gcttctccagttgaacatttgtagcaataagtc | SEQ ID NO: 4 | LV.pF8.4 |
| Tcgccaccacttggcttccggcacgtgggcagatgtttccattcccacggcggcagcggaagaggga<br>gggccgggcgccgcggctgcttgcagtctccgcaagcggctacatcacagagctcagcgtgcggtg<br>tcacaggccccgcggtcccgcccaacagatgcaccgagatgcgcgtgcgcagaaagcgtcccgggggt<br>gaggctccctccctcgctctccctctactcccgccccactctcccccacttttccccctccacccacc | SEQ ID NO: 5 | LV.pF8.5 |

TABLE I-continued

| | | |
|---|---|---|
| gcggccgtcggggctcgctcgctcagtacctggaggcgagttcctgacgcgactgcgactcaatcctc<br>gcctggtgaagaatattttacctatgactcactgaaaataaagacggctgagtgaccgtgtttgttca<br>tgtaaacattgaacaaatatttatcggcttctgcgatgtgtcctactcttttagtggaggaagacaca<br>ttttatttatgtatttaatttttcttttgaatttttacatgcgagttatacttaataaaactcacttca<br>aaatatacctttcaacagaaaatccagcaacagtttctattatgttagttaaaacagccagtcttttcc<br>tttacttttaaaaattattcataaatgtaattagtgaatgataataaacattgacatctgatccactg<br>ctttaggagtgacacaaatgaagttaaactcaggctattttctttataatcattgtgctattgttttct<br>ttttcttttcaattatactgcttaatataggattttgtggcaccataggagttgaGGagctcaccatg<br>gctacattctgatgtaaagagatatatcctatacctgggcaaatgtaaacagcctggaaaagtgtta<br>ggttaaaaacaaaacaaatataaataatgaataaatgccaggtggttatgagtgctattgagaaaat<br>gaagccaagagggatatcagtgatgcaggtgggggtaaagagcttacaacataaatgtggtgttccat<br>atttaaacctcattcaacagggaagattggagctgaaatgtgaaggagttgtgggagtggaactacgt<br>ggaaatctggggaaaggtgtttgggtaaaagaaatagcaagtgttgaggtccaggggcatgagtgt<br>gcttgatattttagggaagagtaaggagaccagtataaccagagtgagatgagactacagaggtcagg<br>agaaagggcatgcagaccatgtgggatgctctaggacctaggccatggtaaagatgtagggttttacc<br>ctgatggaggtcagaagccattggaggattctgagaagaggagtgacaggactcgctttatagttttta<br>aattataactataaattatagttttaaaacaatagttgctaacctcatgttatatgtaaaactaca<br>gttttaaaaactataaattcctcatactggcagcagtgtgaggggcaagggcaaaagcagagagacta<br>acaggttgctggttactcttgctagtgcaagtgaattctagaatcttcgacaacatccagaacttctc<br>ttgctgctgccactcaggaagagggttggagtaggctaggaataggagcacaaattaaagctcctgtt<br>cactttgacttctccatccctctcctcctttccttaaaggttctgattaaagcagacttatgcccta<br>ctgctctcagaagtgaatgggttaagtttagcagcctcccttttgctacttcagttcttcctgtggct<br>gcttcccactgataaaaaggaagcaatcctatcggttactgcttagtgctgagcacatccagtgggta<br>aagttccttaaaatgctctgcaaagaaattgggacttttcattaaatcagaaattttactttttccc<br>ctcctgggagctaaagatattttagagaagaattaaccttttgcttctccagttgaacatttgtagca<br>ataagtc | | |
| Tcgccaccacttggcttccggcacgtggggcagatgtttccattcccacggcggcagcggaagaggga<br>gggccgggcgcgccgcggctgcttgcagtctccgcaagcggctacatcacagagctcagcgtgcggtg<br>tcacaggccccgcggtcccgccaacagatgcaccgagatgcgcgtgcgcagaaagcgtcccgggggt<br>gaggctccctccctcgctctccctctactcccgccccactctcccccactttcccccctccaccacc<br>gcggccgtcggggctcgctcgctcagtacctggaggcgagttcctgacgcgactgcgactcaatcctc<br>gcctggtgaagaatattttacctatgactcactgaaaataaagacggctgagtgaccgtgtttgttca<br>tgtaaacattgaacaaatatttatcggcttctgcgatgtgtcctactcttttagtggaggaagacaca<br>ttttatttatgtatttaatttttcttttgaatttttacatgcgagttatacttaataaaactcacttca<br>aaatatacctttcaacagaaaatccagcaacagtttctattatgttagttaaaacagccagtcttttcc<br>tttacttttaaaaattattcataaatgtaattagtgaatgataataaacattgacatctgatccactg<br>ctttaggagtgacacaaatgaagttaaactcaggctattttctttataatcattgtgctattgttttct<br>ttttcttttcaattatactgcttaatataggattttgtggcaccataggagttgaGGttttttaaaaca<br>atagttgctaacctcatgttatatgtaaaactacagttttaaaaactataaattcctcatactggca<br>gcagtgtgaggggcaagggcaaaagcagagagactaacaggttgctggttactcttgctagtgcaagt<br>gaattctagaatcttcgacaacatccagaacttctcttgctgctgccactcaggaagagggttggagt<br>aggctaggaataggagcacaaattaaagctcctgttcactttgacttctccatccctctcctcctttc<br>cttaaaggttctgattaaagcagacttatgcccctactgctctcagaagtgaatgggttaagtttagc<br>agcctcccttttgctacttcagttcttcctgtggctgcttcccactgataaaaaggaagcaatcctat<br>cggttactgcttagtgctgagcacatccagtgggtaaagttccttaaaatgctctgcaaagaaattgg<br>gacttttcattaaatcagaaattttactttttccccctcctgggagctaaagatattttagagaagaa<br>ttaaccttttgcttctccagttgaacatttgtagcaataagtc | SEQ ID<br>NO: 6 | LV.pF8.6 |
| cagcagttcccacaaacgttaccctcacaatgaatccagccattttttcaccctctccagtggtaccat<br>catagcccaagccgccaccattctcacccccggttaacaggccaccctccttctacccttatcctgc<br>tagagtttgttttatctacagtgatcagaaagatcagcctaaaagataattctgatcaccaccctcct<br>ctactcacaacccggccgtgtctcccattgccctcagtgtagaagtcaatgtccctttgctgaaatg<br>caacctcagtgaaacttccatgactaacctccttttaaaattgcaactggtccaccccttactcccc<br>ttaccccccacttctctttttgcacagcacttattttaccttctaacatactctataatgtactcatgt<br>attgtaattattgcttatcatccctctttcagttgcttataatttttcatcaatgtgtacccagtgcct<br>aggacaatatcgtctaggacaaatgggtagttatgtggctgtaggcaagccatttaacctctctgta<br>cctcagttacttatctgtatccactttgcggtgttgtcatgaggattaaatcagatagcctatgtgt<br>agcacctggcagtgaattatcaccctgtactgtaactgtctaatttctgtctcctccattggactg<br>tcattcccaggggttgggaactgggatttcttcatttctgaggcatagaagtatagcatagtggtta<br>ggagcatgacttctggagccagagtacatgggtttgaatgctaccactcacaagctgtgtggccatgg<br>agaagttgcctaacctctccgtgcttcagtttcatcacccataaaatgaaggtaagaatagtacctgt<br>atttaaaagcacctagaacagttcctggcatatagtgtcagctgtcatctctgcatccttgtacctgt<br>cagagaggagtgtttatcaaagggggcttcttgctgcctgtttccaaaccagtcgacaatataccaatt<br>gctccctaacacattcttgtttgtgcagaactgagctcaatgataacattttttatagcaaccctgatc<br>aagtttcttctcataatctcttacactttgaggccccctgcaggggccctcactctccctaataaacat<br>taacctgatagggtgtttgagctcaccatggctacattctgatgtaaagagatatatcctatacctg<br>ggccaaatgtaaacagcctggaaaagtgttaggttaaaaacaaaacaaatataaatgaataaatg<br>ccaggtggttatgagtgctattgagaaaatgaagccaagagggatatcagtgatgcaggtgggggta<br>aagagcttacaacataaatgtggtgttccatatttaaacctcattcaacagggaagattggagctgaa<br>atgtgaaggagttgtgggagtggaactacgtggaaatctggggaaaggtgtttgggtaaaagaaaat<br>agcaagtgttgaggtccaggggcatgagtgtgcttgatattttagggaagagtaaggagaccagtata<br>accagagtgagatgagactacagaggtcaggagaaagggcatgcagaccatgtgggatgctctaggac<br>ctaggccatggtaaagatgtagggttttaccctgatggaggtcagaagccattggaggattctgagaa<br>gaggagtgacaggactcgctttatagtttttaaattataactataaattatagttttttaaaacaatagt<br>tgcctaacctcatgttatatgtaaaactacagttttaaaaactataaattcctcatactggcagcagt<br>gtgaggggcaagggcaaaagcagagagactaacaggttgctggttactcttgctagtgcaagtgaatt<br>ctagaatcttcgacaacatccagaacttctcttgctgctgccactcaggaagagggttggagtaggct<br>aggaataggagcacaaattaaagctcctgttcactttgacttctccatccctctcctcctttccttaa<br>aggttctgattaaagcagacttatgcccctactgctctcagaagtgaatgggttaagtttagcagcct | SEQ ID<br>NO: 7 | 0 to 2350<br>5' FVIII<br>promoter<br>sequence |

TABLE I-continued

| | | |
|---|---|---|
| cccttttgctacttcagttcttcctgtggctgcttcccactgataaaaaggaagcaatcctatcggtt<br>actgcttagtgctgagcacatccagtgggtaaagttccttaaaatgctctgcaaagaaattgggactt<br>ttcattaaatcagaaattttactttttttccctcctgggagctaaagatattttagagaagaattaac<br>cttttgcttctccagttgaacatttgtagcaataagtc | | |
| Ggggctcgctcgctcagtacctggaggcgagttcctgacgcgactgcgactcaatcctcgcctggtga<br>agaatattttacctatgactcactgaaaataaagacggctgagtgaccgtgtttgttcatgtaaacat<br>tgaacaaatatttatcggcttctgcgatgtgtcctactcttttagtggaggaagacacatttttattta<br>tgtatttaatttttctttgaattttacatgcgagttatacttaataaaactcacttcaaaatatacc<br>ttcaacagaaaatccagcaacagtttctattatgttagttaaaacagccagtcttttcctttacttt<br>aaaaattattcataaatgtaattagtgaatgataataaacattgacatctgatccactgctttaggag<br>tgacacaaatgaagttaactcaggctattttctttataatcattgtgctattgttttcttttctttt<br>caattatactgcttaatataggattttgtggcaccataggagttgag | SEQ ID<br>NO: 8 | Enhancer<br>Short |
| Tcgccaccacttggcttccggcacgtggggcagatgtttccattcccacggcggcagcggaagaggga<br>gggccgggcgcgccgcggctgcttgcagtctccgcaagcggctacatcacagagctcagcgtgcggtg<br>tcacaggccccgcggtcccgcccaacagatgcaccgagatgcgcgtgcgcagaaagcgtccgggggt<br>gaggctcccctccctcgctctccctctactcccgccccactctcccccactttccccctccacccacc<br>gcggccgtcggggctcgctcgctcagtacctggaggcgagttcctgacgcgactgcgactcaatcctc<br>gcctggtgaagaatattttacctatgactcactgaaaataaagacggctgagtgaccgtgtttgttca<br>tgtaaacattgaacaaatatttatcggcttctgcgatgtgtcctactcttttagtggaggaagacaca<br>tttttatttatgtatttaattttttcttttgaattttacatgcgagttatacttaataaaaactcacttca<br>aaatatacctttcaacagaaaatccagcaacagtttctattatgttagttaaaacagccagtcttttcc<br>tttacttttaaaaattattcataaatgtaattagtgaatgataataaacattgacatctgatccactg<br>ctttaggagtgacacaaatgaagttaactcaggctattttctttataatcattgtgctattgttttct<br>ttttcttttcaattatactgcttaatataggattttgtggcaccataggagttgag | SEQ ID<br>NO: 9 | Enhancer<br>Long |
| tcgccaccacttggcttccggcacgtggggcagatgtttccattcccacggcggcagcggaagaggga<br>gggccgggcgcgccgcggctgcttgcagtctccgcaagcggctacatcacagagctcagcgtgcggtg<br>tcacaggccccgcggtcccgcccaacagatgcaccgagatgcgcgtgcgcagaaagcgtccgggggt<br>gaggctcccctccctcgctctccctctactcccgccccactctcccccactttccccctccacccacc<br>gcggccgtcggggctcgctcgctcagtacctggaggcgagttcctgacgcgactgcgactcaatcctc<br>gcctggtgaagaatattttacctatgactcactgaaaataaagacggctgagtgaccgtgtttgttca<br>tgtaaacattgaacaaatatttatcggcttctgcgatgtgtcctactcttttagtggaggaagacaca<br>tttttatttatgtatttaattttttcttttgaattttacatgcgagttatacttaataaaaactcacttca<br>aaatatacctttcaacagaaaatccagcaacagtttctattatgttagttaaaacagccagtcttttcc<br>tttacttttaaaaattattcataaatgtaattagtgaatgataataaacattgacatctgatccactg<br>ctttaggagtgacacaaatgaagttaactcaggctattttctttataatcattgtgctattgttttct<br>ttttcttttcaattatactgcttaatataggattttgtggcaccataggagttgagtaaaaataaaag<br>gaataaaaatataccttatctggccggggcgcggtggctcacgcctgtaatttcagcagtttcggaggc<br>cgaggcgggcggatcacgcggtcaggagatcgaggccatcctggctaacatggtgaaaccccgtctct<br>actaaaaatacaaaaaattagccgggcatggtggcgggcgcctgtagtcccagctactcggggaggctg<br>aggcaggagaatggcgtgaacccgggaggcggagcttgcagtgagccgagatcgcgacactgcactcc<br>agcctgggcgacagagtgagactgcgtctccaaaaaaaaaagaaaaaatacgttatctatgaagattt<br>ccaatttgatttctatttatcacaaatggccacagtactcctttgtactttaccacataccatattgt<br>attcagtaattatttgtgaatatgtaattgataatattgtaggttttagagaatccttgaaaacatga<br>aaatttggtaatggggtctattttgattatttatttatttatttatttattttgagacagag<br>tctcgctcttgttgcccaggctggagtgcagtggcgcgatctcggctcactgcaagctccacctcccg<br>ggttcaagcgattctcctgcctcagcctcccaagtagctgggactacaggcacgtgccaccatgcccg<br>gctaatttttgtatttttagtagagaggagtttcatcttgttagctaggatggtctagatctcctg<br>acctcgtgatctgcccgcctcagcctcccaaagtgctgggattacaggtgtgagccaccgtgcccggc<br>catatttgatttaaaatttagcaataatagataaaattttcaatcaactaagcccttgggccaggga<br>atgctattccttaaaagtgcttctatcaatatagcctctgactcattactttgttaattttttaaatt<br>gtatttcattcctgattaacattcccaccccagattattaattatacaatctgttaactgtagaacctc<br>aaacatgttggattgtactgtattttgtctggaagacacattttttaaaacattgtaatcgctataagag<br>aagcactgggaaagaaaggagcttctatgcctgcagtgcctgaggagcccttaacagtgtgccccgc<br>ccctaagctactcatgcagtcatcccatcccagttagtcaactttattccaaaaaacttggtgttcc<br>aaatttttccttctcaaagcccacagatccaaaattcatcagcagttcccacaaacgttaccctcaca<br>atgaatccagccattttccaccctctccagtggtaccatcagacccaagccgccaccattctcacc<br>cccggttaacaggccaccctccttctacccttatcctgctagagtttgttttatctacagtgatcaga<br>aagatcagcctaaaagataattctgatcaccaccctcctctactcacaacccggccgtgtctccccat<br>tgccctcagtgtagaagtcaatgtccctttgctgaaatgcaaccttagtgaaactttccatgactaac<br>ctccttttaaaattgcaacctggtccaccctttactcccccttaccccacttctcttttttgcacagcac<br>ttattttaccttctaacatactgtataatgtactcatgtattgtaattattgcttatcatccctcttt<br>cagttgcttatattttcatcaatgtgtacccagtgcctaggacaatatctgtctaggacaaatgggt<br>agttatgtggctgtaggcaagccatttaacctctctgtacctcagttactttatctgtatccactttg<br>cggtgttgtcatgaggattaaatcagatagcctatgtgtagcacctggtgaattatcaccctgt<br>actgtaactgtctactttctgtctcctccattggactgtcattcccaggggggtgggaactgggatt<br>tcttcatttctgaggcatagaagtatagcatagtggttaggagcatgacttctggagccagagtacat<br>gggtttgaatgctaccactcacaagctgtgtggccatggagaagttgcctaacctctccgtgcttcag<br>tttcatcacccataaaatgaaggtaagaatagtacctgtatttaaaagcacctagaaacagttcctggc<br>atatagtgtcagctgtcatctctgcatccttgtacctgtcagagaggagtgtttatcaaaggggcttc<br>ttgctgcctgtttccaaaccagtcgacaatataccaattgctccctaacacattcttgtttgtgcaga<br>actgagctcaatgataacatttttatagcaaccctgatcaagtttcttctcataatctcttacatttt<br>gaggccctgcaggggccctcactctccctaataaacattaacctgagtagggtgtttgagctcaca<br>tggctacattctgatgtaaagagatatatcctataccctgggccaaatgtaaacagcctggaaaagtgt<br>taggtaaaaacaaaacaaaataaaatgaataaaatgccaggtggttatgagtgctattgagaaaa<br>atgaagccaagagggatatcagtgatgcaggtgggggtaaagagcttacaacataaatggtgttcc<br>atatttaaacctcattcaacagggaagattggagctgaaatgtgaaggagttgtgggagtggaactac<br>gtggaaatctgggggaaaggtgttttgggtaaaagaaatagcaagtgttgaggtccaggggcatgagt | SEQ ID<br>NO: 10 | Full 5'<br>FVIII<br>promoter<br>sequence |

TABLE I-continued

| | |
|---|---|
| gtgcttgatattttagggaagagtaaggagaccagtataaccagagtgagatgagactacagaggtca ggagaaagggcatgcagaccatgtgggatgctctaggacctaggccatggtaaagatgtagggtttta ccctgatggaggtcagaagccattggaggattctgagaagaggagtgacaggactcgctttatagttt taaattataactataaattatagtttttaaaacaatagttgcctaaccctcatgttatatgtaaaacta cagttttaaaaactataaattcctcatactggcagcagttgctgaggggcaagggcaaaagcagagagac taacaggttgctggttactcttgctagtgcaagtgaattctagaatcttcgacaacatccagaacttc tcttgctgctgccactcaggaagagggttggagtaggctaggaataggagcacaaattaaagctcctg ttcactttgacttctccatccctcctccttcctaaaggttctgattaaagcagacttatgcccc tactgctctcagaagtgaatgggttaagtttagcagcctccctttgctacttcagttcttcctgtgg ctgcttcccactgataaaaaggaagcaatcctatcggttactgcttagtgctgagcacatccagtggg taaagttccttaaaatgctctgcaaagaaattgggacttttcattaaatcagaaattttacttttttc ccctcctgggagctaaagatatttagagaagaattaaccttttgcttctccagttgaacatttgtag caataagtc | |
| atgcaaatagagctctccacctgcttctttctgtgccttttgcgattctgctttagtgccaccagaag atactacctgggtgcagtggaactgtcatgggactatatgcaaagtgatctcggtgagctgcctgtgg acgcaagattcctcctagagtgccaaaatcttttccattcaacacctcagtcgtgtacaaaaagact ctgtttgtagaattcacggatcaccttttcaacatcgctaagccaaggccaccctggatgggtctgct aggtcctaccatccaggctgaggtttatgatacagtggtcattacacttaagaacatggcttcccatc ctgtcagtcttcatgctgttggtgtatcctactgaaagcttctgagggagctgaatatgatgatcag accagtcaaagggagaaagaagatgataaagtcttccctggtggaacgcatacatatgtctggcaggt cctgaaagagaatggtccaatggcctctgacccactgtgccttacctactcatatctttctcatgtgg acctggtaaaagacttgaattcaggcctcattggagccctactagtatgtagagaagggagtctggcc aaggaaaagacacagaccttgcacaaatttatactactttttgctgtatttgatgaagggaaaagttg gcactcagaaacaaagaacttccttgatgcaggatagggatgctgcatctgctcgggcctggcctaaa tgcacacagtcaatggttatgtaaacaggtctctgccaggtctgattggatgccacaggaaatcagtc tattggcatgtgattggaatgggcaccactcctgaagtgcactcaatattcctcgaaggtcacacatt tcttgtgaggaaccatcgccaggcgtccttggaaatctcgccaataactttccttactgctcaaacac tcttgatggaccttggacagtttctactgtttgtcatatctcttcccaaccaacatgatggcatggaa gcttatgtcaaagtagacagctgtccagaggaacccaactacgaatgaaaataatgaagaagcgga agactatgatgatgatcttactgattctgaaatggatgtggtcaggtttgatgatgacaactctcctt cctttatcccaaattcgctcagttgccaagaagcatcctaaaacttgggtacattacattgctgctgaa gaggaggactgggactatgctccctagtcctcgcccccgatgacagaagttataaaagtcaatattt gaacaatggccctcagcggattggtaggaagtacaaaaaagtccgatttatgtgcatacacagatgaa cctttaagactcgtgaagctattcagcatgaatcaggaatcttgggaccttttactttatggggaagtt ggagacacactgttgattatatttaagaatcaagcaagcagaccatataacatctaccctcacggaat cactgatgtccgtcctttgtattcaaggagattaccaaaaggtgtaaaacatttgaaggattttccaa ttctgccaggagaaatattcaaatataaatggacagtgactgtagaagatgggccaactaaaatcagat cctcggtgcctgacccgctattactctagtttcgttaatatggagagagatctagcttcaggactcat tggccctctcctcatctgctacaaagaatctgtagatcaaagaggaaaccagataatgtcagacaaga gggaatgtcatcctgttttctgtatttgatgagaaccgaagctggtacctcacagagaatatacaacgc tttctcccaatccagctgagtgcagcttgaggatccagagttccaagcctcaacatcatgcacag catcaatggctatgttttggatagtttgcagttgtcagtttgtttgcatgaggtggcatactggtaca ttctaagcattggagcacagactgacttccttttctgtcttcttctctggatataccttcaaacacaaa atggtctatgaagcacacactcaccctattcccattctcaggagaaactgtcttcatgtcgatggaaaa cccaggtctatggattctggggtgccacaactcagactttcggaacagaggcatgaccgcctactga aggtttctagttgtgacaagaacactggtgattattacgaggacagttatgaagatatttcagcatac ttgctgagtaaaaacaatgccattgaaccaagaagcttctcccaaaaccaccagtcttgaaacgcca tcaacgggaaataactcgtactactcttcagtcagatcaagaggaaattgactatgatgataccatat cagttgaaatgaagaaggaagattttgacatttatgatgaggatgaaaatcagaggccccgcagctt caaaagaaaacacgacactatttattgctgcagtggagaggctctgggattatgggatgagtagctc cccacatgttctaagaaacagggctcagagtggcagtgtccctcagttcaagaaagttgtttccagg aatttactgatggctcctttactcagcccttataccgtggagaactaaatgaacatttgggactcctg gggcatatatagaagcagaagttgaagataaatatcatggtaactttcagaaatcaggcctctcgtcc ctattccttctattctagccttatttcttatgaggaagatcagaggcaaggagcagaacctagaaaaa actttgtcaagcctaatgaaaccaaaacttacttttggaaagtgcaacatcatatggcaccactaaa gatgagtttgactgcaaagcctgggcttatttctctgatgttgacctggaaaaagatgtgcactcagg cctgattggaccccttctggtctgccacactaacacactgaaccctgctcatgggagacaagtgacag tacaggaatttgctctgttttccaccatcttgatgaaacaaagtggtacttcactgaaaatatg gaaagaaactgcagggctccctgcaatatccagatggaagatcccacttttaaagagaattatcgctt ccatgcaatcaatggctacataatggatacactacctggcttagtaatggctcaggatcaaaggattc gatggtatctgctcagcatgggcagcaatgaaaacatccattctattcatttcagtggacatgtgttc accgtacgaaaaaagaggagtataaaatggcactgtcaactctatccaggtgtttttgagacagt ggaaatgttaccatccaaagctggaatttggcgggtggaatgcctattggcgagcatctacatgctg ggatgagcacactttttctggtgtacagcaataagtgtcagactccctgggaatggcttctggacac attagagattttcagattacagcttcaggacaatatggacagtgggcccaaagctggccagacttca ttattccggatcaatcaatgcctggagcaccaaggagcccttctcaaggtggatctgttgg caccaatgattattcacggcatcaagacccagggtgcccgtcagaagttctccagcctctacatctct cagtttatcatcatgtatagtcttgatgggaagaagtggcagacttatcgaggaaattccactggaac cttaatggtcttctttggcaatgtggattcatctgggataaaacacaatatttttaaccctccaatta ttgctcgatacatccgtttgcaccccaactcattatagcattcgacactcttcgcatggagttgatg ggctgtgatttaaatagttgcagcatgccattgggaatggagagtaaagcaatatcagatgcacagat tactgcttcatcctactttaccaatatgtttgccacctggtctccttcaaaagctcgacttcacctcc aagggaggagtaatgcctgagacctcaggtgaataatccaaaagagtggctgcaagtggacttccag aagacagaaagtcacaggagtaactactcaggagtaaatctcgcttaccaggctatgtgaa ggagttcctcatctccagcagtcaagatggccatcagtggactctcttttttcagaatggcaaagtaa aggtttttcagggaaatcaagactccttcacacctgtggtgaactctctagaccaccgttactgact cgctaccttcgaattcaccccagagttgggtgcaccagattgccctgaggatggaggttctgggctg cgaggcacaggacctctactga | SEQ ID NO: 11 BDD FVIII |

TABLE I-continued

| | | |
|---|---|---|
| aatcttcgacaacatccagaacttctcttgctgctgccactcaggaagagggttggagtaggctagga<br>ataggagcacaaattaaagctcctgttcactttgacttctccatccctctcctcctttccttaaaggt<br>tctgattaaagcagacttatgcccctactgctctcagaagtgaatgggttaagtttagcagcctccct<br>tttgctacttcagttcttcctgtggctgcttcccactgataaaaaggaagcaatcctatcggttactg<br>cttagtgctgagcacatccagtgggtaaagttccttaaaatgctctgcaaagaaattgggactttca<br>ttaaatcagaaattttactttttccctcctgggagctaaagatattttagagaagaattaacctttt<br>tgcttctccagttgaacatttgtagcaataagtc | SEQ ID<br>NO: 12 | LV.pF8.8 |
| ATGCAAAGTGATCTCGGTGAGCTGCCTGTGGACGCAAGATTTCCTCCTAGAGT<br>GCCAAAATCTTTTCCATTCAACACCTCAGTCGTGTACAAAAAGACTCTGTTTGTA<br>GAATTCACGGATCACCTTTTCAACATCGCTAAGCAAGGCCACCCTGGATGGG<br>TCTGCTAGGTCCTACCATCCAGGCTGAGGTTATGATACAGTGGTCATTACACT<br>TAAGAACATGGCTTCCCATCCTGTCAGTCTTCATGCTGTTGGTGTATCCTACTG<br>GAAAGCTTCTGAGGGAGCTGAATATGATGATCAGACCAGTCAAAGGGAGAAAG<br>AAGATGATAAAGTCTTCCCTGGTGGAAGCCATACATATGCTGGCAGGTCCTGA<br>AAGAGAATGGTCCAATGGCCTCTGACCCACTGTGCCTTACCTACTCATATCTTT<br>CTCATGTGGACCTGGTAAAAGACTTGAATTCAGGCCTCATTGGAGCCCTACTAG<br>TATGTAGAGAAGGGAGTCTGGCCAAGGAAAAGACACAGACCTTGCACAAATTT<br>ATACTACTTTTTGCTGTATTTGATGAAGGGAAAAGTTGGCACTCAGAAACAAAG<br>AACTCCTTGATGCAGGATAGGGATGCTGCATCTGCTCGGGCCTGGCCTAAAAT<br>GCACACAGTCAATGGTTATGTAAACAGGTCTCTGCCAGGTCTGATTGGATGCC<br>ACAGGAAATCAGTCTATTGGCATGTGATTGGAATGGGCACCACTCCTGAAGTG<br>CACTCAATATTCCTCGAAGGTCACACATTTCTTGTGAGGAACCATCGCCAGGCG<br>TCCTTGGAAATCTCGCCAATAACTTTCCTTACTGCTCAAACACTCTTGATGGAC<br>CTTGGACAGTTTCTACTGTCTTGTCATATCTCTTCCCACCAACATGATGGCATG<br>GAAGCTTATGTCAAAGTAGACAGCTGTCCAGAGGAACCCCAACTACGAATGAA<br>AAATAATGAAGAAGCGGAAGACTATGATGATGATCTTACTGATTCTGAAATGGA<br>TGTGGTCAGGTTTGATGATGACAACTCTCCTTCCTTTATCCAAATTCGCTCAGTT<br>GCCAAGAAGCATCCTAAAACTTGGGTACATTACATTGCTGCTGAAGAGGAGGA<br>CTGGGACTATGCTCCCTTAGTCCTCGCCCCCGATGACAGAAGTTATAAAAGTCA<br>ATATTTGAACAATGGCCCTCAGCGGATTGGTAGGAAGTACAAAAAAGTCCGATT<br>TATGGCATACACAGATGAAACCTTTAAGACTCGTGAAGCTATTCAGCATGAATC<br>AGGAATCTTGGGACCTTTACTTTATGGGGAAGTTGGAGACACACTGTTGATTAT<br>ATTTAAGAATCAAGCAAGCAGACCATATAACATCTACCCTCACGGAATCACTGA<br>TGTCCGTCCTTTGTATTCAAGGAGATTACCAAAAGGTGTAAAACATTTGAAGGA<br>TTTTCCAATTCTGCCAGGAGAAATATTCAAATATAAATGGACAGTGACTGTAGAA<br>GATGGGCCAACTAAATCAGATCCTCGGTGCCTGACCCGCTATTACTCTAGTTTC<br>GTTAATATGGAGAGAGATCTAGCTTCAGGACTCATTGGCCCTCTCCTCATCTGC<br>TACAAAGAATCTGTAGATCAAAGAGGGAAACCAGATAATGTCAGACAAGAGGAAT<br>GTCATCCTGTTTTCTGTATTTGATGAGAACCGAAGCTGGTACCTCACAGAGAAT<br>ATACAACGCTTTCTCCCCAATCCAGCTGGAGTGCAGCTTGAGGATCCAGAGTT<br>CCAAGCCTCCAACATCATGCACAGCATCAATGGCTATGTTTTTGATAGTTTGCA<br>GTTGTCAGTTTGTTTGCATGAGGTGGCATACTGGTACATTCTAAGCATTGGAGC<br>ACAGACTGACTTCCTTTCTGTCTTCTTCTCTGGATATACCTTCAAACACAAAATG<br>GTCTATGAAGACACACTCACCCTATTCCCATTCTCAGGAGAAACTGTCTTCATG<br>TCGATGGAAAACCCAGGTCTATGGATTCTGGGGTGCCACAACTCAGACTTTCG<br>GAACAGAGGCATGACCGCCTTACTGAAGGTTTCTAGTTGTGACAAGAACACTG<br>GTGATTATTACGAGGACAGTTATGAAGATATTTCAGCTACTTGCTGAGTAAAAA<br>CAATGCCATTGAACCAAGAAGCTTCTCCCAGAATTCAAGACACCCTAGCACTAG<br>GCAAAAGCAATTTAATGCCACCACAATTCCAGAAAATGACATAGAGAAGACTGA<br>CCCTTGGTTTGCACACAGAACACCTATGCCTAAAATACAAAATGTCTCCTCTAG<br>TGATTTGTTGATGCTCTTGCGACAGAGTCCTACTCCACATGGGTATCCTTATC<br>TGATCTCCAAGAAGCCAAATATGAGACTTTTTCTGATGATCCATCACCTGGAGC<br>AATAGACAGTAATAACAGCCTGTCTGAAATGACACACTTCAGGCCACAGCTCCA<br>TCACAGTGGGGACATGGTATTTACCCCTGAGTCAGGCCTCCAATTAAGATTAAA<br>TGAGAAACTGGGGACAACTGCAGCAACAGAGTTGAAGAAACTTGATTTCAAAGT<br>TTCTAGTACATCAAATAATCTGATTTCAACAATTCCATCAGACAATTTGGCAGCA<br>GGTACTGATAATACAAGTTCCTTAGGACCCCCAAGTATGCCAGTTCATTATGAT<br>AGTCAATTAGATACCACTCTATTTGGCAAAAAGTCATCTCCCCTTACTGAGTCTG<br>GTGGACCTCTGAGCTTGAGTGAAGAAAATAATGATTCAAAGTTGTTAGAATCAG<br>GTTTAATGAATAGCCAAGAAGTTCATGGGGAAAAAATGTATCGACGCGTAGCT<br>TTCAAAAGAAAACGACACTATTTTATTGCTGCAGTGGAGAGGCTCTGGGATT<br>ATGGGATGAGTAGCTCCCCACATGTTCTAAGAAACAGGGCTCAGAGTGGCAGT<br>GTCCCTCAGTTCAAGAAAGTTGTTTTCCAGGAATTTACTGATGGCTCCTTTACTC<br>AGCCCTTATACCGTGGAGAACTAAATGAACATTTGGGACTCCTGGGGCCATATA<br>TAAGAGCAGAAGTTGAAGATAATATCATGGTAACTTTCAGAAATCAGGCCTCTC<br>GTCCCTATTCCTTCTATTCTAGCCTTATTTCTTATGAGGAAGATCAGAGGCAAG<br>GAGCAGAACCTAGAAAAACTTTGTCAAGCCTAATGAAACCAAAACTTACTTTT<br>GGAAAGTGCAACATCATATGGCACCCACTAAAGATGAGTTTGACTGCAAAGCCT<br>GGGCTTATTTCTCTGATGTTGACCTGGAAAAAGATGTGCACTCAGGCCTGATTG<br>GACCCCTTCTGGTCTGCCACACTAACACACTGAACCCTGCTCATGGGAGACAA<br>GTGACAGTACAGGAATTTGCTCTGTTTTTCACCATCTTTGATGAGACCAAAAGC<br>TGGTACTTCACTGAAAATATGGAAAGAAACTGCAGGGCTCCCTGCAATATCCAG<br>ATGGAAGATCCCACTTTTAAAGAGAATTATCGCTTCCATGCAATCAATGGCTAC<br>ATAATGGATACACTACCTGGCTTAGTAATGGCTCAGGATCAAAGGATTCGATGG<br>TATCTGCTCAGCATGGGCAGCAATGAAAACATCCATTCTATTCATTTCAGTGGA<br>CATGTGTTCACTGTACGAAAAAAGAGGGAGTATAAAATGGCACTGTACAATCTC<br>TATCCAGGTGTTTTTGAGACAGTGGAAATGTTACCATCCAAAGCTGGAATTTGG<br>CGGGTGGAATGCCTTATTGGCGAGCATCTACATGCTGGGATGAGCACACTTTT<br>TCTGGTGTACAGCAATAAGTGTCAGACTCCCCTGGGAATGGCTTCTGGACACA | SEQ ID<br>NO: 13 | FVIII-N6 |

TABLE I-continued

| | |
|---|---|
| TTAGAGATTTTCAGATTACAGCTTCAGGACAATATGGACAGTGGGCCCCAAAGC<br>TGGCCAGACTTCATTATTCCGGATCAATCAATGCCTGGAGCACCAAGGAGCCC<br>TTTTCTTGGATCAAGGTGGATCTGTTGGCACCAATGATTATTCACGGCATCAAG<br>ACCCAGGGTGCCCGTCAGAAGTTCTCCAGCCTCTACATCTCTCAGTTTATCATC<br>ATGTATAGTCTTGATGGGAAGAAGTGGCAGACTTATCGAGGAAATTCCACTGGA<br>ACCTTAATGGTCTTCTTTGGCAATGTGGATTCATCTGGGATAAAACACAATATTT<br>TTAACCCTCCAATTATTGCTCGATACATCCGTTTGCACCCAACTCATTATAGCAT<br>TCGCAGCACTCTTCGCATGGAGTTGATGGGCTGTGATTTAAATAGTTGCAGCAT<br>GCCATTGGGAATGGAGAGTAAAGCAATATCAGATGCACAGATTACTGCTTCATC<br>CTACTTTACCAATATGTTTGCCACCTGGTCTCCTTCAAAAGCTCGACTTCACCTC<br>CAAGGGAGGAGTAATGCCTGGAGACCTCAGGTGAATAATCCAAAAGAGTGGCT<br>GCAAGTGGACTTCCAGAAGACAATGAAAGTCACAGGAGTAACTACTCAGGGAG<br>TAAAATCTCTGCTTACCAGCATGTATGTGAAGGAGTTCCTCATCTCCAGCAGTC<br>AAGATGGCCATCAGTGGACTCTCTTTTTTCAGAATGGCAAAGTAAAGGTTTTTC<br>AGGGAAATCAAGACTCCTTCACACCTGTGGTGAACTCTCTAGACCCACCGTTAC<br>TGACTCGCTACCTTCGAATTCACCCCCAGAGTTGGGTGCACCAGATTGCCCTG<br>AGGATGGAGGTTCTGGGCTGCGAGGCACAGGACCTCTACTGA | |
| ATGCAAATAGAGCTCTCCACCTGCTTCTTTCTGTGCCTTTTGCGATTCTGCTTTA<br>GTGCCACCAGAAGATACTACCTGGGTGCAGTGGAACTGTCATGGGACTATATG<br>CAAAGTGATCTCGGTGAGCTGCCTGTGGACGCAAGATTTCCTCCTAGAGTGCC<br>AAAATCTTTTCCATTCAACACCTCAGTCGTGTACAAAAAGACTCTGTTTGTAGAA<br>TTCACGGATCACCTTTTCAACATCGCTAAGCCAAGGCCACCCTGGATGGGTCT<br>GCTAGGTCCTACCATCCAGGCTGAGGTTTATGATACAGTGGTCATTACACTTAA<br>GAACATGGCTTCCCATCCTGTCAGTCTTCATGCTGTTGGTGTATCCTACTGGAA<br>AGCTTCTGAGGGAGCTGAATATGATGATCAGACCAGTCAAAGGGAGAAAGAAG<br>ATGATAAAGTCTTCCCTGGTGGAAGCCATACATATGTCTGGCAGGTCCTGAAAG<br>AGAATGGTCCAATGGCCTCTGACCCACTGTGCCTTACCTACTCATATCTTTCTC<br>ATGTGGACCTGGTAAAAGACTTGAATTCAGGCCTCATTGGAGCCCTACTAGTAT<br>GTAGAGAAGGGAGTCTGGCCAAGGAAAAGACACAGACCTTGCACAAATTTATA<br>CTACTTTTTGCTGTATTTGATGAAGGGAAAAGTTGGCACTCAGAAACAAAGAAC<br>TCCTTGATGCAGGATAGGGATGCTGCATCTGCTCGGGCCTGGCCTAAATGCA<br>CACAGTCAATGGTTATGTAAACAGGTCTCTGCCAGGTCTGATTGGATGCCACA<br>GGAAATCAGTCTATTGGCATGTGATTGGAATGGGCACCACTCCTGAAGTGCAC<br>TCAATATTCCTCGAAGGTCACACATTTCTTGTGAGGAACCATCGCCAGGCGTCC<br>TTGGAAATCTCGCCAATAACTTTCCTTACTGCTCAAACACTCTTGATGGACCTTG<br>GACAGTTTCTACTGTTTTGTCATATCTCTTCCCACCAACATGATGGCATGGAAG<br>CTTATGTCAAAGTAGACAGCTGTCCAGAGGAACCCCAACTACGAATGAAAAATA<br>ATGAAGAAGCGGAAGACTATGATGATGATCTTACTGATTGTGAAATGGATGTGG<br>TCAGGTTTGATGATGACAACTCTCCTTCCTTTATCCAAATTCGCTCAGTTGCCAA<br>GAAGCATCCTAAAACTTGGGTACATTACATTGCTGCTGAAGAGGAGGACTGGG<br>ACTATGCTCCCTTAGTCCTCGCCCCCGATGACAGAAGTTATAAAAGTCAATATT<br>TGAACAATGGCCCTCAGCGGATTGTAGGAAGTACAAAAAAGTCCGATTTATG<br>GCATACACAGATGAAACCTTTAAGACTCGTGAAGCTATTCAGCATGAATCAGGA<br>ATCTTGGGACCTTTACTTTATGGGGAAGTTGGAGACACACTGTTGATTATATTA<br>AGAATCAAGCAAGCAGACCATATAACATCTACCCTCACGGAATCACTGATGTCC<br>GTCCTTTGTATTCAAGGAGATTACCAAAAGGTGTAAAACATTTGAAGGATTTTCC<br>AATTCTGCCAGGAGAAATATTCAAATATAAATGGACAGTGACTGTAGAAGATGG<br>GCCAACTAAATCAGATCCTCGGTGCCTGACCCGCTATTACTCTAGTTTCGTTAA<br>TATGGAGAGAGATCTAGCTTCAGGACTCATTGGCCCTCTCCTCATCTGCTACAA<br>AGAATCTGTAGATCAAAGAGGAAACCAGATAATGTCAGACAAGAGGAATGTCAT<br>CCTGTTTTCTGTATTTGATGAGAACCGAAGCTGGTACCTCACAGAGAATATACA<br>ACGCTTTCTCCCCAATCCAGCTGGAGTGCAGCTTGAGGATCCAGAGTTCCAAG<br>CCTCCAACATCATGCACAGCATCAATGGCTATGTTTTTGATAGTTTGCAGTTGT<br>CAGTTTGTTTGCATGAGGTGGCATACTGGTACATTCTAAGCATTGGAGCACAGA<br>CTGACTTCCTTTCTGTCTTCTTCTCTGGATATACCTTCAAACACAAAATGGTCTA<br>TGAAGACACACTCACCCTATTCCCATTCTCAGGAGAAACTGTCTTCATGTCGAT<br>GGAAAACCCAGGTCTATGGATTCTGGGGTGCCACAACTCAGACTTTCGGAACA<br>GAGGCATGACCGCCTTACTGAAGGTTTCTAGTTGTGACAAGAACACTGGTGATT<br>ATTACGAGGACAGTTATGAAGATATTTCAGCATACTTGCTGAGTAAAAACAATG<br>CCATTGAACCAAGAAGCTTCTCCCAAAACCCACCAGTCTTGAAACACCATCAAC<br>GGGAAATAACTCGTACTACTCTTCAGTCAGATCAAGAGGAAATTGACTATGATG<br>ATACCATATCAGTTGAAATGAAGAAGGAAGATTTTGACATTTATGATGAGGATG<br>AAAATCAGAGCCCCCGCAGCTTTCAAAAGAAAACACGACACTATTTATTGCTG<br>CAGTGGAGAGGCTCTGGGATTATGGGATGAGTAGCTCCCCACATGTTCTAAGA<br>AACAGGGCTCAGAGTGGCAGTGTCCCTCAGTTCAAGAAAGTTGTTTTCCAGGA<br>ATTTACTGATGGCTCCTTTACTCAGCCCTTATACCGTGGAGAACTAAATGAACA<br>TTTGGGACTCCTGGGGCCATATATAAGAGCAGAAGTTGAAGATAATATCATGGT<br>AACTTTCAGAAATCAGGCCTCTCGTCCCTATTCCTTCTATTCTAGCCTTATTTCT<br>TATGAGGAAGATCAGAGGCAAGGAGCAGAACCTAGAAAAAACTTTGTCAAGCC<br>TAATGAAACCAAAACTTACTTTTGGAAAGTGCAACATCATATGGCACCCACTAA<br>GATGAGTTTGACTGCAAAGCCTGGGCTTATTTCTCTGATGTTGACCTGGAAAAA<br>GATGTGCACTCAGGCCTGATTGGACCCCTTCTGGTCTGCCACACTAACACACT<br>GAACCCTGCTCATGGGAGACAAGTGACAGTACAGGAATTTGCTCTGTTTTTCAC<br>CATCTTTGATGAGACCAAAAGCTGGTACTTCACTGAAAATATGGAAAGAAACTG<br>CAGGGCTCCCTGCAATATCCAGATGGAAGATCCCACTTTTAAAGAGAATTATCG<br>CTTCCATGCAATCAATGGCTACATAATGGATACACTACCTGGCTTAGTAATGGC<br>TCAGGATCAAAGGATTCGATGGTATCTGCTCAGCATGGGCAGCAATGAAAACA<br>TCCATTCTATTCATTTCAGTGGACATGTGTTCACCGTACGAAAAAAAGAGGAGT<br>ATAAAATGGCACTGTACAATCTCTATCCAGGTGTTTTTGAGACAGTGGAAATGT | SEQ ID FVIII-RH<br>NO: 14 |

TABLE I-continued

| | | |
|---|---|---|
| TACCATCCAAAGCTGGAATTTGGCGGGTGGAATGCCTTATTGGCGAGCATCTA<br>CATGCTGGGATGAGCACACTTTTTCTGGTGTACAGCAATAAGTGTCAGACTCCC<br>CTGGGAATGGCTTCTGGACACATTAGAGATTTTCAGATTACAGCTTCAGGACAA<br>TATGGACAGTGGGCCCCAAAGCTGGCCAGACTTCATTATTCCGGATCAATCAAT<br>GCCTGGAGCACCAAGGAGCCCTTTTCTTGGATCAAGGTGGATCTGTTGGCACC<br>AATGATTATTCACGGCATCAAGACCCAGGGTGCCCGTCAGAAGTTCTCCAGCC<br>TCTACATCTCTCAGTTTATCATCATGTATAGTCTTGATGGGAAGAAGTGGCAGA<br>CTTATCGAGGAAATTCCACTGGAACCTTAATGGTCTTCTTTGGCAATGTGGATT<br>CATCTGGGATAAAACACAATATTTTTAACCCTCCAATTATTGCTCGATACATCCG<br>TTTGCACCCAACTCATTATAGCATTCGCAGCACTCTTCGCATGGAGTTGATGGG<br>CTGTGATTTAAATAGTTGCAGCATGCCATTGGGAATGGAGAGTAAAGCAATATC<br>AGATGCACAGATTACTGCTTCATCCTACTTTACCAATATGTTTGCCACCTGGTCT<br>CCTTCAAAAGCTCGACTTCACCTCCAAGGGAGGAGTAATGCCTGGAGACCTCA<br>GGTGAATAATCCAAAAGAGTGGCTGCAAGTGGACTTCCAGAAGACAATGAAAG<br>TCACAGGAGTAACTACTCAGGGAGTAAAATCTCTGCTTACCAGCATGTATGTGA<br>AGGAGTTCCTCATCTCCAGCAGTCAAGATGGCCATCAGTGGACTCTCTTTTTTC<br>AGAATGGCAAAGTAAAGGTTTTTCAGGGAAATCAAGACTCCTTCACACCTGTGG<br>TGAACTCTCTAGACCCACCGTTACTGACTCGCTACCTTCGAATTCACCCCCAGA<br>GTTGGGTGCACCAGATTGCCCTGAGGATGGAGGTTCTGGGCTGCGAGGCACA<br>GGACCTCTACTGA | | |
| ATGCAGATCGAGCTGTCCACCTGCTTTTTTCTGTGCCTGCTGCGGTTCTGCTTC<br>AGCGCCACCCGGCGGTACTACCTGGGCGCCGTGGAGCTGTCCTGGGACTACA<br>TGCAGAGCGACCTGGGCGAGCTGCCCGTGGACGCCCGGTTCCCCCCCAGAGT<br>GCCCAAGAGCTTCCCCTTCAACACCAGCGTGGTGTACAAGAAAACCCTGTTCG<br>TGGAGTTCACCGACCACCTGTTCAATATCGCCAAGCCCAGGCCCCCCTGGATG<br>GGCCTGCTGGGCCCCACCATCCAGGCCGAGGTGTACGACACCGTGGTGATCA<br>CCCTGAAGAACATGGCCAGCCACCCCGTGAGCCTGCACGCCGTGGGCGTGAG<br>CTACTGGAAGGCCAGCGAGGGCGCCGAGTACGACGACCAGACCAGCCAGCG<br>GGAGAAGAAGATGACAAGGTGTTCCCTGGCGGCAGCCACACCTACGTGTGG<br>CAGGTGCTGAAAGAAAACGGCCCCATGGCCTCCGACCCCCTGTGCCTGACCT<br>ACAGCTACCTGAGCCACGTGGACCTGGTGAAGGACCTGAACAGCGGCCTGAT<br>CGGCGCTCTGCTCGTCTGCCGGGAGGGCAGCCTGGCCAAAGAGAAAACCCAG<br>ACCCTGCACAAGTTCATCCTGCTGTTCGCCGTGTTCGACGAGGGCAAGAGCTG<br>GCACAGCGAGACAAAGAACAGCCTGATGCAGGACCGGGACGCCGCCTCTGCC<br>AGAGCCTGGCCCAAGATGCACACCGTGAACGGCTACGTGAACAGAAGCCTGC<br>CCGGCCTGATTGGCTGCCACCGGAAGAGCGTGTACTGGCACGTGATCGGCAT<br>GGGCACCACACCCGAGGTGCACAGCATCTTTCTGGAAGGGCACACCTTTCTGG<br>TCCGGAACCACCGGCAGGCCAGCCTGGAAATCAGCCCTATCACCTTCCTGACC<br>GCCCAGACACTGCTGATGGACCTGGGCCAGTTCCTGCTGTTTTGCCACATCAG<br>CTCTCACCAGCACGACGGCATGGAAGCCTACGTGAAGGTGGACTCTTGCCCC<br>GAGGAACCCCAGCTGCGGATGAAGAACAACGAGGAAGCCGAGGACTACGACG<br>ACGACCTGACCGACAGCGAGATGGACGTGGTGCGGTTCGACGACGACAACAG<br>CCCCAGCTTCATCCAGATCAGAAGCGTGGCCAAGAAGCACCCCAAGACCTGG<br>GTGCACTATATCGCCGCCGAGGAAGAGGACTGGGACTACGCCCCCCTGGTGC<br>TGGCCCCCGACGACAGAAGCTACAAGAGCCAGTACCTGAACAATGGCCCCCA<br>GCGGATCGGCCGGAAGTACAAGAAAGTGCGGTTCATGGCCTACACCGACGAG<br>ACATTCAAGACCCGGGAGGCCATCCAGCACGAGAGCGGCATCCTGGGCCCCC<br>TGCTGTACGGCGAAGTGGGCGACACACTGCTGATCATCTTCAAGAACCAGGCT<br>AGCCGGCCCTACAACATCTACCCCCACGGCATCACCGACGTGCGGCCCCTGT<br>ACAGCAGGCGGCTGCCCAAGGGCGTGAAGCACCTGAAGGACTTCCCCATCCT<br>GCCCGGCGAGATCTTCAAGTACAAGTGGACCGTGACCGTGGAGGACGGCCCC<br>ACCAAGAGCGACCCCAGATGCCTGACCCGGTACTACAGCAGCTTCGTGAACAT<br>GGAACGGGACCTGGCCTCCGGGCTGATCGGACCTCTGCTGATCTGCTACAAA<br>GAAAGCGTGGACCAGCGGGCAACCAGATCATGAGCGACAAGCGGAACGTGA<br>TCCTGTTCAGCGTGTTCGATGAGAACCGGTCCTGGTATCTGACCGAGAACATC<br>CAGCGGTTTCTGCCCAACCCTGCCGGCGTGCAGCTGGAAGATCCCGAGTTCC<br>AGGCCAGCAACATCATGCACTCCATCAATGGCTACGTGTTCGACTCTCTGCAG<br>CTCTCCGTGTGTCTGCACGAGGTGGCCTACTGGTACATCCTGAGCATCGGCGC<br>CCAGACCGACTTCCTGAGCGTGTTCTTCAGCGGCTACACCTTCAAGCACAAGA<br>TGGTGTACGAGGACACCCTGACCCTGTTCCCTTTCAGCGGCGAGACAGTGTTC<br>ATGAGCATGGAAAACCCCGGCCTGTGGATTCTGGGCTGCCACAACAGCGACTT<br>CCGGAACCGGGGCATGACCGCCCTGCTGAAGGTGTCCAGCTGCGACAAGAAC<br>ACCGGCGACTACTACGAGGACAGCTACGAGGATATCAGCGCCTACCTGCTGTC<br>CAAGAACAACGCCATCGAACCCCGGAGCTTCAGCCAGAACCCCCCCGTGCTG<br>ACGCGTCACCAGCGGGAGATCACCCGGACAACCCTGCAGTCCGACCAGGAAG<br>AGATCGATTACGACGACACCATCAGCGTGGAGATGAAGAAGGAGGATTTCGAT<br>ATCTACGACGAGGACGAGAACCAGAGCCCCAGAAGCTTCCAGAAGAAAACCC<br>GGCACTACTTCATTGCCGCCGTGGAGAGGCTGTGGGACTACGGCATGAGTTCT<br>AGCCCCCACGTGCTGCGGAACCGGGCCCAGAGCGGCAGCGTGCCCCAGTTC<br>AAGAAAGTGGTGTTCCAGGAATTCACAGACGGCAGCTTCACCCAGCCTCTGTA<br>TAGAGGCGAGCTGAACGAGCACCTGGGCTGCTGGGCCCTACATCAGGGCC<br>GAAGTGGAGGACAACATCATGGTGACCTTCCGGAATCAGGCCAGCAGACCCTA<br>CTCCTTCTACAGCAGCCTGATCAGCTACGAAGAGGACCAGCGGCAGGGCGCC<br>GAACCCCGAAGAACTTCGTGAAGCCCAACGAAACCAAGACCTACTTCTGGAA<br>AGTGCAGCACCACATGGCCCCCACCAAGGACGAGTTCGACTGCAAGGCCTGG<br>GCCTACTTCAGCGACGTGGATCTGGAAAAGGACGTGCACTCTGGACTGATTGG<br>CCCACTCCTGGTCTGCCACACTAACACCCTCAACCCCGCCCACGGCCGCCAG<br>GTGACCGTGCAGGAATTCGCCCTGTTCTTCACCATCTTCGACGAGACAAAGTC<br>CTGGTACTTCACCGAGAATATGGAACGGAACTGCAGAGCCCCCTGCAACATCC | SEQ ID<br>NO: 15 | Codon<br>Optimized<br>(CO) FVIII |

TABLE I-continued

```
AGATGGAAGATCCTACCTTCAAAGAGAACTACCGGTTCCACGCCATCAACGGC
TACATCATGGACACCCTGCCTGGCCTGGTGATGGCCCAGGACCAGAGAATCC
GGTGGTATCTGCTGTCCATGGGCAGCAACGAGAATATCCACAGCATCCACTTC
AGCGGCCACGTGTTCACCGTGCGGAAGAAAGAAGAGTACAAGATGGCCCTGT
ACAACCTGTACCCCGGCGTGTTCGAGACAGTGGAGATGCTGCCCAGCAAGGC
CGGCATCTGGCGGGTGGAGTGTCTGATCGGCGAGCACCTGCACGCTGGCATG
AGCACCCTGTTTCTGGTGTACAGCAACAAGTGCCAGACCCCACTGGGCATGGC
CTCTGGCCACATCCGGGACTTCCAGATCACCGCCTCCGGCCAGTACGGCCAG
TGGGCCCCCAAGCTGGCCAGACTGCACTACAGCGGCAGCATCAACGCCTGGT
CCACCAAAGAGCCCTTCAGCTGGATCAAGGTGGACCTGCTGGCCCCTATGATC
ATCCACGGCATTAAGACCCAGGGCGCCAGGCAGAAGTTCAGCAGCCTGTACAT
CAGCCAGTTCATCATCATGTACAGCCTGGACGGCAAGAAGTGGCAGACCTACC
GGGGCAACAGCACCGGCACCCTGATGGTGTTCTTCGGCAATGTGGACAGCAG
CGGCATCAAGCACAACATCTTCAACCCCCCCATCATTGCCCGGTACATCCGGC
TGCACCCCACCCACTACAGCATTAGATCCACACTGAGAATGGAACTGATGGGC
TGCGACCTGAACTCCTGCAGCATGCCTCTGGGCATGGAAAGCAAGGCCATCAG
CGACGCCCAGATCACAGCCAGCAGCTACTTCACCAACATGTTCGCCCACCTGGT
CCCCCTCCAAGGCCAGGCTGCACCTGCAGGGCGGTCCAACGCCTGGCGGC
CTCAGGTCAACAACCCCAAAGAATGGCTGCAGGTGGACTTTCAGAAAACCATG
AAGGTGACCGGCGTGACCACCCAGGGCGTGAAAAGCCTGCTGACCAGCATGT
ACGTGAAAGAGTTTCTGATCAGCAGCTCTCAGGATGGCCACCAGTGGACCCTG
TTCTTTCAGAACGGCAAGGTGAAAGTGTTCCAGGGCAACCAGGACTCCTTCAC
CCCCGTGGTGAACTCCCTGGACCCCCCCCTGCTGACCCGCTACCTGAGAATC
CACCCCCAGTCTTGGGTGCACCAGATCGCCCTCAGGATGGAAGTCCTGGGAT
GTGAGGCCCAGGATCTGTACTGATGA
```

| | SEQ ID NO: 16 | CO FVIII-RH |
|---|---|---|

```
ATGCAGATCGAGCTGTCCACCTGCTTTTTTCTGTGCCTGCTGCGGTTCTGCTTC
AGCGCCACCCGGCGGTACTACCTGGGCGCCGTGGAGCTGTCCTGGGACTACA
TGCAGAGCGACCTGGGCGAGCTGCCCGTGGACGCCCGGTTCCCCCCCAGAGT
GCCCAAGAGCTTCCCCTTCAACACCAGCGTGGTGTACAAGAAAACCCTGTTCG
TGGAGTTCACCGACCACCTGTTCAATATCGCCAAGCCCAGGCCCCCCTGGATG
GGCCTGCTGGGCCCCACCATCCAGGCCGAGGTGTACGACACCGTGGTGATCA
CCCTGAAGAACATGGCCAGCCACCCCGTGAGCCTGCACGCCGTGGGCGTGAG
CTACTGGAAGGCCAGCGAGGGCGCCGAGTACGACGACCAGACCAGCCAGCG
GGAGAAAGAAGATGACAAGGTGTTCCCTGGCGGCAGCCACACCTACGTGTGG
CAGGTGCTGAAAGAAAACGGCCCCATGGCCTCCGACCCCCTGTGCCTGACCT
ACAGCTACCTGAGCCACGTGGACCTGGTGAAGGACCTGAACAGCGGCCTGAT
CGGCGCTCTGCTCGTCTGCCGGGAGGGCAGCCTGGCCAAAGAGAAAACCCAG
ACCCTGCACAAGTTCATCCTGCTGTTCGCCGTGTTCGACGAGGGCAAGAGCTG
GCACAGCGAGACAAAGAACAGCCTGATGCAGGACCGGGACGCCGCCTCTGCC
AGAGCCTGGCCCAAGATGCACACCGTGAACGGCTACGTGAACAGAAGCCTGC
CCGGCCTGATTGGCTGCCACCGGAAGAGCGTGTACTGGCACGTGATCGGCAT
GGGCACCACACCCGAGGTGCACAGCATCTTTCTGGAAGGGCACACCTTTCTGG
TCCGGAACCACCGGCAGGCCAGCCTGGAAATCAGCCCTATCACCTTCCTGACC
GCCCAGACACTGCTGATGGACCTGGGCCAGTTCCTGCTGTTTTGCCACATCAG
CTCTCACCAGCACGACGGCATGGAAGCCTACGTGAAGGTGGACTCTTGCCCC
GAGGAACCCCAGCTGCGGATGAAGAACAACGAGGAAGCCGAGGACTACGACG
ACGACCTGACCGACAGCGAGATGGACGTGGTGCGGTTCGACGACGACAACAG
CCCCAGCTTCATCCAGATCAGAAGCGTGGCCAAGAAGCACCCCAAGACCTGG
GTGCACTATATCGCCGCCGAGGAAGAGGACTGGGACTACGCCCCCCTGGTGC
TGGCCCCCGACGACAGAAGCTACAAGAGCCAGTACCTGAACAATGGCCCCCA
GCGGATCGGCCGGAAGTACAAGAAAGTGCGGTTCATGGCCTACACCGACGAG
ACATTCAAGACCCGGGAGGCCATCCAGCACGAGAGCGGCATCCTGGGCCCCC
TGCTGTACGGCGAAGTGGGCGACACACTGCTGATCATCTTCAAGAACCAGGCT
AGCCGGCCCTACAACATCTACCCCCACGGCATCACCGACGTGCGGCCCCTGT
ACAGCAGGCGGCTGCCCAAGGGCGTGAAGCACCTGAAGGACTTCCCCATCCT
GCCCGGCGAGATCTTCAAGTACAAGTGGACCGTGACCGTGGAGGACGGCCCC
ACCAAGAGCGACCCCAGATGCCTGACCCGGTACTACAGCAGCTTCGTGAACAT
GGAACGGGACCTGGCCTCCGGGCTGATCGGACCTCTGCTGATCTGCTACAAA
GAAAGCGTGGACCAGCGGGCAACCAGATCATGAGCGACAAGCGGAACGTGA
TCCTGTTCAGCGTGTTCGATGAGAACCGGTCCTGGTATCTGACCGAGAACATC
CAGCGGTTTCTGCCCAACCCTGCCGGCGTGCAGCTGGAAGATCCCGAGTTCC
AGGCCAGCAACATCATGCACTCCATCAATGGCTACGTGTTCGACTCTCTGCAG
CTCTCCGTGTGTCTGCACGAGGTGGCCTACTGGTACATCCTGAGCATCGGCGC
CCAGACCGACTTCCTGAGCGTGTTCTTCAGCGGCTACACCTTCAAGCACAAGA
TGGTGTACGAGGACACCCTGACCCTGTTCCCCTTCAGCGGCGAGACAGTGTTC
ATGAGCATGGAAAACCCCGGCCTGTGGATTCTGGGCTGCCACAACAGCGACTT
CCGGAACCGGGGCATGACCGCCCTGCTGAAGGTGTCCAGCTGCGACAAGAAC
ACCGGCGACTACTACGAGGACAGCTACGAGGATATCAGCGCCTACCTGCTGTC
CAAGAACAACGCCATCGAACCCCGGAGCTTCAGCCAGAACCCCCCCGTGCTG
ACGCATCACCAGCGGGAGATCACCCGGACAACCCTGCAGTCCGACCAGGAAG
AGATCGATTACGACGACACCATCAGCGTGGAGATGAAGAAAGAGGATTTCGAT
ATCTACGACGAGGACGAGAACCAGAGCCCCAGAAGCTTCCAGAAGAAAACCC
GGCACTACTTCATTGCCGCCGTGGAGAGGCTGTGGGACTACGGCATGAGTTCT
AGCCCCCACGTGCTGCGGAACCGGGCCCAGAGCGGCAGCGTGCCCCAGTTC
AAGAAAGTGGTGTTCCAGGAATTCACAGACGGCAGCTTCACCCAGCCTCTGTA
TAGAGGCGAGCTGAACGAGCACCTGGGCTGCTGGGCCCTACATCAGGGCC
GAAGTGGAGGACAACATCATGGTGACCTTCCGGAATCAGGCCAGCAGACCCTA
CTCCTTCTACAGCAGCCTGATCAGCTACGAAGAGGACCAGCGGCAGGGCGCC
GAACCCCGGAAGAACTTCGTGAAGCCCAACGAAACCAAGACCTACTTCTGGAA
```

TABLE I-continued

```
AGTGCAGCACCACATGGCCCCCACCAAGGACGAGTTCGACTGCAAGGCCTGG
GCCTACTTCAGCGACGTGGATCTGGAAAAGGACGTGCACTCTGGACTGATTGG
CCCACTCCTGGTCTGCCACACTAACACCCTCAACCCCGCCCACGGCCGCCAG
GTGACCGTGCAGGAATTCGCCCTGTTCTTCACCATCTTCGACGAGACAAAGTC
CTGGTACTTCACCGAGAATATGGAACGGAACTGCAGAGCCCCCTGCAACATCC
AGATGGAAGATCCTACCTTCAAAGAGAACTACCGGTTCCACGCCATCAACGGC
TACATCATGGACACCCTGCCTGGCCTGGTGATGGCCCAGGACCAGAGAATCC
GGTGGTATCTGCTGTCCATGGGCAGCAACGAGAATATCCACAGCATCCACTTC
AGCGGCCACGTGTTCACCGTGCGGAAGAAAGAAGAGTACAAGATGGCCCTGT
ACAACCTGTACCCCGGCGTGTTCGAGACAGTGGAGATGCTGCCCAGCAAGGC
CGGCATCTGGCGGGTGGAGTGTCTGATCGGCGAGCACCTGCACGCTGGCATG
AGCACCCTGTTTCTGGTGTACAGCAACAAGTGCCAGACCCCACTGGGCATGGC
CTCTGGCCACATCCGGGACTTCCAGATCACCGCCTCCGGCCAGTACGGCCAG
TGGGCCCCCAAGCTGGCCAGACTGCACTACAGCGGCAGCATCAACGCCTGGT
CCACCAAAGAGCCCTTCAGCTGGATCAAGGTGGACCTGCTGGCCCCCTATGATC
ATCCACGGCATTAAGACCCAGGGCGCCAGGCAGAAGTTCAGCAGCCTGTACAT
CAGCCAGTTCATCATCATGTACAGCCTGGACGGCAAGGAAGTGGCAGACCTACC
GGGGCAACAGCACCGGCACCCTGATGGTGTTCTTCGGCAATGTGGACAGCAG
CGGCATCAAGCACAACATCTTCAACCCCCCCATCATTGCCCGGTACATCCGGC
TGCACCCCACCCACTACAGCATTAGATCCACACTGAGAATGGAACTGATGGGC
TGCGACCTGAACTCCTGCAGCATGCCTCTGGGCATGGAAAGCAAGGCCATCAG
CGACGCCCAGATCACAGCCAGCAGCTACTTCACCAACATGTTCGCCACCTGGT
CCCCCTCCAAGGCCAGGCTGCACCTGCAGGGCCGGTCCAACGCCTGGCGGC
CTCAGGTCAACAACCCCAAAGAATGGCTGCAGGTGGACTTTCAGAAAACCATG
AAGGTGACCGGCGTGACCACCCAGGGCGTGAAAAGCCTGCTGACCAGCATGT
ACGTGAAAGAGTTTCTGATCAGCAGCTCTCAGGATGGCCACCAGTGGACCCTG
TTCTTTCAGAACGGCAAGGTGAAAGTGTTCCAGGGCAACCAGGACTCCTTCAC
CCCCGTGGTGAACTCCCTGGACCCCCCCCTGCTGACCCGCTACCTGAGAATC
CACCCCCAGTCTTGGGTGCACCAGATCGCCCTCAGGATGAAGTCCTGGGAT
GTGAGGCCCAGGATCTGTACTGATGA
```

| | |
|---|---|
| ATGCAGCGCGTGAACATGATCATGGCAGAATCACCAGGCCTCATCACCATCTG<br>CCTTTTAGGATATCTACTCAGTGCTGAATGTACAGTTTTTCGTTGATCATGAAAAC<br>GCCAACAAAATTCTGAATCGGCAAAGAGGTATAATTCAGGTAAATTGGAAGAG<br>TTTGTTCAAGGGAACCTTGAGAGAGAATGTATGGAAGAAAAGTGTAGTTTTGAA<br>GAAGCACGAGAAGTTTTTGAAAACACTGAAAGAACAACTGAATTTTGGAAGCAG<br>TATGTTGATGTAACATGTAACATTAAGAATGGCAGATGCGAGCAGTTTTGTAAA<br>AATAGTGCTGATAACAAGGTGGTTTGCTCCTGTACTGAGGGATATCGACTTGCA<br>GAAAACCAGAAGTCCTGTGAACCAGCAGTGCCATTTCCATGTGGAAGAGTTTCT<br>GTTTCACAAACTTCTAAGCTCACCCGTGCTGAGACTGTTTTTCCTGATGTGGAC<br>TATGTAAATTCTACTGAAGCTGAAACCATTTTGGATAACATCACTCAAAGCACCC<br>AATCATTTAATGACTTCACTCGGGTTGTTGGTGGAGAAGATGCCAAACCAGGTC<br>AATTCCCTTGGCAGGTTGTTTGAATGGTAAAGTTGATGCATTCTGTGGAGGCT<br>CTATCGTTAATGAAAAATGGATTGTAACTGCTGCCCACTGTGTTGAAACTGGTG<br>TTAAAATTACAGTTGTCGCAGGTGAACATAATATTGAGGAGACAGAACATACAG<br>AGCAAAAGCGAAATGTGATTCGAATTATTCCTCACCACAACTACAATGCAGCTA<br>TTAATAAGTACAACCATGACATTGCCCTTCTGGAACTGGACGAACCCTTAGTGC<br>TAAACAGCTACGTTACACCTATTTGCATTGCTGACAAGGAATACACGAACATCT<br>TCCTCAAATTTGGATCTGGCTATGTAAGTGGCTGGGGAAGAGTCTTCCACAAAG<br>GGAGATCAGCTTTAGTTCTTCAGTACCTTAGAGTTCCACTTGTTGACCGAGCCA<br>CATGTCTTCGATCTACAAAGTTCACCATCTATAACAACATGTTCTGTGCTGGCTT<br>CCATGAAGGAGGTAGAGATTCATGTCAAGGAGATAGTGGGGGACCCCATGTTA<br>CTGAAGTGGAAGGGACCAGTTTCTTAACTGGAATTATTAGCTGGGGTGAAGAG<br>TGTGCAATGAAAGGCAAATATGGAATATATACCAAGGTATCCCGGTATGTCAAC<br>TGGATTAAGGAAAAAACAAAGCTCACTTAA | SEQ ID<br>NO: 17 FIX |
| ATGGTCTCCCAGGCCCTCAGGCTCCTCTGCCTTCTGCTTGGGCTTCAGGGCTG<br>CCTGGCTGCAGGCGGGGTCGCTAAGGCCTCAGGAGGAGAAACACGGGACATG<br>CCGTGGAAGCCGGGGCCTCACAGAGTCTTCGTAACCCAGGAGGAAGCCCACG<br>GCGTCCTGCACCGGCGCCGGCGCGCCAACGCGTTCCTGGAGGAGCTGCGGC<br>CGGGCTCCCTGGAGAGGGAGTGCAAGGAGGAGCAGTGCTCCTTCGAGGAGG<br>CCCGGGAGATCTTCAAGGACGCGGAGAGGACGAAGCTGTTCTGGATTCTTAC<br>AGTGATGGGGACCAGTGTGCCTCAAGTCCATGCCAGAATGGGGGCTCCTGCA<br>AGGACCAGCTCCAGTCCTATATCTGCTTCTGCCTCCCTGCCTTCGAGGGCCGG<br>AACTGTGAGACGCACAAGGATGACCAGCTGATCTGTGTGAACGAGAACGGCG<br>GCTGTGAGCAGTACTGCAGTGACCACACGGGCACCAAGCGCTCCTGTCGGTG<br>CCACGAGGGGTACTCTCTGCTGGCAGACGGGGTGTCCTGCACACCCACAGTT<br>GAATATCCATGTGGAAAAATACCTATTCTAGAAAAAAGAAATGCCAGCAAACCC<br>CAAGGCCGAATTGTGGGGGCAAGGTGTGCCCCAAAGGGAGTGTCCATGGC<br>AGGTCCTGTTGTTGGTGAATGGAGCTCAGTTGTGTGGGGGGACCCTGATCAAC<br>ACCATCTGGGTGGTCTCCGCGGCCCACTGTTTCGACAAAATCAAGAACTGGAG<br>GAACCTGATCGCGGTCTGGGCGAGCACGACCTCAGCGAGCACGACGGGGAT<br>GAGCAGAGCCGGCGGGTGGCGCAGGTCATCATCCCCAGCACGTACGTCCCG<br>GGCACCACCAACCACGACATCGCGCTGCTCCGCCTGCACCAGCCCGTGGTCC<br>TCACTGACCATGTGGTGCCCCTCTGCCTGCCCGAACGGACGTTCTCTGAGAGG<br>ACGCTGGCCTTCGTGCGCTTCTCATTGGTCAGCGGCTGGGGCCAGCTGCTGG<br>ACCGTGGCGCCACGGCCCTGGAGCTCATGGTCCTCAACGTGCCCCGGCTGAT<br>GACCCAGGACTGCCTGCAGCAGTCACGGAAGGTGGGAGACTCCCCAAATATC<br>ACGGAGTACATGTTCTGTGCCGGCTACTCGGATGGCAGCAAGGACTCCTGCAA<br>GGGGGACAGTGGAGGCCCACATGCCACCCACTACCGGGGCACGTGGTACCTG | SEQ ID<br>NO: 18 FVII |

TABLE I-continued

```
ACGGGCATCGTCAGCTGGGGCCAGGGCTGCGCAACCGTGGGCCACTTTGGG
GTGTACACCAGGGTCTCCCAGTACATCGAGTGGCTGCAAAAGCTCATGCGCTC
AGAGCCACGCCCAGGAGTCCTCCTGCGAGCCCCATTTCCCTAG
```

```
ATGTTCCCAGGCTGCCCACGCCTCTGGGTCCTGGTGGTCTTGGGCACCAGCT          SEQ ID    FV
GGGTAGGCTGGGGGAGCCAAGGGACAGAAGCGGCACAGCTAAGGCAGTTCTA          NO: 19
CGTGGCTGCTCAGGGCATCAGTTGGAGCTACCGACCTGAGCCCACAAACTCAA
GTTTGAATCTTTCTGTAACTTCCTTTAAGAAAATTGTCTACAGAGAGTATGAACC
ATATTTTAAGAAAGAAAAACCACAATCTACCATTTCAGGACTTCTTGGGCCTACT
TTATATGCTGAAGTCGGAGACATCATAAAAGTTCACTTTAAAATAAGGCAGATA
AGCCCTTGAGCATCCATCCTCAAGGAATTAGGTACAGTAAATTATCAGAAGGTG
CTTCTTACCTTGACCACACATTCCCTGCGGAGAAGATGGACGACGCTGTGGCT
CCAGGCCGAGAATACACCTATGAATGGAGTATCAGTGAGGACAGTGGACCCAC
CCATGATGACCCTCCATGCCTCACACACATCTATTACTCCCATGAAAATCTGAT
CGAGGATTTCAACTCGGGGCTGATTGGGCCCCTGCTTATCTGTAAAAAGGGA
CCCTAACTGAGGGTGGGACACAGAAGACGTTTGACAAGCAAATCGTGCTACTA
TTTGCTGTGTTTGATGAAAGCAAGAGCTGGAGCCAGTCATCATCCCTAATGTAC
ACAGTCAATGGATATGTGAATGGGACAATGCCAGATATAACAGTTTGTGCCCAT
GACCACATCAGCTGGCATCTGCTGGGAATGAGCTCGGGGCCAGAATTATTCTC
CATTCATTTCAACGGCCAGGTCCTGGAGCAGAACCATCATAAGGTCTCAGCCA
TCACCCTTGTCAGTGCTACATCCACTACCGCAAATATGACTGTGGGCCCAGAG
GGGAAAGTGGATCATATCTTCTCTCACCCCAAAACATTTGCAAGCTGGGATGCAG
GCTTACATTGACATTAAAAACTGCCCAAAGAAAACCAGGAATCTTAAGAAAATAA
CTCGTGAGCAGAGGCGGCACATGAAGAGGTGGGAATACTTCATTGCTGCAGA
GGAAGTCATTTGGGACTATGCCACCTGTAATACCAGCGAATATGGACAAAAAATA
CAGGTCTCAGCATTTGGATAATTTCTCAAACCAAATTGGAAAACATTATAAGAAA
GTTATGTACACACAGTACGAAGATGAGTCCTTCACCAAACATACAGTGAATCCC
AATATGAAAGAAGATGGGATTTTGGGTCCTATTATCAGAGCCCAGGTCAGAGAC
ACACTCAAAATCGTGTTCAAAAATATGGCCAGCCGCCCCTATAGCATTTACCCT
CATGGAGTGACCTTCTCGCCTTATGAAGATGAAGTCAACTCTTCTTTCACCTCA
GGCAGGAACAACACCATGATCAGAGCAGTTCAACCAGGGGAAACCTATACTTA
TAAGTGGAACATCTTAGAGTTTGATGAACCCACAGAAATGATGCCCAGTGCTT
AACAAGACCATACTACAGTGACGTGGACATCATGAGAGACATCGCCTCTGGGC
TAATAGGACTACTTCTAATCTGTAAGAGCAGATCCCTGGACAGGCGAGGAATAC
AGAGGGCAGCAGACATCGAACAGCAGGCTGTGTTTGCTGTGTTTGATGAGAAC
AAAAGCTGGTACCTTGAGGACAACATCAACAAGTTTTGTGAAAATCCTGATGAG
GTGAAACGTGATGACCCCAAGTTTTATGAATCAAACATCATGAGCACTATCAAT
GGCTATGTGCCTGAGAGCATAACTACTCTTGGATTCTGCTTTGATGACACTGTC
CAGTGGCACTTCTGTAGTGTGGGGACCCAGAATGAAATTTTGACCATCCACTTC
ACTGGGCACTCATTCATCTATGGAAAGAGGCATGAGGACACCTTGACCCTCTT
CCCCATGCGTGGAGAATCTGTGACGGTCACAATGGATAATGTTGGAACTTGGA
TGTTAACTTCCATGAATTCTAGTCCAAGAAGCAAAAAGCTGAGGCTGAAATTCA
GGGATGTTAAATGTATCCCAGATGATGATGAAGACTCATATGAGATTTTTGAAC
CTCCAGAATCTACAGTCATGGCTACACGGAAAATGCATGATCGTTTAGAACCTG
AAGATGAAGAGAGTGATGCTGACTATGATTACCAGAACAGACTGGCTGCAGCA
TTAGGAATCAGGTCATTCCGAAACTCATCATTGAATCAGGAAGAAGAAGAGTTC
AATCTTACTGCCCTAGCTCTGGAGAATGGCACTGAATTCGTTTCTTCAAACACA
GATATAATTGTTGGTTCAAATTATTCTTCCCCAAGTAATATTAGTAAGTTCACTGT
CAATAACCTTGCAGAACCTCAGAAAGCCCCTTCTCACCAACAAGCCACCACAG
CTGGTTCCCACTGAGACACCTCATTGGCAAGAACTCAGTTCTCAATTCTTCCA
CAGCAGAGCATTCCAGCCCATATTCTGAAGACCCTATAGAGGATCCTCTACAG
CCAGATGTCACAGGGATACGTCTACTTTCACTTGGTGCTGGAGAATTCAAAAGT
CAAGAACATGCTAAGCATAAGGGACCCAAGGTAGAAAGAGATCAAGCAGCAAA
GCACAGGTTCTCCTGGATGAAATTACTAGCACATAAAGTTGGGAGCACCTAAG
CCAAGCACTGGTTCTCCTTCGGAATGAGGCCCTGGGAGGACCTTCCTAGCC
AAGCACTGGTTCTCCTTCCAGAATGAGGCCCTGGAAGGACCCTCCTAGTGAT
CTGTTACTCTTAAAACAAAGTAACTCATCTAAGATTTTGGTTGGGAGATGGCATT
TGGCTTCTGAGAAAGGTAGCTATGAAATAATCCAAGATACTGATGAAGACACAG
CTGTTAACAATTGGCTGATCAGCCCCCAGAATGCCTCACGTGCTTGGGGAGAA
AGCACCCCTCTTGCCAACAAGCCTGGAAAGCAGAGTGGCCACCCAAAGTTTCC
TAGAGTTAGACATAAATCTCTACAAGTAAGACAGGATGGAGGAAAGAGTAGACT
GAAGAAAAGCCAGTTTCTCATTAAGCACACGAAAAAAGAAAAAAGAGAAGCACAC
ACACCATGCTCCTTTATCTCCGAGGACCTTTCACCCTCTAAGAAGTGAAGCCTA
CAACACATTTTCAGAAAGAAGACTTAAGCATTCGTTGGTGCTTCATAAATCCAAT
GAAACATCTCTTCCCACAGACCTCAATCAGACATTGCCCTCTATGGATTTTGGC
TGGATAGCCTCACTTCCTGACCATAATCAGAATTCCTCAAATGACACTGGTCAG
GCAAGCTGTCCTCCAGGTCTTTATCAGACAGTGCCCCCAGAGGAACACTATCA
AACATTCCCCATTCAAGACCCTGATCAAATGCACTCTACTTCAGACCCCAGTCA
CAGATCCTCTTCTCCAGAGCTCAGTGAAATGCTTGAGTATGACCGAAGTCACAA
GTCCTTCCCCACAGATATAAGTCAAATGTCCCCTTCCTCAGAACATGAAGTCTG
GCAGACAGTCATCTCTCCAGACCTCAGCCAGGTGACCCTCTCTCCAGAACTCA
GCCAGACAAACCTCTCTCCAGACCTCAGCCACACGACTCTCTCTCCAGAACTC
ATTCAGAGAAACCTTTCCCCAGCCCTCGGTCAGATGCCCATTTCTCCAGACCTC
AGCCATACAACCCTTTCTCCAGACCTCAGCCATACAACCCTTTCTTTAGACCTC
AGCCAGACAAACCTCTCTCCAGAACTCAGTCAGACAAACCTTTCTCCAGCCCTC
GGTCAGATGCCCCTTTCTCCAGACCTCAGCCATACAACCCTTTCTCTAGACTTC
AGCCAGACAAACCTCTCTCCAGAACTCAGCCATATGACTCTCTCTCCAGAACTC
AGTCAGACAAACCTTTCCCCAGCCCTCGGTCAGATGCCCATTTCTCCAGACCT
CAGCCATACAACCCTTTCTCTAGACTTCAGCCAGACAAACCTCTCTCCAGAACT
CAGTCAAACAAACCTTTCCCCAGCCCTCGGTCAGATGCCCCTTTCTCCAGACC
```

TABLE I-continued

| | |
|---|---|
| CCAGCCATACAACCCTTTCTCTAGACCTCAGCCAGACAAACCTCTCTCCAGAAC<br>TCAGTCAGACAAACCTTTCCCCAGACCTCAGTGAGATGCCCCTCTTTGCAGATC<br>TCAGTCAAATTCCCCTTACCCCAGACCTCGACCAGATGACACTTTCTCCAGACC<br>TTGGTGAGACAGATCTTTCCCCAAACTTTGGTCAGATGTCCCTTTCCCCAGACC<br>TCAGCCAGGTGACTCTCTCTCCAGACATCAGTGACACCACCCTTCTCCCGGAT<br>CTCAGCCAGATATCACCTCCTCCAGACCTTGATCAGATATTCTACCCTTCTGAA<br>TCTAGTCAGTCATTGCTTCTTCAAGAATTTAATGAGTCTTTTCCTTATCCAGACC<br>TTGGTCAGATGCCATCTCCTTCATCTCCTACTCTCAATGATACTTTTCTATCAAA<br>GGAATTTAATCCACTGGTTATAGTGGGCCTCAGTAAAGATGGTACAGATTACAT<br>TGAGATCATTCCAAAGGAAGAGGTCCAGAGCAGTGAAGATGACTATGCTGAAA<br>TTGATTATGTGCCCTATGATGACCCCTACAAAACTGATGTTAGGACAAACATCA<br>ACTCCTCCAGAGATCCTGACAACATTGCAGCATGGTACCTCCGCAGCAACAAT<br>GGAAACAGAAGAAATTATTACATTGCTGCTGAAGAAATATCCTGGGATTATTCA<br>GAATTTGTACAAAGGGAAACAGATATTGAAGACTCTGATGATATTCCAGAAGAT<br>ACCACATATAAGAAAGTAGTTTTTCGAAAGTACCTCGACAGCACTTTTACCAAC<br>GTGATCCTCGAGGGGAGTATGAAGAGCATCTCGGAATTCTTGGTCCTATTATCA<br>GAGCTGAAGTGGATGATGTTATCCAAGTTCGTTTTAAAAATTTAGCATCCAGAC<br>CGTATTCTCTACATGCCCATGGACTTTCCTATGAAAAATCATCAGAGGGAAAGA<br>CTTATGAAGATGACTCTCCTGAATGGTTTAAGGAAGATAATGCTGTTCAGCCAA<br>ATAGCAGTTATACCTACGTATGGCATGCCACTGAGCGATCAGGGCCAGAAAGT<br>CCTGGCTCTGCCTGTCGGGCTTGGGCCTACTACTCAGCTGTGAACCCAGAAAA<br>AGATATTCACTCAGGCTTGATAGGTCCCCTCCTAATCTGCCAAAAAGGAATACT<br>ACATAAGGACAGCAACATGCCTATGGACATGAGAGAATTTGTCTTACTATTTAT<br>GACCTTTGATGAAAAGAAGAGCTGGTACTATGAAAAGAAGTCCCGAAGTTCTTG<br>GAGACTCACATCCTCAGAAATGAAAAAATCCCATGAGTTTCACGCCATTAATGG<br>GATGATCTACAGCTTGCCTGGCCTGAAAATGTATGAGCAAGAGTGGGTGAGGT<br>TACACCTGCTGAACATAGGCGGCTCCCAAGACATTCACGTGGTTCACTTTCAC<br>GGCCAGACCTTGCTGGAAAATGGCAATAAACAGCACCAGTTAGGGGTCTGGCC<br>CCTTCTGCCTGGTTCATTTAAAACTCTTGAAATGAAGGCATCAAAACCTGGCTG<br>GTGGCTCCTAAACACAGAGGTTGGAGAAAACCAGAGAGCAGGGATGCAAACG<br>CCATTTCTTATCATGGACAGAGACTGTAGGATGCCAATGGGACTAAGCACTGGT<br>ATCATATCTGATTCACAGATCAAGGCTTCAGAGTTTCTGGGTTACTGGGAGCCC<br>AGATTAGCAAGATTAAACAATGGTGGATCTTATAATGCTTGGAGTGTAGAAAAA<br>CTTGCAGCAGAATTTGCCTCTAAACCTTGGATCCAGGTGGACATGCAAAGGA<br>AGTCATAATCACAGGGATCCAGACCCAAGGTGCCAAACACTACCTGAAGTCCT<br>GCTATACCACAGAGTTCTATGTAGCTTACAGTTCCAACCAGATCAACTGGCAGA<br>TCTTCAAAGGGAACAGCACAAGGAATGTGATGTATTTTAATGGCAATTCAGATG<br>CCTCTACAATAAAAGAGAATCAGTTTGACCCACCTATTGTGGCTAGATATATTAG<br>GATCTCTCCAACTCGAGCCTATAACAGACCTACCCTTCGATTGGAACTGCAAGG<br>TTGTGAGGTAAATGGATGTTCCACACCCCTGGGTATGGAAAATGAAAGATAG<br>AAAACAAGCAAATCACAGCTTCTTCGTTTAAGAAATCTTGGTGGGAGATTACT<br>GGGAACCCTTCCGTGCCCGTCTGAATGCCCAGGGACGTGTGAATGCCTGGCA<br>AGCCAAGGCAAACAATAAGCAGTGGCTAGAAATTGATCTACTCAAGATCAA<br>GAAGATAACGGCAATTATAACACAGGGCTGCAAGTCTCTGTCCTCTGAAATGTA<br>TGTAAAGAGCTATACCATCCACTACAGTGAGCAGGGAGTGGAATGGAAACCAT<br>ACAGGCTGAAATCCTCCATGGTGGACAAGATTTTTGAAGGAAATACTAATACCA<br>AAGGACATGTGAAGAACTTTTTCAACCCCCCAATCATTTCCAGGTTTATCCGTG<br>TCATTCCTAAAACATGGAATCAAAGTATTGCACTTCGCCTGGAACTCTTTGGCT<br>GTGATATTTACTAG | |
| ATGCAGCGCGTGAACATGATCATGGCAGAATCACCAGGCCTCATCACCATCTG<br>CCTTTTAGGATATCTACTCAGTGCTGAATGTACAGTTTTCTTGATCATGAAAAC<br>GCCAACAAAATTCTGAATCGGCCAAAGAGGTATAATTCAGGTAAATTGGAAGAG<br>TTTGTTCAAGGGAACCTTGAGAGAGAATGTATGGAAGAAAGTGTAGTTTTGAA<br>GAAGCACGAGAAGTTTTTGAAAACACTGAAAGAACAACTGAATTTTGGAAGCAG<br>TATGTTGATGTAACATGTAACATTAAGAATGGCAGATGCGAGCAGTTTTGTAAA<br>AATAGTGCTGATAACAAGGTGGTTTGCTCCTGTACTGAGGGATATCGACTTGCA<br>GAAAACCAGAAGTCCTGTGAACCAGCAGTGCCATTTCCATGTGGAAGAGTTTCT<br>GTTTCACAAACTTCTAAGCTCACCCGTGCTGAGACTGTTTTTCCTGATGTGGAC<br>TATGTAAATTCTACTGAAGCTGAAACCATTTTGGATAACATCACTCAAAGCACCC<br>AATCATTTAATGACTTCACTCGGGTTGTTGGTGGAGAAGATGCCAAACCAGGTC<br>AATTCCCTTGGCAGGTTGTTTTGAATGGTAAAGTTGATGCATTCTGTGGAGGCT<br>CTATCGTTAATGAAAAATGGATTGTAACTGCTGCCCACTGTGTTGAAACTGGTG<br>TTAAAATTACAGTTGTCGCAGGTGAACATAATATTGAGGAGACAGAACATACAG<br>AGCAAAAGCGAAATGTGATTCGAATTATTCCTCACCACAACTACAATGCAGCTA<br>TTAATAAGTACAACCATGACATTGCCCTTCTGGAACTGGACGAACCCTTAGTGC<br>TAAACAGCTACGTTACACCTATTTGCATTGCTGACAAGGAATACACGAACATCT<br>TCCTCAAATTTGGATCTGGCTATGTAAGTGGCTGGGGAAGAGTCTTCCACAAAG<br>GGAGATCAGCTTTAGTTCTTCAGTACCTTAGAGTTCCACGAGTTGACCGAGCCA<br>CATGTCTTCGATCTACAAAGTTCACCATCTATAACAACATGTTCTGTGCTGGCTT<br>CCATGAAGGAGGTAGAGATTCATGTCAAGGAGATAGTGGGGGACCCCATGTTA<br>CTGAAGTGGAAGGGACCAGTTCTTAACTGGAATTATTAGCTGGGGTGAAGAG<br>TGTGCAATGAAAGGCAAATATGGAATATATACCAAGGTATCCCGGTATGTCAAC<br>TGGATTAAGGAAAAAACAAAGCTCACTTAA | SEQ ID<br>NO: 20 FIX-Padua |

SEQ ID NO: 1 (LV.pF8.1) corresponds to the polynucleotide sequence from about 0 to about −1175 of FVIII gene (CDS) or a functional fragment thereof, in other words the nucleotide region from about 0 to −1175 of the FVIII gene promoter upstream FVIII gene (CDS) (FIG. 2A). FIG. 2 shows the sequences of the invention upstream GFP as an example of marker gene, indeed also luciferase gene has been used as marker by the Applicant (see example). The marker gene is used in order to evaluate efficiency of transgene expression and to easily identify transgene-expressing cells after gene transfer and in particular, to study promoter specific activity and evaluate GFP expression at FACS or after immunostaining. F8 promoter activity and transcription factor interaction was instead analyzed by Luciferase assay. However, the sequences of the invention are mainly used as such without any marker gene.

SEQ ID NO: 2 (LV.pF8.2) corresponds to the polynucleotide sequence from about 0 to about −599 of FVIII gene (CDS) or a functional fragment thereof, in other words the nucleotide region from about 0 to −599 of the FVIII gene promoter upstream FVIII gene (CDS) (FIG. 2B).

SEQ ID NO: 3 (LV.pF8.3) comprises the polynucleotide sequences from about 0 to about −1175 and from about −3625 to about −4184 of FVIII gene (CDS) or a functional fragment thereof, in other words the nucleotide region from about 0 to −1175 and that from about −3625 to about −4184 of the FVIII promoter upstream FVIII gene (CDS) (FIG. 2C). In this regard, the applicant demonstrated for the first time that the sequence from about −3625 to about −4184 of FVIII gene enhances FVIII gene expression, preferably in endothelial and/or hematopoietic cells. This sequence is therefore an enhancer sequence located in the FVIII gene promoter.

SEQ ID NO: 4 (LV.pF8.4) corresponds to the polynucleotide sequence starting from 0 to −599 of FVIII promoter and from about −3625 to about −4184 of FVIII gene (CDS) or a functional fragment thereof, in other words the nucleotide region from about 0 to −599 and that from about −3625 to about −4184 of the FVIII promoter upstream FVIII gene (CDS) (FIG. 2D).

SEQ ID NO: 5 (LV.pF8.5) comprises the polynucleotide sequence starting from 0 to −1175 of FVIII promoter and from about −3625 to about −4429 of FVIII gene (CDS) or a functional fragment thereof, in other words the nucleotide region from about 0 to −1175 and that from about −3625 to about −4429 of the FVIII promoter upstream FVIII gene (CDS) (FIG. 2E). In this regard, the applicant demonstrated for the first time that the sequence from about −3625 to about −4429 of FVIII gene enhances FVIII gene expression, preferably in endothelial and/or hematopoietic cells. This sequence is therefore an enhancer sequence located in the FVIII gene promoter, in particular the longer form of the previously disclosed enhancer sequence.

SEQ ID NO: 6 (LV.pF8.6) corresponds to the polynucleotide sequence starting from 0 to −599 of FVIII promoter and from about −3625 to about −4429 of FVIII gene (CDS) or a functional fragment thereof, in other words the nucleotide region from about 0 to −599 and that from about −3625 to about −4429 of the FVIII promoter upstream FVIII gene (CDS) (FIG. 2F).

SEQ ID NO: 7 (LV.pF8.7) corresponds to the polynucleotide sequence from about 0 to about −2350 of FVIII gene (CDS) or a functional fragment thereof, in other words the nucleotide region from about 0 to −2350 of the FVIII gene promoter upstream FVIII gene (CDS) (FIG. 2G).

SEQ ID NO: 10 comprises SEQ ID NO: 1, 2, 8, 9 and the region included between the promoters and enhancer regions. In other words, this sequence corresponds to the polynucleotide sequence from about 0 to −4429 upstream FVIII gene sequence (CDS) (FIG. 1).

SEQ ID NO: 12 corresponds to the polynucleotide sequence from about 0 to −442 upstream FVIII gene sequence (CDS) (FIG. 2H).

SEQ ID NO: 13 corresponds to a BDD-FVIII variant containing the human N6 B domain.

SEQ ID NO: 14 corresponds to a BDD-FVIII variant with an amino acid change matches to the R1645H of the canine FVIII B domain putative furin cleavage site.

SEQ ID NO: 15 corresponds to a BDD-FVIII variant codon optimized by the same amino acid structure of BDD-FVIII.

SEQ ID NO: 16 corresponds to a BDD-FVIII variant codon optimized by the same amino acid structure of BDD-FVIII with the addiction of the amino acid change at the furin cleavage site within the B domain (position R1645H)

SEQ ID NO: 17 corresponds to the CDS of FIX coagulation gene SEQ ID NO: 18 corresponds to the CDS of coagulation FVII gene SEQ ID NO: 19 corresponds to the CDS of coagulation FV gene.

SEQ ID NO: 20 corresponds to the CDS of FIX gene s with a gain-of-function mutation (R338L) in the factor IX gene The cell expression of the therapeutic gene, preferably FVIII and/or its variants, obtained by using these sequences (as promoter of the therapeutic gene of interest) allows rescuing/curing a disease such as hemophilia, preferably type A hemophilia, and/or any condition or disease related to or associate with a deficit or any misexpression of the therapeutic gene, preferably FVIII and/or its variants.

Therefore, a second aspect of the present invention refers to the disclosed polynucleotide sequences for use in gene therapy and/or cellular therapy, in particular for treating, preferably by gene and/or cellular therapy approach, hemophilia, preferably type A hemophilia or any condition or disease related to or associate with a deficit in the expression of the therapeutic gene, preferably FVIII and/or its variants.

Besides hemophilia A the disclosed sequences could be used also to promote the endothelial and/or hematopoietic specific expression of further genes involved in the coagulation cascade, preferably these genes are selected from FIX, FVII, FV and any combination thereof.

According to a preferred embodiment of the invention, FIX is preferably SEQ ID NO: 17 e/o 20; FVII is preferably SEQ ID NO: 18; FV is preferably SEQ ID NO: 19.

Therefore, the disclosed sequences can be also used for treating a condition/disease related to or associated with the misexpression of any further gene involved in the coagulation cascade, preferably FIX, FVII or FV as disclosed above.

According to a further aspect of the invention, the disclosed sequences are useful to promote the endothelial and/or hematopoietic specific expression of growth factors, or functional protein or reporter protein.

As already said the disclosed sequences are used as promoter nucleotide sequences useful to target/address/induce the expression of a therapeutic gene, for e.g. FVIII gene, specifically into endothelial cells and/or hematopoietic cells. The endothelial cells are preferably, the endothelial cells of the liver, more preferably, the liver sinusoidal endothelial cells or further vascular and/or lymphatic endothelial cells. The hematopoietic cells are preferably monocytes/macrophages, preferably the monocytes/macrophages of the spleen.

According to a preferred embodiment of the invention, the disclosed sequences are contained in a vector, preferably any vector useful for gene expression.

The vector is preferably a viral vector, more preferably a lentiviral (LV) or a retroviral vector, preferably selected from the HIV-1 and/or gamma retroviruses. Preferably said vector is the improved self-inactivating (SIN) HIV-1 based lentiviral vector (LV, pCCL-prom-transgene-cPPT-Wpre) with the third generation lentiviral packaging system to produce LV.

Alternatively, the vector is selected from adeno-associated viral vector (AAV), preferably serotypes that can be used in endothelial and hematopoietic cells.

According to a further preferred embodiment, the vector contains sequences for modulating gene expression, preferably selected from: a poly-adenilation sequence; a Woodchuck hepatitis post-transcriptional regulatory element (WPRE—to increase the transcript stability); the central polypurine tract (cPPT), preferably for lentiviral vectors; mirTs (mir Target sequences—that are sequences recognized by tissue-specific miRNAs inducing cell specific gene knockdown in selected cell types) and any combination tehreof. Preferably, said mirTs is selected from: mirT-142-3p (to detarget transgene expression from all hematopoietic cells); mirT-223 (to detarget transgene expression from all myeloid cells); mirT-126 (to detarget transgene expression from hematopoietic progenitor cells, plasmacytoid dendritic cells and endothelial cells) and any combination tehreof.

More preferably, the vector comprises an enhancer polynucleotide sequence. The enhancer polynucleotide sequence preferably comprises SEQ ID NO: 8 and/or 9. In particular SEQ ID NO: 8 is a short enhancer sequence corresponding to the polynucleotide sequence from about −3625 to about −4184 of the FVIII gene sequence, while SEQ ID NO: 9 is the longer form of the enhancer corresponding to the polynucleotide sequence from about −3625 to about −4429 of the FVIII gene sequence.

More preferably, said enhancer polynucleotide sequence can be positioned upstream or downstream and/or close or far from the gene sequence the expression of which has to be enhanced. For e.g. SEQ ID NO: 3-7 have these enhancer sequences upstream to the gene to be regulated.

Therefore, a further aspect of the present invention is a vector, preferably an expression vector, comprising at least one sequence selected from SEQ ID NO: 1-10, 12 and any combination of these sequences, preferably as disclosed above. The obtained vectors are useful for targeting specifically the expression of a therapeutic gene of interest in endothelial and/or hematopoietic. Preferably, the therapeutic gene of interest is FVIII, preferably SEQ ID NO: 11 and/or 15 and/or variants thereof, and/or further gene of the coagulation cascade, preferably selected from: FIX, FVII and FV, or growth factors, cytokines and small molecules, wherein FIX is preferably SEQ ID NO: 17 e/o 20; FVII is preferably SEQ ID NO: 18; FV is preferably SEQ ID NO: 19.

A further aspect of the present invention refers to host cells comprising the nucleotide sequences and/or the vectors disclosed above.

A further aspect of the present invention refers to transgenic animals comprising the host cells, or the vectors or the nucleotide sequences disclosed above.

The host cells, or the vectors or the nucleotide sequences disclosed above can be used in the manufacture of a medicament that is preferably used in therapy, more preferably in gene and/or cell therapy, more preferably for cure/treat hemophilia, preferably type A hemophilia.

A further aspect of the present invention refers to a pharmaceutical composition comprising the host cells, or the vectors or the nucleotide sequences disclosed above and at least one pharmaceutically acceptable excipient.

A further aspect of the present invention refers to a method for treating a disease that is preferably hemophilia, more preferably type A hemophilia, comprising at least one step of administering a therapeutically effective amount of the host cells, or the vectors or the nucleotide sequences disclosed above to a patient suffering from such disease, preferably hemophilia. According to a preferred embodiment the patient has an immune-response to FVIII, in other words he shows systemic detection of anti-FVIII antibodies.

A further aspect of the present invention refers to the use of the SEQ ID NO: 1-10 and 12, preferably SEQ ID NO: 3-7 and 12 for modulating the expression, preferably into endothelial and/or hematopoietic cells of a therapeutic gene, preferably FVIII, more preferably SEQ ID NO: 11 e/o 15 and/or variants thereof and/or further coagulation cascade genes, preferably FIX, FVII and FV, and/or growth factors, wherein FIX is preferably SEQ ID NO: 17 e/o 20; FVII is preferably SEQ ID NO: 18; FV is preferably SEQ ID NO: 19.

EXAMPLE pF8 Cloning in Lentivirus Transfer Constructs pFVIII (F8) variants were amplified by PCR from human genomic DNA by inserting at 5' and 3' ends the restriction sites for the enzymes XhoI and AgeI. These sites were used to insert pF8 variants in place of ubiquitous PGK promoter in LV.PGK.GFP in order to obtain the pF8.GFP.

To generate LV.pF8.FVIII we inserted the BDD-FVIII in place of GFP in the LV.pF8.GFP. For cloning SaiI and AgeI endonucleases were used to excide both GFP and FVIII from LV.pF8.GFP and LV.PGK.FVII, respectively. Ligase product identity was assessed by restriction analysis and sequencing.

Primers used for cloning and sequencing are reported in Table II.

TABLE II

| Primer use | primer name | Primer sequence | |
|---|---|---|---|
| LV.pF8.1 cloning | pF8_short_XhoI_FOR | CAGCCTCGAGGAGCTCAC | SEQ ID NO: 21 |
|  |  | CATGGCTACATTCTGA | SEQ ID NO: 22 |
|  | pF8_AgeI_REV | CGCACCGGTGACTTATTG | SEQ ID NO: 23 |
|  |  | CTACAAATGTTCAAC | SEQ ID NO: 24 |
| LV.pF8.2 cloning | PF8_ECL_XhoI_FOR | CAGCCTCGAGGTTTTTAA | SEQ ID NO: 25 |
|  |  | AACAATAGTTGCCTAACC | SEQ ID NO: 26 |
|  | pF8_AgeI_REV | CGCACCGGTGACTTATTG | SEQ ID NO: 27 |
|  |  | CTACAAATGTTCAAC | SEQ ID NO: 28 |

TABLE II-continued

| Primer use | primer name | Primer sequence | |
|---|---|---|---|
| LV.pF8.3 cloning/ sequencing | pF8_enhancer_Short_MfeI_FOR | CTTCAATTGGGGGCTCGC TCGCTCAGTAC | SEQ ID NO: 29 |
| | pF8_enhancer_MfeI_REV | CTTCAATTGCTCAACTCC TATGGTGCCAC | SEQ ID NO: 30 |
| LV.pF8.5 cloning/ sequencing | pF8_enhancer_long_MfeI_FOR | CTTCAATTGTCGCCACCA CTTGGCTTCCG | |
| | pF8_enhancer_MfeI_REV | CTTCAATTGCTCAACTCC TATGGTGCCAC | |
| LV.pF8.7 cloning | pF8_Long_XhoI_FOR | CAGCCTCGAGCAGCAGTT CCCACAAACGTTACC | |
| | pF8_AgeI_REV | CGCACCGGTACTTATTGC TACAAATGTTCAAC | |
| Constructs sequencing | Deny_RF2_FOR | GACCCACCTCCCAACCCC G | |
| | GFP_REV | CGTCGCCGTCCAGCTCGA CCAG | |

Construct Generation and Cloning

For FVIII promoter constructs generation consider FIG. 1 that shows the graphic representation of the regions of interest within the 4429 bp of F8 promoter.

Once selected the region of interest, we generated several LV carrying the Green Fluorescence Protein—GFP—under the control of the FVIII promoter sequence combinations. The combinations are explained below and graphically summarized in FIG. 2.

1) LV.pF8.1 (SEQ ID NO: 1—FIG. 2A)—a and b sequences (from 0 to −1175) were amplified from human genomic DNA by PCR using a forward primer containing at the 5' the XhoI restriction site and the reverse primer containing the restriction site sequence for AgeI. These 2 enzymes were used to clone a,b sequences in place of the phosphoglycerate kinase promoter (PGK) in a LV containing the GFP as transgene. The resulting construct was analyzed by diagnostic enzymatic digestion and sequencing.

2) LV.pF8.2 (SEQ ID NO: 2—FIG. 2B)—a sequence (from 0 to −599) was amplified from LV.pF8.1.GFP by PCR using a forward primer containing at the 5' the XhoI restriction site and the reverse primer containing the restriction site sequence for AgeI. These 2 enzymes were used to clone the a sequence in place of the phosphoglycerate kinase promoter (PGK) in a LV containing GFP as transgene. The resulting construct was analyzed by diagnostic enzymatic digestion and sequencing.

3) LV.pF8.3 (SEQ ID NO 3:—FIG. 2C)—e sequence (from −3625 to −4184) was amplified from genome DNA by PCR using both primers containing at the 5' the MfeI restriction site. The PCR product was digested with this enzyme and inserted in the LV.pF8.1.GFP in the MfeI restriction site that is located in the backbone of the LV transfer construct. By this strategy e sequence was inserted 979 bp upstream to the starting of the internal promoter. The resulting construct was analyzed by restriction enzyme analysis and sequencing.

4) LV.pF8.4 (SEQ ID NO: 4—FIG. 2D)—a fragment (from 0 to −599) was isolated from the LV.pF8.2.GFP construct by digestion with XhoI and AgeI and used as insert. The a-b promoter sequence (from 0 to −1175) was removed from the LV.pF8.3.GFP construct using the same enzymes and the resulting construct was ligated with a fragment. The final construct obtained was analyzed by restriction enzyme analysis and sequencing.

The sequences e (enhancer) from the construct 3 and 4 were not cloned in contiguity of the promoter but in a region of LV transfer construct upstream to the promoter in the delta env sequence of HIV present in the LV transfer construct. This because the distance of this region from the ATG start codon is mimicking the distance of the FVIII putative enhancer from its promoter in the original sequence, moreover for this sequence to function as an enhancer a DNA spacer is required.

5) LV.pF8.5 (SEQ ID NO: 5—FIG. 2E)—f sequence (from −3625 to −4429) was amplified from genome DNA by PCR using both primers containing at the 5' the MfeI restriction site. The PCR product was digested with this enzyme and inserted in the LV.pF8.1.GFP in the MfeI restriction site that is located in the backbone of the LV transfer construct. By this strategy f sequence was inserted 979 bp upstream to the starting of the internal promoter. The resulting construct was analyzed by restriction enzyme analysis and sequencing.

6) LV.pF8.6 (SEQ ID NO 2F)—a fragment (from 0 to −599) was isolated from the LV.pF8.2.GFP construct by digestion with XhoI and AgeI and used as insert. The a-b promoter sequence (from 0 to −1175) was removed from the LV.pF8.5.GFP construct using the same enzymes and the resulting construct was ligated with a fragment. The final construct obtained was analyzed by restriction enzyme analysis and sequencing.

The sequences f (enhancer) from the construct 5 and 6 were not cloned in contiguity of the promoter but in a region of LV transfer construct upstream to the promoter in the delta env sequence of HIV present in the LV transfer construct. This because the distance of this region from the ATG start codon is mimicking the distance of the FVIII putative enhancer from its promoter in the original sequence, moreover for this sequence to function as an enhancer a DNA spacer is required.

LV.pF8.7 (SEQ ID NO 2G)—a, b and c sequences (from 0 to −2350) were amplified from human genomic DNA by PCR using a forward primer containing at the 5' the XhoI restriction site and the reverse primer containing the restriction site sequence for AgeI. These 2 enzymes were used to clone a,b and c sequences in place of the phosphoglycerate kinase promoter (PGK) in a LV containing the GFP as transgene. The resulting construct was analyzed by diagnostic enzymatic digestion and sequencing.

LV.pF8.8 (SEQ ID NO 12)—a0 sequence (from 0 to −442) was obtained by removing portion b and part of the portion a from LV.pF8.1 construct through XhoI and XbaI enzymatic digestion. The resulting construct was analyzed by diagnostic enzymatic digestion and sequenced.

Lentiviral Vectors Production

Third-generation lentiviral vectors were produced using the protocol disclosed in Follenzi and Naldini, 2002; Methods and Enzymology. 293T cells were cotransfected with four plasmids by calcium phosphate precipitation. These vectors were: 1) the pMDLg/RRE packaging plasmid; 2) the pMD2.VSV-G envelope-coding plasmid; 3) pRSV-Rev plasmid and 4) transfer vector plasmid LV.PGK.GFP, LV.pF8.GFP, LV.pF8.FVIII and all the described constructs.

All four plasmids were added to cells in a 15-cm dish and forty hours following transfection the culture supernatant, containing the packaged viral particles, was collected and concentrated by ultracentrifugation.

Collected viral particles were titrated on hECV (human endothelial cell line) or 293T cells using limiting dilution analysis.

For the lentiviral vector expressing GFP each dilution was quantified by FACS as percentage of GFP$^+$ cells. Calculation from the titration analysis indicated about 1-2×10$^9$ transducing viral particles per milliliter. Instead, for lentiviral vector not expressing GFP, genomic DNA was isolated from 293T and titer was calculated by qPCR for integrated LV copy calculation.

Genomic DNA Isolation and LV Titration by qPCR

Genomic DNA was isolated from transduced 293T cells with ReliaPrep™gDNA Tissue MiniPrep System (Promega). The quantitative real time PCR was carried out in a 20-μl total volume containing 1× SYBR green PCR master mix (PROMEGA), 1 μM forward and reverse primers (wpre-Δnef) and 1 μM forward and reverse primers (hGAPDH), 50 ng of genomic DNA.

Quantitative PCR were performed by incubation at 95° C. for 3 minutes and 40 amplification cycles of 95° C. for 3 minutes and then 60° C. for 30 seconds. Primers used are reported in Table III

TABLE III

| Primers | primer name | Primer sequence |
|---|---|---|
| q-PCR | Wpre_FOR | tggattctgcgcgggacgtc |
|  | ΔNEF_REV | ggctaagatctacagctgccttg |
|  | hGapdh_FOR | atcgaaggtggaagagtggga |
|  | hGapdh_REV | agtgggtgtcgctgttgaagt |

Animals

Animal studies were performed according to an approved protocol by the Animal Care and Use Committees of UPO, Novara, Italy.

In vivo experiments were performed on 8-10 weeks old mice. For GFP expression studies, lentiviral vectors were delivered in C57Bl/6 WT mice. C57Bl/6 and 129/Bl16 Hemophilia A mice were used for in vivo and ex vivo gene therapy studies using LV. pF8.FVIII. Immunocompromised NOD/SCID-γNull HA mice (NSG-HA) were generated in our laboratory by crossing NOD/SCID HA mice with NOD.Cg-PrkdcscidIl2rgtm1WjI/SzJ (γNull) purchased by Jackson lab. For HSC transplantation studies busulfan myeloablation was performed on recipient mice. The busulfan solution for injection was prepared as follow: 25 mg of drug were solved in 1 ml of acetone and then diluted in 9 ml of peanut oil. Immunocompetent HA mice were lethally conditioned by intraperitonal injection of 25 mg/kg of busulfan from days −4 to −1 before transplantation while NSG-HA mice received a sublethal conditioning by only one injection of 50 mg/kg of busulfan the day before transplantation. NSG-HA mice were kept in autoclaved microisolator cages and fed with sterile food and water at the animal facilities of UPO. Moreover, all animals procedures made on NSG-HA mice were performed under sterile hood.

Mouse and Human Hematopoietic Stem Cells Isolation and Transplantation.

To isolate murine HSC (lineage negative cells, Lin−) bone marrow (BM) was flushed from femurs, tibiae and humeri of 6-8 weeks old donor mice. After red blood lysis, Lin$^-$ cells were obtained by immunomagnetic negative selection from total BM cells using Lineage Cell Depletion Kit (MiltenyiBiotec). After isolation cells were transduced with LVs at MOI 100 and cultured at density of 1×10$^6$/ml in serum free STEM-SPAM medium without cytokines. Human HSC were isolated from cord blood after immunomagnetic negative selection to obtain progenitors CD34$^+$ cells and cultured at density of 1×10$^6$/ml in serum free STEM-SPAM medium (Lonza) added with 50 ng/ml hTPO, 50 ng/ml hSCF, 50 ng/ml hIL-3 and 50 ng/ml hFlt3-L. On the basis of experiment CD34$^+$ cells were transduced with LV at Multiplicity of infection (MOI) of 30. For transplantation, 24 h after isolation a total of 3×10$^5$ or 6×10$^5$ CD34$^+$ or 10$^6$ lin$^-$ cells were resuspended in serum free STEM-SPAM without cytokines and tail vein injected in 400 μl of volume in busulfan-conditioned mice.

Analysis of Blood and Organs of Treated Mice.

The engraftment of transplanted mice was evaluated at several time points in the peripheral blood as percentage of GFP+ or human CD45+ cells. For each time point blood was collected by retro-orbital puncture using a glass capillar. Erythrocytes were eliminated by incubating RBLB for 10 min at 4° C.

Total white cells were directly analyzed by Flow cytometry analysis (FACS) for GFP or incubated with anti-human CD45 PE conjugated antibody to assess the engraftment after xenotransplantation. Total spleen cells were obtained by digestion for 30' at 37° C. in HBSS (Sigma Aldrich) containing 10% FBS and 0.2 mg/ml collagenase IV and then filtered through a 70-μm cell strainer (Falcon). BM cells were obtained by flushing tibiae and femurs. For both spleen and BM red blood cells were lysed for 8' with RBLB.

Thymuses were mechanically disrupted through a 70-μm cell strainer. For the liver, hepatocytes and liver non parenchymal cells (NPC) were separated after liver perfusion as previously described. Briefly, liver was perfused via portal vein with buffer at 37° C. containing 1.9 mg/ml EGTA, for 2' with buffer lacking EGTA, and for 7-9' with buffer containing 0.03% (w/v) collagenase and 5 mM CaCl$_2$.2H$_2$O.

The liver was dissociated in perfusion buffer, and cells were passed through 80-μm filter pores and centrifuged twice at 50 g for 5' to isolate hepatocytes. NPCs in the supernatant were washed and pelleted under 350 g for 10'.

Flow Cytometric Analysis

For cell staining cells were resuspended in staining buffer (PBS, FBS 1% and NaN$_3$ 0.1%) and incubate for 10' with anti-mouse CD16/CD32 as blocking and finally incubated for 30' on ice. The antibodies used are listed in Table IV. For the acquisition a FACS Calibur (Becton Dickinson Immunocytometry System) has been used and data obtained were analyzed by Flowing software 2.5 (Cell Imaging Core, Turku Centre for Biotechnology, Finland).

TABLE IV

| Antibody | Reactivity | Manufacturer | Format |
|---|---|---|---|
| CD16/32 | mouse | BD Pharmingen | Purified |
| CD45 | human | Miltenyi Biotec | PE |
| CD11b | human/mouse | Miltenyi Biotec | PE |

TABLE IV-continued

| Antibody | Reactivity | Manufacturer | Format |
|---|---|---|---|
| Tie-2 | human | Miltenyi Biotec | PE |
| CD31 | human | Immunotools | APC |
| CD14 | mouse | Biolegend | APC |
| Sca1 | mouse | e-Bioscience | PE |
| Gr-1 | mouse | Immunotools | APC |
| B220 | mouse | eBioscience | PE |
| CD11c | mouse | eBioscience | PE |
| CD4 | mouse | Immunotools | PE |
| CD8a | mouse | Immunotools | APC |
| CD19 | mouse | Miltenyi Biotec | PE |
| CD3 | mouse | Miltenyi Biotec | PE |
| F4/80 | mouse | Invitrogen | PE |
| Tie-2 | mouse | eBioscience | PE |
| CD31 | mouse | eBioscience | APC |
| CD146 | mouse | Miltenyi Biotec | PE |

Immunofluorescence

For mouse organs staining, liver and spleen of injected mice were recovered and fixed for 2 h in paraformaldeide-hyde (PAF) 4%, equilibrated in sucrose 30% in PBS for 48 h and finally embedded in optimal cutting temperature medium (OCT). 5-6 µm thick cryostat sections were post-fixed in PAF 4% and saturated in 5% goat serum, 1% BSA, 0.1% Triton X-100 in PBS for 1 h at room temperature (RT). Primary antibodies were diluted in PBS containing 2% goat serum, 1% BSA, 0.1% Triton X-100, and incubated for 1 h at RT.

After washing, sections were incubated with the secondary antibodies (in PBS containing 1% BSA, 0.1% Triton X-100) for 45' at RT and finally samples were mounted with Mowiol (Sigma Aldrich). For nuclei detection DAPI was added to the secondary antibodies solution.

FVIII Activity Assays

FVIII activity was measured on treated mice plasma by activated partial thromboplastin time (aPTT) assay, chromogenic assay using Coatest® SP4 FVIII kit (CHROMOGENIX) and tail clip assay at different time points. To obtain the plasma from mice, peripheral blood was collected in 3.2% citrate and centrifuged at 3000 rpm for 10'. Standard curves were generated by serial dilution of a commercial hFVIII (KOGENATE®, Bayer) for chromogenic assay and by serial dilution of human plasma in pooled hemophilic mouse plasma for aPTT assay. Results were expressed in IU and percentage of correction for chromogenic and aPTT, respectively. Tail clip assay was performed on anesthetized mice by cutting the distal portion of the tail at a diameter of 3-4 mm; the tails were then placed in a conical tube containing 14 ml of saline at 37° C. and blood was collected for 2'. Tubes were centrifuged to collect erythrocytes, resuspended in red blood lysis buffer (155 mM $NH_4Cl$, 10 mM $KHCO_3$, and 0.1 mM EDTA), and the absorbance of the sample was measured at wavelength 575 nm. Results were analyzed by comparing the amount of blood loss obtained from treated HA mice with WT and untreated HA mice serving as controls.

Anti-FVIII Antibodies Detection

Direct ELISA was performed on plasma of treated mice to evaluated the presence of anti FVIII antibodies. 96 wells plates were coated over night at 4° C. with 5 µg/ml of commercial recombinant BDD-FVIII (Refacto, Pfizer), after that wells were washed and saturated with BSA (TBS-BSA 0.2%) for 3 hours at 37° C. Plasma of injected mice was serially diluted from 1/200 to 1/2000 and incubated as primary antibody for 2 hours at 37° C. After washing, the secondary antibody (sheep anti-mouse horseradish peroxidase conjugated antibody) was incubated for 1 hour at 37° C. Reaction was developed with TMB (tetramethilbenzidine) prepared according to the manufacturer's protocol and stopped with $H_2SO_4$ 0.5 N. Absorbance were finally analyzed by spectophotometer at 450 nm wavelength. Results were normalized using a pooled plasma of non-injected HA mice and were expressed as Arbitrary Unit (A.U.).

LV.pF8.1.hBDD-FVIII and LV.pF8.2.hBDD-FVIII Delivery in Hemophilic Mice Corrects the Bleeding Phenotype In order to investigate whether pF8 was suitable for gene therapy application because of its ability to drive in vivo FVIII expression in endothelial and myeloid cells, $1\times10^9$ TU of LV.pF8.1.hBDD-FVIII and LV.pF8.2.hBDD-FVIII were injected in 5-6 C57BL/6 HA mice per LV via tail vein. The same TU of LV.pF8.1.hBDD-FVIII were also injected in 7 C57/129 HA mice per LV via tail vein. Before sacrifice mice were tail clip challenged and blood loss was measured.

Luciferase Assay

The seq ID1, seq ID2 and ID8 fragments were cloned into the pNL1.1[Nluc] vector (Promega) using XhoI and blunted HindIII restriction sites. The endothelial transcription factor (TF) genes Ets1 and Ets2 were used to investigate the promoter activity of both NLuc seq ID1, NLuc seq ID2 and NLucseq ID8 2 and expressed under the control of CMV promoter. The coding sequence of ETS2 transcription factor gene was already present in our laboratory while the plasmid containing the coding sequence of ETS1 was bought from Origene, Rockville, Md.).

The constructs expressing luciferase reporter gene under the control of both seq ID NO: 1, 2 and 8 fragments were transiently transfected using Lipofectamine™ 2000 Transfection Reagent (Thermo Fisher scientific) in HECV cell line either alone or in combination with Ets1, Ets2 transcription factors. Transfection was performed using 240 ng of plasmid DNA from each construct. Cell lysis was performed at 24 hours after transfection using 1× Passive Lysis Buffer (PLB) (Promega). NanoLuc® and Firefly luciferase reporter activities were measured by using the NanoDLR™ Assay (Promega) according to the manufacturer's instructions. Luminescence was read at 560 nm on a Victor X (PerkinElmer, Waltham, Mass.).

The transcription activity of the fragments were expressed as the ratio between the average of (Nluc/Firefly) of NLuc seq ID1, NLuc seq ID2 and NLucseq ID8 co-transfected with the transcription factors (Ets1, Ets2) and the average of (Nluc/Firefly) of NLuc seq ID1, NLuc seq ID2 and NLucseq ID8 alone.

Results

In Vitro pF8 Activity

To assess pF8 activity in vitro we introduced combinations of several sequences from the human FVIII promoter in a lentiviral transfer construct containing GFP as gene reporter as previously disclosed (FIGS. 1 and 2). The LV and the control LV which express the GFP under the control of the ubiquitous promoter of the phosphoglycerate kinase gene (PGK) (LV.PGK.GFP) were used to transduce at MOI 0.2 several human cell lines of endothelial (hECV and HUVEC), hematopoietic (DAMI megakariocytic cell line, U937 monocytic cell line, jurkat T cell line and SSK41 neoplastic B cell line) and hepatic origin (HepG2 and Huh7) according to the presence of cell specific TF identified performing a bioinformatic analysis.

Interestingly, despite the prediction of several hepatocytes specific TF, pF8 is less efficient to drive GFP expression in the hepatic cell lines HepG2 and Huh7 in comparison with the PGK promoter used as control at the same MOI. Similarly, to hepatocytes, low GFP expression was observed in primary human foreskin fibroblast (HFF) after transduction in comparison with PGK. Meanwhile GFP expression difference between F8 and PGK promoters decreased in endothelial (hECV and HUVEC), myeloid (DAMI and U937) and lymphoid cell lines (Jurkat and SSK41).

These data suggest that, in vitro, the disclosed promoter F8 constructs drive transgene expression specifically in endothelial and hematopoietic cell lines.

In Vitro Analysis of FVIII Promoter Activity.

To assess the novel FVIII promoter specificity for endothelial cells we evaluated the capacity of the SEQ ID NO: 1, SEQ ID NO: 2 and SEQ ID NO: 12 FVIII promoter fragments to drive the expression of the luciferase reporter gene in the presence of two endothelial TFs (Ets-1 and Ets-2). These TFs were selected based on an in silico analysis performed to identify TFs involved in the control of FVIII promoter activity. Using HECV cell line we analyzed the effects of the endothelial TFs on the activation of the 3 forms of FVIII promoter sequences selected. This allowed us to identify an up-regulation of luciferase activity when both Ets-1 and Ets-2 where co-transfected, pointing to a synergistically effect of these two TFs (FIGS. 6 A, B and C). Moreover, the presence of Ets-1 alone despite was able to increase the activity of all promoters did not rich the same efficiency obtained with the co-transfection of both TFs. On the contrary, Ets-2 alone was completely unable to increase promoter activation in our system.

In Vivo pF8 Activity

We injected 5×108 TU of LV.pF8.1.GFPin C57BL/6 mice GFP expression was evaluated in several organs by FACS and immunofluorescence (IF) analysis at different time points after LV injection (1, 2, 4, 8, 12 and 24 weeks). In hematopoietic organs, such as spleen and BM, GFP expression was sustained up to 1 month (10-22% in BM and 4-10% in spleen) and was predominantly restricted to myeloid cells as shown by CD11b, CD11c and F4/80 co-staining assessed by FACS. Little co-staining was assessed in BM with cell-specific markers for B cells with B220, and granulocytes with Gr-1. While in the spleen pF8 seems to be less active in CD4 and CD8 subpopulation, more B220 GFP+ cells were detected when compared with BM.

To better identify which NPC subpopulation specifically expresses GFP under the control of pF8 constructs disclosed above, we performed further characterizations. In particular, we evaluated the co-expression by FACS and IF of GFP and LSEC or KC-specific markers and we observed that pF8 was active mainly in LSEC.

These results were confirmed by IF up to 6 months after LV injection in which we observed a strong co-expression between GFP and Lyve-1 but virtually no F4/80-GFP double positive cells were detected.

Interestingly, by IF, GFP expression resulted absent in hepatocytes. On the contrary, when we analyzed the spleen of injected mice we detected GFP in macrophages with few GFP+ endothelial cells (EC).

To further characterize the differential GFP expression in these organs, we injected additional mice (n=3) with a LV.pF8.GFP containing at the 3' of the expression cassette the miRNA target (mirT) sequence of the specific hematopoietic miRNA 142-3p (mirT-142-3p) or the endothelial miRNA 126 (mirT-126) to avoid transgene expression selectively in these cell types. As expected, in the liver the presence of mirT 142-3p does not reduce the amount of GFP expressing cells, while in the spleen GFP was strongly reduced. On the contrary, including the mirT 126 sequence drastically silenced GFP expression in the liver but not in the spleen in which GFP expression is maintained in F4/80+ macrophages.

Thus, our in vivo studies demonstrated that the claimed FVIII promoter regions are active in endothelial cells and monocyte/macrophages with a particular expression pattern based on the organ analyzed.

pF8 is Functional in Hematopoietic Cells

In order to restrict our studies of the disclosed sequences activity in hematopoietic cells, we transplanted LV.pF8.1.GFP and LV.PGK.GFP (control) lineage minus (Lin−) transduced cells isolated from recipient mice in busulfan-conditioned C57BL/6 mice. FACS analysis of the blood of transplanted mice starting 4 weeks after transplantation showed that total cell were ≥15% GFP+ for pF8 and ≥60% for PGK meaning that the disclosed sequences are active in BM-derived cells. Moreover, GFP expression in recipient blood cells was stable without significant changes up to 4 months when mice were killed and organs analyzed. GFP positivity was observed by FACS at various levels in all organs examined, suggesting that the disclosed sequences of the FVIII promoter are active also in hematopoietic cells distributed in several tissues such as BM, spleen, thymus and liver NPC.

To further clarify in which hematopoietic cell types pF8 is mainly active, several cell specific markers were analyzed to find the co-expression with GFP in each organ by FACS and IF.

In the blood, the disclosed sequences of FVIII promoter driven GFP expression mainly in myeloid cells as shown by CD11b and Gr-1 co-staining, however we detected less GFP expression in granulocytes compared with CD11b+ monocytes. On the other hand, very low co-staining was assessed between GFP and lymphocytic specific markers such as CD19 for B cells and CD4 and CD8 for T cells. The specific activity of the disclosed sequences was further confirmed by analyzing PGK-Lin− transplanted mice blood in which GFP expression was observed without differences both in myeloid and lymphoid cells. Similarly, to blood, in BM, GFP expression was detected predominantly in CD11b+ myeloid cells rather than in B-lymphocytes. Interestingly, in contrast with what we observed in direct LV injection less GFP expression was detected in ScaI+ hematopoietic progenitor cells. Additionally, in the spleen GFP was expressed mainly in myeloid cells (stained with CD11b and CD11c) in comparison with lymphocytes (CD3 for T cells and CD19 for B cells). Regarding the liver, IF staining on liver sections of pF8-Lin− transplanted mice showed the presence of F4/80-GFP expressing cells that are less in comparison with those transduced with the PGK promoter. Similarly to liver, in the spleen of pF8-Lin− mice, GFP positivity was restricted in F4/80+ macrophages whereas PGK drives GFP expression also in the germinal centers rich in B cells. This suggests that in the spleen, the disclosed sequences of the FVIII promoter are more active in myeloid cells in comparison to lymphocytes.

LV-pF8-FVIII Delivery in Hemophilic Mice Corrects the Bleeding Phenotype

In order to understand if the disclosed sequences of FVIII promoter were suitable for gene therapy application because of its ability to drive in vivo FVIII specific expression in endothelial and myeloid cells 1×10$^9$ TU of lentivirus LV.pF8.1.hBDD-FVIII and LV.pF8.2.hBDD-FVIII (lentivirus vectors comprising SEQ ID NO:1 and SEQ ID NO: 2 of the FVIII promoter region) were tail vein injected in six C57BL/6 HA mice.

aPTT assay on plasma of treated mice showed the presence of therapeutic levels of FVIII activity (≥10%) up to 1 year (FIG. 3A-4A).

Noteworthy, in contrast with mice injected with LV.PGK.BDD-FVIII, by ELISA we did not detect anti-FVIII antibodies in the plasma of all injected mice overtime (FIG. 3B-4B).

Finally, mice were tail clip challenged and blood loss was measured.

All injected mice had a reduced blood loss in comparison with control HA (haemophilic A) mice obtaining results more similar to the wild type mice, demonstrating an improvement in the coagulation (FIG. 3C). Moreover, blood loss (FIG. 4C) and bleeding time (FIG. 4D) 1 year after LV injection confirmed achievement of robust phenotypic correction in all treated mice.

For LV.pF8.2.BDD-FVIII, mice were also immunized after 24 weeks by using 20 pg of ReFacto® (Pfizer) in incomplete Freund's adjuvant injected subcutaneously and plasma samples were analyzed from 2 weeks after immunization.

With this experiment we demonstrated that even if you immunize hemophilic mice with FVIII after gene therapy you do not mount an immune response against FVIII that continue to be secreted without specific antibodies formation.

Moreover, we induced anti-FVIII antibodies in HA mice by subcutaneous injection of Refacto® in IFA. When anti-FVIII antibodies appeared (4 weeks later), mice were injected by tail vein with $10^9$ TU of LV.pF8.1.hBDD-FVIII (n=4) (FIG. 5A). Injected mice expressed an average of 6% hFVIII 2 weeks after injection and remained stable in the following weeks for up to 52 weeks (see FIG. 5) (the longest time tested), while anti-FVIII antibody titers in the plasma of these mice decreased over time starting from 4 weeks after LV injection (FIG. 5A). Again, 1 year after LV delivery blood loss and bleeding time assays demonstrated that phenotypic correction was achieved in all injected FVIII-immunized mice (FIGS. 5B and C).

These data demonstrate that we were able to reverse the pre-existing anti-FVIII immunity in HA mice, since inhibitors levels in the plasma of these mice decreased with a concomitant correlated increase of FVIII activity.

To improve FVIII levels using pF8 as promoter we generated LVs in which BDD-FVIII was substitute with more active forms of FVIII such as FVIII.RH and FVIII.N6.

For the experiment, 3 mice for each FVIII variant were injected with LV.pF8.FVIII.RH, LV.pF8.FVIII.N6 and LV.pF8.FVIII as control. Mice injected with LV.pF8.FVIII.N6 received half vector dose ($5\times10^8$ TU). As results we obtained up to twice more FVIII activity in mice injected with FVIII.RH (6-10%) in comparison to BDD.FVIII (4-7%) while similar FVIII levels (~5%) were achieved in mice injected with FVIII.N6 even using a reduced dose of LV.

FVIII Expression in B6/129 Hemophilia A Mice

To study whether FVIII production under the control of pF8.1 sequence would support long-term transgene expression in a different immunocompetent mouse strain, we injected B6/129 HA mice (n=7) with $10^9$ TU LV.pF8.1-hFVIII. Two weeks after LV injection, 8% of human FVIII activity was detected in plasma of treated mice and 28 weeks after injection the activity reached up to 12% (FIG. 7A). Moreover, no anti-FVIII antibodies were detected in plasma of LV-injected B6/129-HA mice confirming that correction was achieved in all treated mice in absence of immune responses to the transgene (FIG. 7B).

Ex Vivo Gene Therapy

In order to verify if ex vivo transplantation of both human and mouse HSC transduced with LV.pF8.1.hBDD-FVIII reached FVIII therapeutic levels in busulfan-treated HA mice. Human CD34+ cells were LV-transduced with MOI 30 while Lin⁻ isolated from C57BL/6 HA mice with MOI 100. Copy number integration analysis showed a mean of 4.4 LV genome per cell for CD34⁺ and 3.2 copies for Lin⁻. Human HSC (6×105) were injected in 6 NOD/SCID γ null-HA mice whereas $10^6$ Lin⁻ cells were administered to 3 C57BL/6 HA mice. As control in the CD34 group 3 mice were transplanted with untransduced human CD34⁺ cells. Human cells engraftment was evaluated by FACS as percentage of hCD45⁺ cells in blood of transplanted mice showing a chimerism around 30% up to 4 months after transplantation. aPTT assay on plasma of LV-transduced CD34 transplanted mice showed therapeutic levels of FVIII activity around 8-10% of normal meanwhile transplantation of untransduced CD34⁺ cells reached 2% of activity. Similar results were assessed by transplanting LV.pF8.1.hBDD-FVIII-transduced murine Lin⁻ cells. Indeed, in LV-injected C57Bl/6-HA mice, FVIII activity was restored at 5-6%. Moreover, the mouse plasma of these mice was also tested for antibodies formation that were absent demonstrating that no immune response was developed until the end of the experiment 6 months later.

The invention claimed is:

1. A vector expressing a therapeutic gene, wherein the vector comprises an isolated promoter, wherein the isolated promoter consists of SEQ ID NO: 2.

2. The vector according to claim 1, wherein the therapeutic gene is FVIII.

3. The vector according to claim 1, wherein SEQ ID NO: 2 is alone or in combination with SEQ ID NO: 8 and/or 9.

4. The vector according to claim 1, wherein SEQ ID NO: 8 and/or 9 is positioned upstream and/or downstream SEQ ID NO: 2.

5. The vector according to claim 1 or a polynucleotide sequence SEQ ID NO: 2 further comprising at least one pharmaceutically acceptable excipient.

* * * * *